US011639928B2

(12) United States Patent
Mikkelsen et al.

(10) Patent No.: US 11,639,928 B2
(45) Date of Patent: May 2, 2023

(54) METHODS AND SYSTEMS FOR CHARACTERIZING ANALYTES FROM INDIVIDUAL CELLS OR CELL POPULATIONS

(71) Applicant: 10X GENOMICS, INC., Pleasanton, CA (US)

(72) Inventors: Tarjei Sigurd Mikkelsen, Dublin, CA (US); Eswar Prasad Ramachandran Iyer, Sunnyvale, CA (US); Andrew Kohlway, Pleasanton, CA (US); Luigi Jhon Alvarado Martinez, Walnut Creek, CA (US); Katherine Pfeiffer, Oakland, CA (US); Andrew D. Price, Hayward, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 17/680,209

(22) Filed: Feb. 24, 2022

(65) Prior Publication Data
US 2022/0276229 A1    Sep. 1, 2022

Related U.S. Application Data

(63) Continuation of application No. 17/229,557, filed on Apr. 13, 2021, now abandoned, which is a
(Continued)

(51) Int. Cl.
*G01N 33/532* (2006.01)
*C12N 15/85* (2006.01)
(Continued)

(52) U.S. Cl.
CPC ..... *G01N 33/532* (2013.01); *C07K 14/70539* (2013.01); *C12N 15/1037* (2013.01);
(Continued)

(58) Field of Classification Search
None
See application file for complete search history.

(56) References Cited

U.S. PATENT DOCUMENTS

| 4,124,638 | A | 11/1978 | Hansen |
| 5,185,099 | A | 2/1993 | Delpuech et al. |

(Continued)

FOREIGN PATENT DOCUMENTS

| CN | 106460033 A | 2/2017 |
| EP | 1019496 B1 | 9/2004 |

(Continued)

OTHER PUBLICATIONS

10X Genomics, Inc. CG000153 Rev A. Chromium Single Cell DNA Reagent Kits User Guide. 2018.
(Continued)

*Primary Examiner* — Kaijiang Zhang
(74) *Attorney, Agent, or Firm* — Wilson Sonsini Goodrich & Rosati

(57) ABSTRACT

The present disclosure provides methods of processing or analyzing a sample. A method for processing a sample may comprise hybridizing a probe molecule to a target region of a nucleic acid molecule (e.g., a ribonucleic acid (RNA) molecule), barcoding the probe-nucleic acid molecule complex, and performing extension, denaturation, and amplification processes. A method for processing a sample may comprise hybridizing first and second probes to adjacent or non-adjacent target regions of a nucleic acid molecule (e.g., an RNA molecule), linking the first and second probes to provide a probe-linked nucleic acid molecule, and barcoding the probe-linked nucleic acid molecule. One or more processes of the methods described herein may be performed within a partition, such as a droplet or well. One or more
(Continued)

processes of the methods described herein may be performed on a cell, such as a permeabilized cell.

29 Claims, 30 Drawing Sheets

Related U.S. Application Data continuation of application No. 16/554,564, filed on Aug. 28, 2019, now abandoned, which is a continuation-in-part of application No. PCT/US2019/019309, filed on Feb. 22, 2019.

(60) Provisional application No. 62/804,648, filed on Feb. 12, 2019, provisional application No. 62/633,982, filed on Feb. 22, 2018.

(51) Int. Cl.

| | | |
|---|---|---|
| *G01N 33/543* | (2006.01) | |
| *G01N 33/548* | (2006.01) | |
| *C12N 15/10* | (2006.01) | |
| *C12Q 1/6806* | (2018.01) | |
| *G01N 33/50* | (2006.01) | |
| *G01N 33/53* | (2006.01) | |
| *G01N 33/58* | (2006.01) | |
| *C12Q 1/6818* | (2018.01) | |
| *C12Q 1/6827* | (2018.01) | |
| *C12Q 1/6881* | (2018.01) | |
| *C12N 15/11* | (2006.01) | |
| *G01N 33/569* | (2006.01) | |
| *C40B 70/00* | (2006.01) | |
| *C40B 30/04* | (2006.01) | |
| *C40B 50/06* | (2006.01) | |
| *C07K 14/74* | (2006.01) | |
| *C12Q 1/6804* | (2018.01) | |

(52) U.S. Cl.
CPC ..... *C12N 15/1055* (2013.01); *C12N 15/1065* (2013.01); *C12N 15/1075* (2013.01); *C12N 15/11* (2013.01); *C12N 15/85* (2013.01); *C12Q 1/6804* (2013.01); *C12Q 1/6806* (2013.01); *C12Q 1/6818* (2013.01); *C12Q 1/6827* (2013.01); *C12Q 1/6881* (2013.01); *G01N 33/505* (2013.01); *G01N 33/5032* (2013.01); *G01N 33/5304* (2013.01); *G01N 33/5306* (2013.01); *G01N 33/5308* (2013.01); *G01N 33/548* (2013.01); *G01N 33/54306* (2013.01); *G01N 33/54366* (2013.01); *G01N 33/56977* (2013.01); *G01N 33/58* (2013.01); *C12N 2310/20* (2017.05); *C12N 2320/10* (2013.01); *C12Q 2537/164* (2013.01); *C12Q 2563/179* (2013.01); *C12Q 2563/185* (2013.01); *C12Q 2565/1015* (2013.01); *C40B 30/04* (2013.01); *C40B 50/06* (2013.01); *C40B 70/00* (2013.01)

(56) References Cited

U.S. PATENT DOCUMENTS

| | | |
|---|---|---|
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,828,098 B2 | 12/2004 | Langmore et al. |
| 6,915,679 B2 | 7/2005 | Chien et al. |
| 6,964,847 B1 | 11/2005 | Englert |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,709,197 B2 | 5/2010 | Drmanac |
| 7,772,287 B2 | 8/2010 | Higuchi et al. |
| 7,776,927 B2 | 8/2010 | Chu et al. |
| 7,838,270 B2 | 11/2010 | Davydova et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,460,866 B2 | 6/2013 | Van Eijk et al. |
| 8,574,847 B2 | 11/2013 | Becker et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,370 B2 | 4/2015 | Hong |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |

(56) References Cited

U.S. PATENT DOCUMENTS

| | | |
|---|---|---|
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,758,814 B2 | 9/2017 | Fehr et al. |
| 9,764,322 B2 | 9/2017 | Hiddessen et al. |
| 9,824,068 B2 | 11/2017 | Wong |
| 9,834,765 B2 | 12/2017 | Bergmann et al. |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,144,950 B2 | 12/2018 | Nolan |
| 10,174,310 B2 | 1/2019 | Nolan |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,459,607 B1 | 10/2022 | Terry et al. |
| 11,467,153 B2 | 10/2022 | Belhocine et al. |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0198980 A1 | 10/2003 | Greenfield et al. |
| 2003/0215862 A1 | 11/2003 | Parce et al. |
| 2004/0086892 A1 | 5/2004 | Crothers et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0034603 A1 | 2/2012 | Oliphant et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2013/0203605 A1 | 8/2013 | Shendure et al. |
| 2013/0210079 A1 | 8/2013 | Stanojevic et al. |
| 2013/0261196 A1 | 10/2013 | Diamond et al. |
| 2013/0296172 A1 | 11/2013 | Fu et al. |
| 2014/0065234 A1 | 3/2014 | Shum et al. |
| 2014/0155295 A1 | 6/2014 | Hindson et al. |
| 2014/0170653 A1 | 6/2014 | Ying |
| 2014/0221217 A1* | 8/2014 | Van Eijk et al. .... C12Q 1/6827 506/9 |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0133344 A1 | 5/2015 | Shendure et al. |
| 2015/0265995 A1 | 9/2015 | Head et al. |
| 2015/0267191 A1 | 9/2015 | Steelman et al. |
| 2015/0284786 A1 | 10/2015 | Shapero et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0138086 A1 | 5/2016 | Seelig et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0191113 A1 | 7/2017 | Barany |
| 2017/0235876 A1 | 8/2017 | Jaffe et al. |
| 2017/0260584 A1 | 9/2017 | Zheng et al. |
| 2018/0023119 A1 | 1/2018 | Adey et al. |
| 2018/0023138 A1 | 1/2018 | Collins et al. |
| 2018/0030515 A1 | 2/2018 | Regev et al. |
| 2018/0073073 A1 | 3/2018 | Fu et al. |
| 2018/0080075 A1 | 3/2018 | Brenner et al. |
| 2018/0105808 A1 | 4/2018 | Mikkelsen et al. |
| 2018/0127816 A1 | 5/2018 | Teo et al. |

(56) References Cited

U.S. PATENT DOCUMENTS

| | | |
|---|---|---|
| 2018/0265917 A1 | 9/2018 | Barany et al. |
| 2018/0273933 A1 | 9/2018 | Gunderson et al. |
| 2018/0312822 A1 | 11/2018 | Lee et al. |
| 2018/0312873 A1 | 11/2018 | Zheng |
| 2018/0320241 A1 | 11/2018 | Nolan |
| 2018/0340169 A1 | 11/2018 | Belhocine et al. |
| 2018/0340939 A1 | 11/2018 | Gaublomme et al. |
| 2018/0355348 A1 | 12/2018 | Adey et al. |
| 2018/0371545 A1 | 12/2018 | Wong et al. |
| 2019/0040382 A1 | 2/2019 | Steemers et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0256547 A1 | 8/2019 | Routh et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0224243 A1 | 7/2020 | Desai et al. |
| 2020/0224244 A1 | 7/2020 | Nilsson et al. |
| 2020/0239874 A1 | 7/2020 | Mikkelsen et al. |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0040551 A1 | 2/2021 | Mikkelsen et al. |
| 2021/0190770 A1 | 6/2021 | Delaney et al. |
| 2021/0230584 A1 | 7/2021 | Mikkelsen et al. |
| 2021/0270703 A1 | 9/2021 | Abousoud |
| 2022/0403452 A1 | 12/2022 | Lance et al. |

FOREIGN PATENT DOCUMENTS

| | | | |
|---|---|---|---|
| EP | 1841879 A2 | 10/2007 | |
| EP | 1967592 B1 | 4/2010 | |
| EP | 2540389 A1 | 1/2013 | |
| EP | 2635679 B1 | 4/2017 | |
| GB | 2097692 A | 11/1982 | |
| GB | 2097692 B | 5/1985 | |
| WO | WO-84/02000 | 5/1984 | |
| WO | WO-95/30782 | 11/1995 | |
| WO | WO-99/52708 | 10/1999 | |
| WO | WO-2000008212 A1 | 2/2000 | |
| WO | WO-2001002850 A1 | 1/2001 | |
| WO | WO-0114589 A2 | 3/2001 | |
| WO | WO-0190418 A1 | 11/2001 | |
| WO | WO-2001089787 A2 | 11/2001 | |
| WO | WO-2004002627 A2 | 1/2004 | |
| WO | WO-2004065617 A2 | 8/2004 | |
| WO | WO-2004069849 A2 | 8/2004 | |
| WO | WO-2004091763 A2 | 10/2004 | |
| WO | WO-2005021151 A1 | 3/2005 | |
| WO | WO-2005021794 A2 | 3/2005 | |
| WO | WO-2005049787 A9 | 6/2005 | |
| WO | WO-2005082098 A2 | 9/2005 | |
| WO | WO-2006040551 A2 | 4/2006 | |
| WO | WO-2006078841 A1 | 7/2006 | |
| WO | WO-2006096571 A2 | 9/2006 | |
| WO | WO-2007081385 A2 | 7/2007 | |
| WO | WO-2007081387 A1 | 7/2007 | |
| WO | WO-2007089541 A2 | 8/2007 | |
| WO | WO-2007133710 A2 | 11/2007 | |
| WO | WO-2007140015 A2 | 12/2007 | |
| WO | WO-2007147079 A2 | 12/2007 | |
| WO | WO-2008021123 A1 | 2/2008 | |
| WO | WO-2008109176 A2 | 9/2008 | |
| WO | WO-2008121342 A2 | 10/2008 | |
| WO | WO-2008134153 A1 | 11/2008 | |
| WO | WO-2008150432 A1 | 12/2008 | |
| WO | WO-2009011808 A1 | 1/2009 | |
| WO | WO-2009015296 A1 | 1/2009 | |
| WO | WO-2009085215 A1 | 7/2009 | |
| WO | WO-2009152928 A2 | 12/2009 | |
| WO | WO-2010033200 A2 | 3/2010 | |
| WO | WO-2010104604 A1 | 9/2010 | |
| WO | WO-2010117620 A2 | 10/2010 | |
| WO | WO-2010148039 A2 | 12/2010 | |
| WO | WO-2011028539 A1 | 3/2011 | |
| WO | WO-2011047870 A1 | 4/2011 | |
| WO | WO-2011056546 A1 | 5/2011 | |
| WO | WO-2011066476 A1 | 6/2011 | |
| WO | WO-2012048341 A1 | 4/2012 | |
| WO | WO-2012061832 A1 | 5/2012 | |
| WO | WO-2012083225 A2 | 6/2012 | |
| WO | WO-2012106385 A2 | 8/2012 | |
| WO | WO-2012106546 A2 | 8/2012 | |
| WO | WO-2012112804 A1 | 8/2012 | |
| WO | WO-2012112970 A2 | 8/2012 | |
| WO | WO-2012116331 A2 | 8/2012 | |
| WO | WO-2012142531 A2 | 10/2012 | |
| WO | WO-2012142611 A2 | 10/2012 | |
| WO | WO-2012149042 A2 | 11/2012 | |
| WO | WO-2012166425 A2 | 12/2012 | |
| WO | WO-2012167142 A2 | 12/2012 | |
| WO | WO-2013019751 A1 | 2/2013 | |
| WO | WO-2013036929 A1 | 3/2013 | |
| WO | WO-2013055955 A1 | 4/2013 | |
| WO | WO-2013096643 A1 | 6/2013 | |
| WO | WO-2013123220 A1 | 8/2013 | |
| WO | WO-2013126741 A1 | 8/2013 | |
| WO | WO-2013134261 A1 | 9/2013 | |
| WO | WO-2013192292 A1 | 12/2013 | |
| WO | WO-2014026032 A2 | 2/2014 | |
| WO | WO-2014028378 A2 | 2/2014 | |
| WO | WO-2014108810 A2 | 7/2014 | |
| WO | WO-2014165559 A2 | 10/2014 | |
| WO | WO-2015015199 A2 | 2/2015 | |
| WO | WO-2015044428 A1 | 4/2015 | |
| WO | WO-2015164212 A1 | 10/2015 | |
| WO | WO-2016040476 A1 | 3/2016 | |
| WO | WO-2016061517 A1 | 4/2016 | |
| WO | WO-2016100976 A2 | 6/2016 | |
| WO | WO-2016126871 A2 | 8/2016 | |
| WO | WO-2016135800 A1 | 9/2016 | |
| WO | WO-2016168584 A1 | 10/2016 | |
| WO | WO-2017015075 A1 | 1/2017 | |
| WO | WO-2017044993 A2 * | 3/2017 | ........... C12Q 1/6827 |
| WO | WO-2017066231 A1 | 4/2017 | |
| WO | WO-2017075265 A1 * | 5/2017 | ........... C12Q 1/6811 |
| WO | WO-2017180949 A1 | 10/2017 | |
| WO | WO-2017184707 A1 | 10/2017 | |
| WO | WO-2017197343 A2 | 11/2017 | |
| WO | WO-2018039338 A1 | 3/2018 | |
| WO | WO-2018091676 A1 | 5/2018 | |
| WO | WO-2018119301 A1 | 6/2018 | |
| WO | WO-2018119447 A2 | 6/2018 | |
| WO | WO-2018138237 A1 | 8/2018 | |
| WO | WO-2018172726 A1 | 9/2018 | |
| WO | WO-2018191701 A1 | 10/2018 | |
| WO | WO-2018213643 A1 | 11/2018 | |
| WO | WO-2018226546 A1 | 12/2018 | |
| WO | WO-2018236615 A1 | 12/2018 | |
| WO | WO-2019028166 A1 | 2/2019 | |
| WO | WO-2019038372 A1 | 2/2019 | |
| WO | WO-2019040637 A1 | 2/2019 | |
| WO | WO-2019083852 A1 | 5/2019 | |
| WO | WO-2019084043 A1 | 5/2019 | |
| WO | WO-2019084165 A1 | 5/2019 | |
| WO | WO-2019108851 A1 | 6/2019 | |
| WO | WO-2019113235 A1 | 6/2019 | |
| WO | WO-2019118355 A1 | 6/2019 | |
| WO | WO-2019126789 A1 | 6/2019 | |

(56) References Cited

FOREIGN PATENT DOCUMENTS

| WO | WO-2019148042 A1 | 8/2019 |
|---|---|---|
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019173638 A1 | 9/2019 |
| WO | WO-2019191321 A1 | 10/2019 |
| WO | WO-2019217758 A1 | 11/2019 |
| WO | WO-2019236599 A2 | 12/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021041974 A1 | 3/2021 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |

OTHER PUBLICATIONS

10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Agasti, S.S. et al. "Photocleavable DNA barcode-antibody conjugates allow sensitive and multiplexed protein analysis in single cell" J Am Chem Soc (2012) 134(45):18499-18502.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Boulanger, et al, "Massively parallel haplotyping on microscopic beads for the high-throughput phase analysis of single molecules", PLoS One, vol. 7:1-10, 2012.
Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci USA. Feb. 15, 2000;97(4):1665-70.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Cao, et al. Comprehensive single-cell transcriptional profiling of a multicellular organism. Science 357.6352 (2017): 661-667.
Cao, et al. Joint profiling of chromatin accessibility and gene expression in thousands of single cells. Science. Sep. 28, 2018;361(6409):1380-1385. doi: 10.1126/science.aau0730. Epub Aug. 30, 2018.
Cao, et al. The single-cell transcriptional landscape of mammalian organogenesis. Nature 566.7745 (2019): 496-502.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/708,214, inventors Wheeler; Tobias Daniel et al., filed Dec. 9, 2019.
Co-pending U.S. Appl. No. 16/737,762, inventors Price; Andrew D. et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 16/800,450, inventor Katherine; Pfeiffer, filed Feb. 25, 2020.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/499,039, inventors Pfeiffer; Katherine et al., filed Oct. 12, 2021.

(56) References Cited

OTHER PUBLICATIONS

Co-pending U.S. Appl. No. 17/512,241, inventors Hill; Andrew John et al., filed Oct. 27, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Cusanovich, et al. Multiplex single-cell profiling of chromatin accessibility by combinatorial cellular indexing. Science, May 22, 2015;348(6237):910-14.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dostie et al., "Chromosome Conformation Capture Carbon Copy (5C): a massively parallel solution for mapping interaction between genomic elements," Genome research, 2006, vol. 16, No. 10, pp. 1299-1309.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011;44:5539-5553.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-59.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Gehring, et al. Highly Multiplexed Single-Cell RNA-seq for Defining Cell Population and Transcriptional Spaces. bioRxiv (2018): 315333.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Holtze, et al. Biocompatible surfactants forwater-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hug, et al. Measurement of the number of molecules of a single mRNA species in a complex mRNA preparation. J Theor Biol. Apr. 21, 2003;221(4):615-24.
Islam, et al. Highly multiplexed and strand-specific single-cell RNA 5' end sequencing. Nat Protoc. Apr. 5, 2012;7(5):813-28. doi: 10.1038/nprot.2012.022.
Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(suppl15):4742.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute Nos. of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015; 161:1187-1201.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip the Royal Soc. of Chem. 8: 1110-1115 (2008).
Kvastad et al., Single cell analysis of cancer cells using an improved RT-MLPA method has potential for cancer diagnosis and monitoring, Scientific Reports 5:16519; Nov. 12, 2015.
Lagally, et al. Single-Molecular DNA Amplification and Analysis in an Integrated Microfluidic Device. Anal Chem. Feb. 1, 2001;73(3):565-70.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lennon et al. A scalable, fully automated process for construction of sequence-ready barcoded libraries for 454. Genome Biology 11:R15 (2010).
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Lundin, et al, "Hierarchical molecular tagging to resolve long continuous sequences by massively parallel sequencing", Sci Rep., 3:1186, 2013.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Chritopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Mulqueen, et al. Scalable and efficient single-cell DNA methylation sequencing by combinatorial indexing. bioRxiv. Jun. 28, 2017.
Myllykangas et al. "Efficient targeted resequencing of human germline and cancer genomes by oligonucleotide-selective sequencing," Nat Biotechnol, (2011) 29:1024-1027.
Myllykangas et al., Targeted Sequencing Library Preparation by Genomic DNA Circularization, BMC Biotechnology, 2011, 11(122), 1-12.
Navin. The first five years of single-cell cancer genomics and beyond. Genome Res. Oct. 2015;25(10):1499-507. doi: 10.1101/gr.191098.115.

(56) References Cited

OTHER PUBLICATIONS

Nisisako, et al. Droplet formation in a microchannel network. Lab Chip. Feb. 2002;2(1):24-6. Epub Jan. 18, 2002.

Nisisako, T. et al. Droplet Formation in a Microchannel on PMMA Plate. Micro Total Analysis Systems. 2001. Kluwer Academic Publishers. pp. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, R. et al., "Single cell multiplex gene detection and sequencing using microfluidicallygenerated agarose emulsions" Angew. Chem. Int. Ed. Engl. (2011) 50(2):390-395.

Orakdogen, N. "Novel responsive poly(N,N-dimethylaminoethyl methacrylate) gel beads: preparation, mechanical properties and pH-dependent swelling behavior" J Polym Res (2012) 19:9914.

Perrott, Jimmy. Optimization and Improvement of Emulsion PCR for the Ion Torrent Next-Generation Sequencing Platform. (2011) Thesis.

Peters, B.A. et al. Accurate whole-genome sequencing and haplotyping from 10 to 20 human cells. Nature, 487(7406):190-195 (Jul. 11, 2012).

Plunkett, et al. Chymotrypsin responsive hydrogel: application of a disulfide exchange protocol for the preparation of methacrylamide containing peptides. Biomacromolecules. Mar.-Apr. 2005;6(2):632-7.

Priest, et al. Generation of Monodisperse Gel Emulsions in a Microfluidic Device, Applied Physics Letters, 88:024106 (2006).

Pushkarev et al. "Single-molecule sequencing of an individual human genome," Nature Biotech (2009) 27:847-850.

Ramani, et al. Massively multiplex single-cell Hi-C. Nat Methods. Mar. 2017; 14(3): 263-266. Published online Jan. 30, 2017.doi: 10.1038/nmeth.4155.

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL:http://454.com/downloads/my454/documentation/technical-bulletins/TCB-09004 Using MultiplexIdentifierAdaptorsForTheGSFLXTitaniumSeriesChemistry-BasicMIDSet.pdf.

Rodrigue, S. et al. "Whole genome amplification and de novo assembly of single bacterial cells" PLoS One. Sep. 2, 2009;4(9):e6864. doi: 10.1371/journal.pone.0006864.

Rosenberg, et al. SPLiT-seq reveals cell types and lineages in the developing brain and spinal cord. Science (New York, NY) 360. 6385 (2018): 176-182.

Rotem, A. et al., "High-throughput single-cell labeling (Hi-SCL) for RNA-Seq using drop-based microfluidics" PLOS One (May 22, 2015) 0116328 (14 pages).

Rotem, A. et al. "Single Cell Chip-Seq Using Drop-Based Microfluidics" Abstract #50. Frontiers of Single Cell Analysis, Stanford University Sep. 5-7, 2013.

Saikia, et al. Simultaneous multiplexed amplicon sequencing and transcriptome profiling in single cells. Nat Methods. Jan. 2019;16(1):59-62. doi: 10.1038/S41592-018-0259-9. Epub Dec. 17, 2018.

Schubert, et al. Microemulsifying fluorinated oils with mixtures of fluorinated and hydrogenated surfactants. Colloids and Surfaces A; Physicochemical and Engineering Aspects, 84(1994) 97-106.

Seiffert, et al. Microfluidic fabrication of smart microgels from macromolecular precursors. Polymer. vol. 51, Issue 25, Nov. 26, 2010, pp. 5883-5889.

Seiffert, S. et al., "Smart microgel capsules from macromolecular precursors" J. Am. Chem. Soc. (2010) 132:6606-6609.

Shah, et al. "Fabrication of mono disperse thermosensitive microgels and gel capsules in micro fluidic devices", Soft Matter, 4:2303-2309 (2008).

Shembekar, et al. "Droplet-based microfluidics in drug discovery, transcriptomics and high-throughput molecular genetics" LabChip (2016) 16(8):1314-1331.

Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.

Smith, et al. Highly-multiplexed barcode sequencing: an efficient method for parallel analysis of pooled samples. Nucleic Acids Research, 38(13): e142 (2010).

Song, et al. Reactions in droplets in microfluidic channels. Angew Chem Int Ed Engl. Nov. 13, 2006;45(44):7336-56.

Thaxton, C.S. et al. "A Bio-Bar-Code Assay Based Upon Dithiothreitol Oligonucleotide Release" Anal Chem (2005) 77:8174-8178.

Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.

Thorsen, et al. Dynamic pattern formation in a vesicle-generating microfluidic device. Physical Review Letters. American Physical Society. 2001; 86(18):4163-4166.

Tonelli, et al. Perfluoropolyether functional oligomers: unusual reactivity in organic chemistry. Journal of fluorine chemistry. 2002; 118(1)107-121.

Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

Turner, et al. Assaying chromosomal inversions by single-molecule haplotyping. Nat Methods. Jun. 2006;3(6):439-45.

Turner, et al, "High-throughput haplotype determination over long distances by haplotype fusion PCR and ligation haplotyping", Nat Protoc., 4:1771-83, 2009.

Uttamapinant, et al. Fast, cell-compatible click chemistry with copper-chelating azides for biomolecular labeling. Angew. Chem. Int. End. Engl., Jun. 11, 2012: 51(24) pp. 5852-5856.

Vitak, et al. Sequencing thousands of single-cell genomes with combinatorial indexing.Nature methods 14.3 (2017): 302-308.

Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.

Wang, et al. Efficient and unique cobarcoding of second-generation sequencing reads from long DNA molecules enabling cost-effective and accurate sequencing, haplotyping, and de novo assembly. Genome Research 29.5 (2019): 798-808.

Weigl, et al. Microfluidic Diffusion-Based Separation and Detection. Science. 1999; pp. 346-347.

Williams, et al. Amplification of complex gene libraries by emulsion PCR. Nature Methods. 2006;3(7):545-50.

Wu, L. et al. "Detection DNA Point Mutation with Rolling-Circle Amplification Chip" Bioinformatics & Biomed Eng Conference (2010) Piscataway, NJ pp. 1-4.

Xi, et al. New library construction method for single-cell genomes. PLoS One. Jul. 19, 2017;12(7):e0181163. doi: 10.1371/journal.pone.0181163. eCollection 2017.

Xiao, et al., "Determination of haplotypes from single DNA molecules: a method for single-molecule barcoding", Hum Mutat., 28:913-21, 2007.

Zhang et al., Archaeal RNA ligase from thermoccocus kodakarensis for template dependent ligation, RNA Biology 2017, vol. 14, No. 1, 36-44, Epublished: Oct. 7, 2016.

Zhang, et al. One-step fabrication of supramolecular microcapsules from microfluidic droplets. Science. Feb. 10, 2012;335(6069):690-4. doi: 10.1126/science.1215416.

Zheng, et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

(56) References Cited

OTHER PUBLICATIONS

Zhu, et al. Reverse transcriptase template switching: a SMART approach for full-length cDNA library construction. Biotechniques. Apr. 2001;30(4):892-7.

Zilionis et al. Single-cell barcoding and sequencing using droplet microfluidics, Nature Protocols, 12(1) 2017:44.

Co-pending PCT application No. PCT/US2022/017558, inventors Dagmar et al., filed on Feb. 23, 2022.

Co-pending PCT application No. PCT/US2022/017377, inventors Pfeiffer et al., filed on Feb. 22, 2022.

Co-pending U.S. Appl. No. 17/318,364, inventors Bava; Felice Alessio et al., filed May 12, 2021.

Co-pending U.S. Appl. No. 17/480,724, inventors Martinez; Luigi Jhon Alvarado et al., filed Sep. 21, 2021.

Co-pending U.S. Appl. No. 17/517,408, inventors Salmanzadeh; Alireza et al., filed Nov. 2, 2021.

Co-pending U.S. Appl. No. 17/518,213, inventor Lund; Paul Eugene, filed Nov. 3, 2021.

Co-pending U.S. Appl. No. 17/538,783, inventors Hindson; Benjamin et al., filed Nov. 30, 2021.

Co-pending U.S. Appl. No. 17/580,947, inventor Gibbons; Michael, filed Jan. 21, 2022.

Co-pending U.S. Appl. No. 17/831,835, inventor Martinez; Luigi Jhon Alvarado, filed Jun. 3, 2022.

Co-pending U.S. Appl. No. 17/957,781, inventor Bava; Felice Alessio, filed Sep. 30, 2022.

Co-pending U.S. Appl. No. 18/046,843, inventor Toh; Mckenzi, filed Oct. 14, 2022.

Co-pending U.S. Appl. No. 18/061,914, inventors Mikkelsen; Tarjei Sigurd et al., filed Dec. 5, 2022.

\* cited by examiner

A)

B)

C)

D)

E)

METHODS AND SYSTEMS FOR CHARACTERIZING ANALYTES FROM INDIVIDUAL CELLS OR CELL POPULATIONS

CROSS-REFERENCE

This application is a continuation application of U.S. application Ser. No. 17/229,557, filed Apr. 13, 2021, which is a continuation application of U.S. application Ser. No. 16/554,564, filed Aug. 28, 2019, which is a continuation in part application of International Application No. PCT/US2019/019309, filed Feb. 22, 2019, which claims benefit of U.S. Provisional Patent Application Nos. 62/633,982, filed Feb. 22, 2018 and 62/804,648, filed Feb. 12, 2019.

BACKGROUND

Samples may be processed for various purposes, such as identification of a type of moiety within the sample. The sample may be a biological sample. The biological samples may be processed for various purposes, such as detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Partitions and/or biological samples in partitions may be subjected to various processes, such as chemical processes or physical processes. Partitions and/or samples in partitions may be subjected to heating or cooling, or chemical reactions, such as to yield species that may be qualitatively or quantitatively processed.

SUMMARY

The present disclosure provides methods for use in various sample processing and analysis applications. The methods provided herein may involve hybridizing a probe to a target region of a nucleic acid molecule of interest, barcoding the resultant complex, and performing an extension, denaturation, and amplification processes to provide nucleic acid molecules comprising a sequence the same or substantially the same as or complementary to that of the target region of the nucleic acid molecule of interest. A method may comprise hybridizing a first probe and a second probe to first and second target regions of the nucleic acid molecule, linking the first and second probes to provide a probe-linked nucleic acid molecule, and barcoding the probe-linked nucleic acid molecule. One or more processes of the methods provided herein may be performed within a partition such as a droplet or well. The methods of the present disclosure may obviate the need for reverse transcription during analysis of ribonucleic acid molecules and may be useful, for example, in controlled analysis and processing of analytes such as biological particles, nucleic acids, and proteins.

In an aspect, provided herein is a method of analyzing a sample comprising a nucleic acid molecule, comprising: (a) providing: (i) a sample comprising the nucleic acid molecule, wherein the nucleic acid molecule comprises a first target region and a second target region, wherein the first target region is adjacent to the second target region; (ii) a first probe comprising a first probe sequence and a second probe sequence, wherein the first probe sequence of the first probe is complementary to the first target region of the nucleic acid molecule, and wherein the first probe sequence comprises a first reactive moiety; and (iii) a second probe comprising a third probe sequence, wherein the third probe sequence of the second probe is complementary to the second target region of the nucleic acid molecule, and wherein the third probe sequence comprises a second reactive moiety; (b) subjecting the sample to conditions sufficient to (i) hybridize the first probe sequence of the first probe to the first target region of the nucleic acid molecule, and (ii) hybridize the third probe sequence of the second probe to the second target region of the nucleic acid molecule, such that the first reactive moiety of the first probe sequence of the first probe is adjacent to the second reactive moiety of the third probe sequence of the second probe; (c) subjecting the first reactive moiety and the second reactive moiety to conditions sufficient to yield a probe-linked nucleic acid molecule comprising the first probe linked to the second probe; and (d) with the probe-linked nucleic acid molecule in a partition, barcoding the probe-linked nucleic acid molecule to provide a barcoded probe-linked nucleic acid molecule.

In some embodiments, the partition is a well. In some embodiments the partition is a droplet. In some embodiments, (d) comprises (i) providing, in the partition, a nucleic acid barcode molecule comprising a binding sequence and a barcode sequence, wherein the binding sequence is complementary to the second probe sequence of the first probe, and (ii) hybridizing the binding sequence to the second probe sequence in the partition. In some embodiments, the nucleic acid barcode molecule further comprises an additional binding sequence. In some cases, the binding sequence is hybridized to the second probe sequence in a partition among a plurality of partitions. In some embodiments, subsequent to (c), the probe-linked nucleic acid molecule is co-partitioned with the nucleic acid barcode molecule. In some embodiments, subsequent to (a), the nucleic acid molecule is co-partitioned with the first probe, the second probe, and the nucleic acid barcode molecule. In some embodiments, (b) and (c) are performed in the partition. In some embodiments, the method further comprises subjecting the partition to conditions sufficient to conduct an amplification reaction using the barcoded probe-linked nucleic acid molecule, thereby generating an amplification product within the partition. In some embodiments, the amplification reaction is a polymerase chain reaction. In some embodiments, the method further comprises releasing the amplification product from the partition. In some embodiments, the method further comprises sequencing the amplification product.

In some embodiments, the second probe comprises a fourth probe sequence, and wherein (d) further comprises providing, in the partition, a nucleic acid binding molecule, wherein the nucleic acid binding molecule comprises a second binding sequence that is complementary to the fourth probe sequence of the second probe. In some embodiments, the nucleic acid binding molecule further comprises a third binding sequence. In some embodiments, the nucleic acid binding molecule further comprises a second barcode sequence. In some embodiments, the method further comprises hybridizing the second binding sequence to the fourth probe sequence of the second probe in the partition.

In some embodiments, the nucleic acid barcode molecule is attached to a bead. In some embodiments, the bead is a gel bead. In some embodiments, the bead comprises a plurality of nucleic acid barcode molecules attached thereto, wherein the plurality of nucleic acid barcode molecules comprise the nucleic acid barcode molecule. In some embodiments, the bead comprises at least 10,000 nucleic acid barcode molecules attached thereto. In some embodiments, the bead comprises at least 100,000 nucleic acid barcode molecules attached thereto. In some embodiments, the bead comprises at least 1,000,000 nucleic acid barcode molecules attached thereto. In some embodiments, the bead comprises at least 10,000,000 nucleic acid barcode molecules attached thereto. In some embodiments, the plurality of nucleic acid barcode molecules are releasably attached to the bead. In some embodiments, the plurality of nucleic acid barcode molecules are releasable from the bead upon application of a stimulus. In some embodiments, the stimulus is selected from the group consisting of a thermal stimulus, a photo stimulus, and a chemical stimulus. In some embodiments, the stimulus is a reducing agent. In some embodiments, the stimulus is dithiothreitol.

In some embodiments, the application of the stimulus results in one or more of (i) cleavage of a linkage between nucleic acid barcode molecules of the plurality of nucleic acid barcode molecules and the bead, and (ii) degradation of the bead to release nucleic acid barcode molecules of the plurality of nucleic acid barcode molecules from the bead. In some embodiments, (d) comprises (i) providing, in the partition, the nucleic acid barcode molecule releasably attached to the bead, wherein the nucleic acid barcode molecule comprises the binding sequence and the barcode sequence; (ii) releasing the nucleic acid barcode molecule from the bead; and (iii) hybridizing the binding sequence of the released nucleic acid barcode molecule to the second probe sequence in the partition.

In some embodiments, the first probe further comprises a barcode sequence or unique molecular identifier. In some embodiments, the second probe further comprises a barcode sequence or a unique molecular identifier.

In some embodiments, the first reactive moiety of the first probe comprises an azide moiety. In some embodiments, the second reactive moiety of the second probe comprises an alkyne moiety. In some embodiments, the first probe is linked to the second probe in the probe-linked nucleic acid molecule via a linker, wherein the linker comprises a triazole moiety.

In some embodiments, the first reactive moiety of the first probe comprises a phosphorothioate moiety. In some embodiments, the second reactive moiety of the second probe comprises an iodide moiety. In some embodiments, the first probe is linked to the second probe in the probe-linked nucleic acid molecule via a linker, wherein the linker comprises a phosphorothioate bond.

In some embodiments, the first reactive moiety of the first probe comprises an amine moiety. In some embodiments, the second reactive moiety of the second probe comprises a phosphate moiety. In some embodiments, the first probe is linked to the second probe in the probe-linked nucleic acid molecule via a linker, wherein the linker comprises a phosphoramidate bond.

In some embodiments, the first reactive moiety of the first probe comprises an amine moiety. In some embodiments, the second reactive moiety of the second probe comprises a phosphate moiety. In some embodiments, the first probe is linked to the second probe in the probe-linked nucleic acid molecule via a linker, wherein the linker comprises a phosphoramidate bond. In some embodiments, the sample comprises a cell, and wherein the nucleic acid molecule is contained within the cell. In some embodiments, the method further comprises, subsequent to (a), permeabilizing the cell, thereby providing access to the nucleic acid molecule. The cell may be alive or dead (e.g., fixed). In some embodiments, the method further comprises, subsequent to (a), lysing the cell, thereby releasing the nucleic acid molecule from the cell. In some embodiments the cell is a prokaryotic cell. In some embodiments, the cell is a eukaryotic cell. In some embodiments, the cell is a lymphocyte. In some embodiments, the cell is a B cell. In some embodiments, the cell is a T cell. In some embodiments, the cell is a human cell. In some embodiments, the cell is provided within the partition.

In some embodiments, the nucleic acid molecule is a single-stranded nucleic acid molecule. In some embodiments, the nucleic acid molecule comprises a polyA sequence at a terminus of the nucleic acid molecule. In some embodiments, the nucleic acid molecule comprises an untranslated region (UTR). In some embodiments, the nucleic acid molecule comprises a 5' cap structure. In some embodiments, the nucleic acid molecule is a ribonucleic acid (RNA) molecule. In some embodiments, the nucleic acid molecule is a messenger RNA (mRNA) molecule.

In some embodiments, the nucleic acid molecule is a deoxyribonucleic acid (DNA) molecule.

In some embodiments, the partition further comprises one or more reagents selected from the group consisting of fluorophores, oligonucleotides, primers, nucleic acid barcode molecules, barcodes, buffers, deoxynucleotide triphosphates, DNA splints, detergents, reducing agents, chelating agents, oxidizing agents, nanoparticles, antibodies, and enzymes.

In some embodiments, the partition further comprises one or more reagents selected from the group consisting of temperature-sensitive enzymes, pH-sensitive enzymes, light-sensitive enzymes, proteases, ligase, polymerases, restriction enzymes, nucleases, protease inhibitors, and nuclease inhibitors.

In some embodiments, the sample comprises a cell bead, and wherein the nucleic acid molecule is contained within the cell bead.

In some embodiments, (a)-(c) are performed without reverse transcription.

In some embodiments, the first probe and the second probe are parts of the same nucleic acid molecule.

In another aspect, provided herein is a method of analyzing a sample comprising a nucleic acid molecule, comprising: (a) providing: (i) a sample comprising the nucleic acid molecule, wherein the nucleic acid molecule comprises a first target region, a gap region, and a second target region, wherein the gap region is disposed between the first target region and the second target region; (ii) a first probe comprising a first probe sequence and a second probe sequence, wherein the first probe sequence of the first probe is complementary to the first target region of the nucleic acid molecule; and (iii) a second probe comprising a third probe sequence, wherein the third probe sequence of the second probe is complementary to the second target region of the nucleic acid molecule; (b) subjecting the sample to conditions sufficient to (i) hybridize the first probe sequence of the first probe to the first target region of the nucleic acid molecule, (ii) hybridize the third probe sequence of the second probe to the second target region of the nucleic acid molecule, and (iii) yield a probe-linked nucleic acid molecule comprising the first probe linked to the second probe; and (c) with the probe-linked nucleic acid molecule in a partition, barcoding the probe-linked nucleic acid molecule to provide a barcoded probe-linked nucleic acid molecule.

In some embodiments, the partition is a well. In some embodiments, the partition is a droplet.

In some embodiments, (b) comprises performing a nucleic acid reaction. In some embodiments, (b) comprises performing an enzymatic ligation reaction or an extension reaction. In some embodiments, (b) comprises performing the extension reaction and the enzymatic ligation reaction. In some embodiments, the nucleic acid reaction comprises using an enzyme selected from the group consisting of T4 RNL2, KOD ligase, SplintR, PBCV1, DNA polymerase, and Mu polymerase, or a derivative thereof. In some embodiments, the gap region comprises a length of at least one base.

In some embodiments, (c) comprises (i) providing, in the partition, a nucleic acid barcode molecule comprising a binding sequence and a barcode sequence, wherein the binding sequence is complementary to the second probe sequence of the first probe, and (ii) hybridizing the binding sequence to the second probe sequence in the partition. In some embodiments, the nucleic acid barcode molecule further comprises an additional binding sequence. In some embodiments, the binding sequence is hybridized to the second probe sequence in a partition among a plurality of partitions.

In some embodiments, the method further comprises, subsequent to (b), co-partitioning the probe-linked nucleic acid molecule and the nucleic acid barcode molecule. In some embodiments, subsequent to (a), the nucleic acid molecule is co-partitioned with the first probe, the second probe, and the nucleic acid barcode molecule. In some embodiments, (b) is performed in the partition. In some embodiments, the method further comprises subjecting the partition to conditions sufficient to conduct an amplification reaction using the barcoded probe-linked nucleic acid molecule, thereby generating an amplification product within the partition. In some embodiments, the amplification reaction is a polymerase chain reaction. In some embodiments, the method further comprises releasing the amplification product from the partition. In some embodiments, the method further comprises sequencing the amplification product. In some embodiments, the second probe comprises a fourth probe sequence, and wherein (d) further comprises providing, in the partition, a nucleic acid binding molecule, wherein the nucleic acid binding molecule comprises a second binding sequence that is complementary to the fourth probe sequence of the second probe.

In some embodiments, the nucleic acid binding molecule further comprises a third binding sequence. In some embodiments, the nucleic acid binding molecule further comprises a second barcode sequence. In some embodiments, the method further comprises hybridizing the second binding sequence to the fourth probe sequence of the second probe in the partition. In some embodiments, the nucleic acid barcode molecule is attached to a bead. In some embodiments, the bead is a gel bead. In some embodiments, the bead comprises a plurality of nucleic acid barcode molecules attached thereto, wherein the plurality of nucleic acid barcode molecules comprise the nucleic acid barcode molecule. In some embodiments, the bead comprises at least 10,000 nucleic acid barcode molecules attached thereto. In some embodiments, the bead comprises at least 100,000 nucleic acid barcode molecules attached thereto. In some embodiments, the bead comprises at least 1,000,000 nucleic acid barcode molecules attached thereto. In some embodiments, the bead comprises at least 10,000,000 nucleic acid barcode molecules attached thereto. In some embodiments, the plurality of nucleic acid barcode molecules are releasably attached to the bead. In some embodiments, the plurality of nucleic acid barcode molecules are releasable from the bead upon application of a stimulus. In some embodiments, the stimulus is selected from the group consisting of a thermal stimulus, a photo stimulus, and a chemical stimulus. In some embodiments, the stimulus is a reducing agent. In some embodiments, the stimulus is dithiothreitol.

In some embodiments, the application of the stimulus results in one or more of (i) cleavage of a linkage between nucleic acid barcode molecules of the plurality of nucleic acid barcode molecules and the bead, and (ii) degradation of the bead to release nucleic acid barcode molecules of the plurality of nucleic acid barcode molecules from the bead.

In some embodiments, (c) comprises (i) providing, in the partition, the nucleic acid barcode molecule releasably attached to the bead, wherein the nucleic acid barcode molecule comprises the binding sequence and the barcode sequence; (ii) releasing the nucleic acid barcode molecule from the bead; and (iii) hybridizing the binding sequence of the released nucleic acid barcode molecule to the second probe sequence in the partition. In some embodiments, the first probe further comprises a barcode sequence or unique molecular identifier. In some embodiments, the second probe further comprises a barcode sequence or a unique molecular identifier. In some embodiments, the sample comprises a cell, and wherein the nucleic acid molecule is contained within the cell. In some embodiments, the method further comprises, subsequent to (a), permeabilizing the cell, thereby providing access to the nucleic acid molecule. In some embodiments, the method further comprises, subsequent to (a), lysing the cell, thereby releasing the nucleic acid molecule from the cell.

In some embodiments, the cell is a prokaryotic cell. In some embodiments, the cell is a eukaryotic cell. In some embodiments, the cell is a lymphocyte. In some embodiments, the cell is a B cell. In some embodiments, the cell is a T cell. In some embodiments, the cell is a human cell. In some embodiments, the cell is provided within the partition. In some embodiments, the nucleic acid molecule is a single-stranded nucleic acid molecule. In some embodiments, the nucleic acid molecule comprises a polyA sequence at a terminus of the nucleic acid molecule.

In some embodiments, the nucleic acid molecule comprises an untranslated region (UTR). In some embodiments, the nucleic acid molecule comprises a 5' cap structure. In some embodiments, the nucleic acid molecule is a ribonucleic acid (RNA) molecule. In some embodiments, the nucleic acid molecule is a messenger RNA (mRNA) molecule. In some embodiments, the nucleic acid molecule is a deoxyribonucleic acid (DNA) molecule.

In some embodiments, the partition further comprises one or more reagents selected from the group consisting of fluorophores, oligonucleotides, primers, nucleic acid barcode molecules, barcodes, buffers, deoxynucleotide triphosphates, ribonucleoside triphosphates, DNA splints, detergents, reducing agents, chelating agents, oxidizing agents, nanoparticles, antibodies, and enzymes.

In some embodiments, the partition further comprises one or more reagents selected from the group consisting of temperature-sensitive enzymes, pH-sensitive enzymes, light-sensitive enzymes, proteases, ligase, polymerases, restriction enzymes, nucleases, protease inhibitors, and nuclease inhibitors.

In some embodiments, the sample comprises a cell bead, and the nucleic acid molecule is contained within the cell bead. In some embodiments, (b) is performed without reverse transcription.

In some embodiments, the first probe or the second probe comprises a known sequence.

In some embodiments, the first probe or the second probe comprises a degenerate sequence.

In some embodiments, the first probe or the second probe comprises a Phi-29 based rolling circle amplification sequence.

In another aspect, provided herein is a method of analyzing a sample comprising a nucleic acid molecule, comprising: (a) providing: (i) a sample comprising the nucleic acid molecule, wherein the nucleic acid molecule comprises a target region; (ii) a probe comprising a probe sequence and an adapter sequence, wherein the probe sequence is complementary to the target region; and (iii) an adapter comprising a binding sequence, wherein the binding sequence is complementary to the adapter sequence; (b) subjecting the sample to conditions sufficient to (i) hybridize the probe sequence of the probe to the target region, and (ii) hybridize the adapter sequence of the probe to the binding sequence of the adapter, to yield an adapter-bound probe; and (c) with the adapter-bound probe in a partition, barcoding the adapter-bound probe to provide a barcoded nucleic acid molecule.

In some embodiments, the adapter sequence comprises between 5 to 10 nucleotides.

In another aspect, the present disclosure provides a method of analyzing a sample comprising a nucleic acid molecule, comprising: (a) providing: (i) a sample comprising the nucleic acid molecule, wherein the nucleic acid molecule comprises a first target region, a gap region, and a second target region, wherein the gap region is disposed between the first target region and the second target region; (ii) a first probe comprising a first probe sequence and a second probe sequence, wherein the first probe sequence of the first probe is complementary to the first target region of the nucleic acid molecule; and (iii) a second probe comprising a third probe sequence, wherein the third probe sequence of the second probe is complementary to the second target region of the nucleic acid molecule; (b) subjecting the sample to conditions sufficient to (i) hybridize the first probe sequence of the first probe to the first target region of the nucleic acid molecule, (ii) hybridize the third probe sequence of the second probe to the second target region of the nucleic acid molecule, and (iii) yield a probe-linked nucleic acid molecule comprising the first probe linked to the second probe; and (d) with the probe-linked nucleic acid molecule in a partition, barcoding the probe-linked nucleic acid molecule to provide a barcoded probe-linked nucleic acid molecule.

In another aspect, the present disclosure provides a method of analyzing a sample comprising a nucleic acid molecule, comprising: (a) providing: (i) a sample comprising said nucleic acid molecule, wherein said nucleic acid molecule comprises a first target region and a second target region, wherein said first target region and said second target region are disposed on a same strand of said nucleic acid molecule; (ii) a first probe comprising a first probe sequence and a second probe sequence, wherein said first probe sequence of said first probe is complementary to said first target region of said nucleic acid molecule; and (iii) a second probe comprising a third probe sequence, wherein said third probe sequence of said second probe is complementary to said second target region of said nucleic acid molecule; (b) subjecting said sample to conditions sufficient to (i) hybridize said first probe sequence of said first probe to said first target region of said nucleic acid molecule, and (ii) hybridize said third probe sequence of said second probe to said second target region of said nucleic acid molecule to yield a probe-associated nucleic acid molecule; (c) subjecting said probe-associated nucleic acid molecule to conditions sufficient to yield a probe-linked nucleic acid molecule comprising said first probe linked to said second probe; and (d) within a partition, attaching a barcode sequence to said probe-linked nucleic acid molecule.

In some embodiments, said partition is a well among a plurality of wells.

In some embodiments, said partition is a droplet among a plurality of droplets.

In some embodiments, (d) comprises (i) providing, in said partition, a nucleic acid barcode molecule comprising a binding sequence and a barcode sequence, wherein said binding sequence is complementary to said second probe sequence of said first probe, and (ii) subjecting said partition to conditions sufficient to hybridize said binding sequence to said second probe sequence. In some embodiments, the method further comprises subjecting said partition to conditions sufficient to conduct a nucleic acid extension reaction to generate a barcoded nucleic acid molecule comprising a sequence corresponding to said first probe, a sequence corresponding to said second probe, and a sequence corresponding to said barcode sequence. In some embodiments, the method further comprises subjecting said partition to conditions sufficient to ligate said probe-linked nucleic acid molecule to said nucleic acid barcode molecule to generate a barcoded nucleic acid molecule comprising a sequence corresponding to said first probe, a sequence corresponding to said second probe, and a sequence corresponding to said barcode sequence. In some embodiments, the method further comprises subjecting said barcoded nucleic acid molecule to conditions sufficient to conduct an amplification reaction to generate an amplification product, which amplification product comprises nucleic acid molecules comprising said sequence corresponding to said first probe, said sequence corresponding to said second probe, and said sequence corresponding to said barcode sequence. In some embodiments, the amplification reaction comprises use of a primer comprising one or more functional sequences and wherein said amplification product comprises nucleic acid molecules further comprising said one or more functional sequences. In some embodiments, said amplification is isothermal amplification. In some embodiments, said amplification reaction is performed within said partition. In some embodiments, the method further comprises recovering said amplification product from said partition. In some embodiments, said amplification reaction is performed outside of said partition. In some embodiments, the method further comprises sequencing said amplification product or a derivative thereof.

In some embodiments, the method further comprises (i) providing a splint oligonucleotide comprising a first sequence complementary to said second probe sequence and a second sequence, and (ii) subjecting said partition to conditions sufficient to hybridize said first sequence of said splint oligonucleotide to said second probe sequence. In some embodiments, said first sequence of said splint oligonucleotide hybridizes to said second probe sequence prior to (c). In some embodiments, said first sequence of said splint oligonucleotide hybridizes to said second probe sequence after (c). In some embodiments, (d) comprises (i) providing, in said partition, a nucleic acid barcode molecule comprising a binding sequence and a barcode sequence, wherein said binding sequence is complementary to said second sequence of said splint oligonucleotide, and (ii) subjecting said partition to conditions sufficient to hybridize said binding sequence to said second sequence of said splint oligonucleotide. In some embodiments, said binding sequence of said nucleic acid barcode molecule comprises one or more ribobases. In some embodiments, said method further comprises subjecting (i) said splint oligonucleotide hybridized to said second probe sequence and (ii) said nucleic acid barcode molecule to conditions sufficient to ligate said probe-linked nucleic acid molecule to said nucleic acid barcode molecule. In some embodiments, said method further comprises subjecting (i) said splint oligonucleotide hybridized to said second probe sequence and (ii) said nucleic acid barcode molecule to conditions sufficient to conduct a nucleic acid extension reaction to generate a barcoded nucleic acid molecule comprising a sequence corresponding to said first probe, a sequence corresponding to said second probe, and a sequence corresponding to said barcode sequence. In some embodiments, said method further comprises subjecting said barcoded nucleic acid molecule to conditions sufficient to conduct an amplification reaction to generate an amplification product, which amplification product comprises nucleic acid molecules comprising said sequence corresponding to said first probe, said sequence corresponding to said second probe, and said sequence corresponding to said barcode sequence. In some embodiments, said amplification reaction is a polymerase chain reaction. In some embodiments, said amplification reaction is performed within said partition. In some embodiments, said method further comprises recovering said amplification product from said partition. In some embodiments, said amplification reaction is performed outside of said partition. In some embodiments, said amplification reaction is isothermal amplification. In some embodiments, the method further comprises sequencing said amplification product or derivative thereof.

In some embodiments, said nucleic acid barcode molecule further comprises a unique molecular identifier sequence, a sequencing primer sequence, and/or a partial sequencing primer sequence. In some embodiments, subsequent to (c), said probe-associated nucleic acid molecule is co-partitioned with said nucleic acid barcode molecule. In some embodiments, subsequent to (a), said nucleic acid molecule is co-partitioned with said first probe, said second probe, and said nucleic acid barcode molecule. In some embodiments, (c) is performed within said partition. In some embodiments, (b) and (c) are performed within said partition.

In some embodiments, said second probe comprises a fourth probe sequence, and wherein said method further comprises providing a nucleic acid binding molecule in said partition, wherein said nucleic acid binding molecule comprises a second binding sequence that is complementary to said fourth probe sequence of said second probe. In some embodiments, the method further comprises hybridizing said second binding sequence to said fourth probe sequence of said second probe within said partition.

In some embodiments, said nucleic acid barcode molecule is coupled to a bead. In some embodiments, said bead is a gel bead. In some embodiments, said nucleic acid barcode molecule is coupled to said bead via a labile moiety. In some embodiments, said bead comprises a plurality of nucleic acid barcode molecules coupled thereto, wherein said plurality of nucleic acid barcode molecules comprise said nucleic acid barcode molecule. In some embodiments, said bead comprises at least 100,000 nucleic acid barcode molecules coupled thereto. In some embodiments, said plurality of nucleic acid barcode molecules are releasably coupled to said bead. In some embodiments, said plurality of nucleic acid barcode molecules are releasable from said bead upon application of a stimulus. In some embodiments, said stimulus is selected from the group consisting of a thermal stimulus, a photo stimulus, a biological stimulus, and a chemical stimulus. In some embodiments, said stimulus is a reducing agent. In some embodiments, the application of said stimulus results in one or more of (i) cleavage of a linkage between nucleic acid barcode molecules of said plurality of nucleic acid barcode molecules and said bead, and (ii) degradation of said bead to release nucleic acid barcode molecules of said plurality of nucleic acid barcode molecules from said bead. In some embodiments, said bead is provided in said partition, and wherein said nucleic acid barcode molecule is released from said bead within said partition.

In some embodiments, (c) is performed before (d). In some embodiments, (d) is performed before (c).

In some embodiments, said first probe or said second probe further comprises a barcode sequence or unique molecular identifier.

In some embodiments, said second probe comprises a fourth probe sequence, which fourth probe sequence hybridizes to a third target region of said nucleic acid molecule. In some embodiments, said second target region is not adjacent to said third target region, and wherein said third probe sequence and said fourth probe sequence of said second probe are separated by a linker sequence.

In some embodiments, said first probe sequence of said first probe comprises a first reactive moiety and said third probe sequence of said second probe comprises a second reactive moiety, wherein, subsequent to (b), said first reactive moiety is adjacent to said second reactive moiety. In some embodiments, wherein (c) comprises subjecting said first reactive moiety and said second reactive moiety to conditions sufficient to link said first probe sequence to said third probe sequence. In some embodiments, said first reactive moiety of said first probe or said second reactive moiety of said second probe comprises an azide moiety, an alkyne moiety, a phosphorothioate moiety, an iodide moiety, an amine moiety, or a phosphate moiety. In some embodiments, said first probe is linked to said second probe in said probe-linked nucleic acid molecule via a linker, wherein said linker comprises a triazole moiety, a phosphorothioate bond, or a phosphoroamidatephosphoramidate bond.

In some embodiments, (c) comprises performing an enzymatic ligation reaction and/or an extension reaction. In some embodiments, said enzymatic ligation reaction and/or said extension reaction comprises use of an enzyme selected from the group consisting of T4 RNL2, SplintR, T4 DNA ligase, KOD ligase, PBCV1, DNA polymerase, and Mu polymerase, or a derivative thereof. In some embodiments, prior to (a), said first probe is linked to said second probe via one or more linking sequences. In some embodiments, said one or more linking sequences comprise one or more of a spacer sequence, a sequencing primer or complement thereof, a capture sequence, a restriction site, a transposition site, and a unique molecular identifier sequence. In some embodiments, said one or more linking sequences comprise a thermolabile, photocleavable, or enzymatically cleavable site.

In some embodiments, said first target region is adjacent to said second target region.

In some embodiments, said first target region and said second target region are separated by a gap region disposed between said first target region and said second target region. In some embodiments, said gap region is at least one nucleotide long. In some embodiments, said gap region is at least 10 nucleotides long. In some embodiments, said gap region is at least 100 nucleotides long.

In some embodiments, the method further comprises digesting one or more nucleic acid molecules or portions thereof using an exonuclease.

In some embodiments, said first probe or said second probe comprises a known sequence or a degenerate sequence.

In some embodiments, said first probe or said second probe comprises a Phi-29 based rolling circle amplification sequence. In some embodiments, said first probe or said second probe comprises a cleavable site, wherein said cleavable site is cleavable using a thermal, photo-, chemical, or biological stimulus. In some embodiments, the method further comprises contacting said first probe or said second probe with a transposase.

In some embodiments, said sample comprises a cell, and wherein said nucleic acid molecule is contained within said cell. In some embodiments, the method further comprises, subsequent to (a), lysing or permeabilizing said cell, thereby providing access to said nucleic acid molecule. In some embodiments, said cell is a prokaryotic cell. In some embodiments, said cell is a eukaryotic cell. In some embodiments, said cell is a human cell. In some embodiments, said cell is a fixed suspension cell or a formalin-fixed paraffin-embedded cell. In some embodiments, said cell is provided within said partition. In some embodiments, said cell is a single cell.

In some embodiments, said nucleic acid molecule is a ribonucleic acid (RNA) molecule. In some embodiments, said nucleic acid molecule is a messenger RNA (mRNA) molecule. In some embodiments, said nucleic acid molecule comprises a poly-A sequence at a terminus of said nucleic acid molecule.

In some embodiments, said nucleic acid molecule is a deoxyribonucleic acid (DNA) molecule.

In some embodiments, said partition further comprises one or more reagents selected from the group consisting of fluorophores, oligonucleotides, primers, nucleic acid barcode molecules, barcodes, buffers, deoxynucleotide triphosphates, DNA splints, detergents, reducing agents, chelating agents, oxidizing agents, nanoparticles, antibodies, temperature-sensitive enzymes, pH-sensitive enzymes, light-sensitive enzymes, proteases, ligases, polymerases, reverse transcriptases, restriction enzymes, nucleases, protease inhibitors, and nuclease inhibitors. In some embodiments, said polymerase is a polymerase selected from the group of DNA polymerase, RNA polymerase, Hot Start polymerase, and Warm start polymerase. In some embodiments, said sample comprises a cell bead, and wherein said nucleic acid molecule is contained within said cell bead. In some embodiments, (a)-(c) are performed without reverse transcription.

In yet another aspect, the present disclosure provides a method of analyzing a sample comprising a nucleic acid molecule, comprising: (a) providing: (i) a sample comprising said nucleic acid molecule, wherein said nucleic acid molecule comprises a target region; (ii) a probe comprising a probe sequence and a binding sequence, wherein said probe sequence is complementary to said target region; and (iii) an adapter comprising a first sequence and a second sequence, wherein said first sequence of said adapter is complementary to said binding sequence of said probe; (b) subjecting said sample to conditions sufficient to hybridize (i) said probe sequence of said probe to said target region, and (ii) said binding sequence of said probe to said first sequence of said adapter, to yield an adapter-bound probe; and (c) within a partition, barcoding said adapter-bound probe to provide a barcoded nucleic acid molecule.

In a further aspect, the present disclosure provides a method of analyzing a sample comprising a nucleic acid molecule, comprising: (a) providing: (i) a sample comprising said nucleic acid molecule, wherein said nucleic acid molecule comprises a target region; (ii) a probe comprising a probe sequence and a first reactive moiety, wherein said probe sequence is complementary to said target region; and (iii) a nucleic acid barcode molecule comprising a second reactive moiety and a barcode sequence; (b) subjecting said sample to conditions sufficient to hybridize said probe sequence of said probe to said target region to provide a probe-associated nucleic acid molecule; and (c) within a partition, subjecting said first reactive moiety of said probe-associated nucleic acid molecule and said second reactive moiety of said nucleic acid barcode molecule to conditions sufficient to link said probe-associated nucleic acid molecule and said nucleic acid barcode molecule to provide a barcoded nucleic acid product.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 13A schematically illustrates a method of using such a probe. Panel 13A illustrates a molecular inversion probe comprising first and second probe ends hybridized to a target nucleic acid molecule. Panel 13B illustrates a circular probe-linked nucleic acid molecule. Panel 13C illustrates cleavage and linearization of the circular probe for barcoding. FIG. 13B illustrates circularization of a first probe and a second probe using a splint molecule.

FIG. 20A schematically shows barcoding of a nucleic acid molecule. Panel 20A illustrates a probe-linked nucleic acid molecule, while Panel 20B illustrates a splint molecule associated with a probe-linked nucleic acid molecule. Panel 20C illustrates a nucleic acid barcode molecule associating with the adapter molecule associated with a probe-linked nucleic acid molecule while Panel 20D illustrates a barcoded probe-linked nucleic acid molecule.

DETAILED DESCRIPTION

Figure 1:
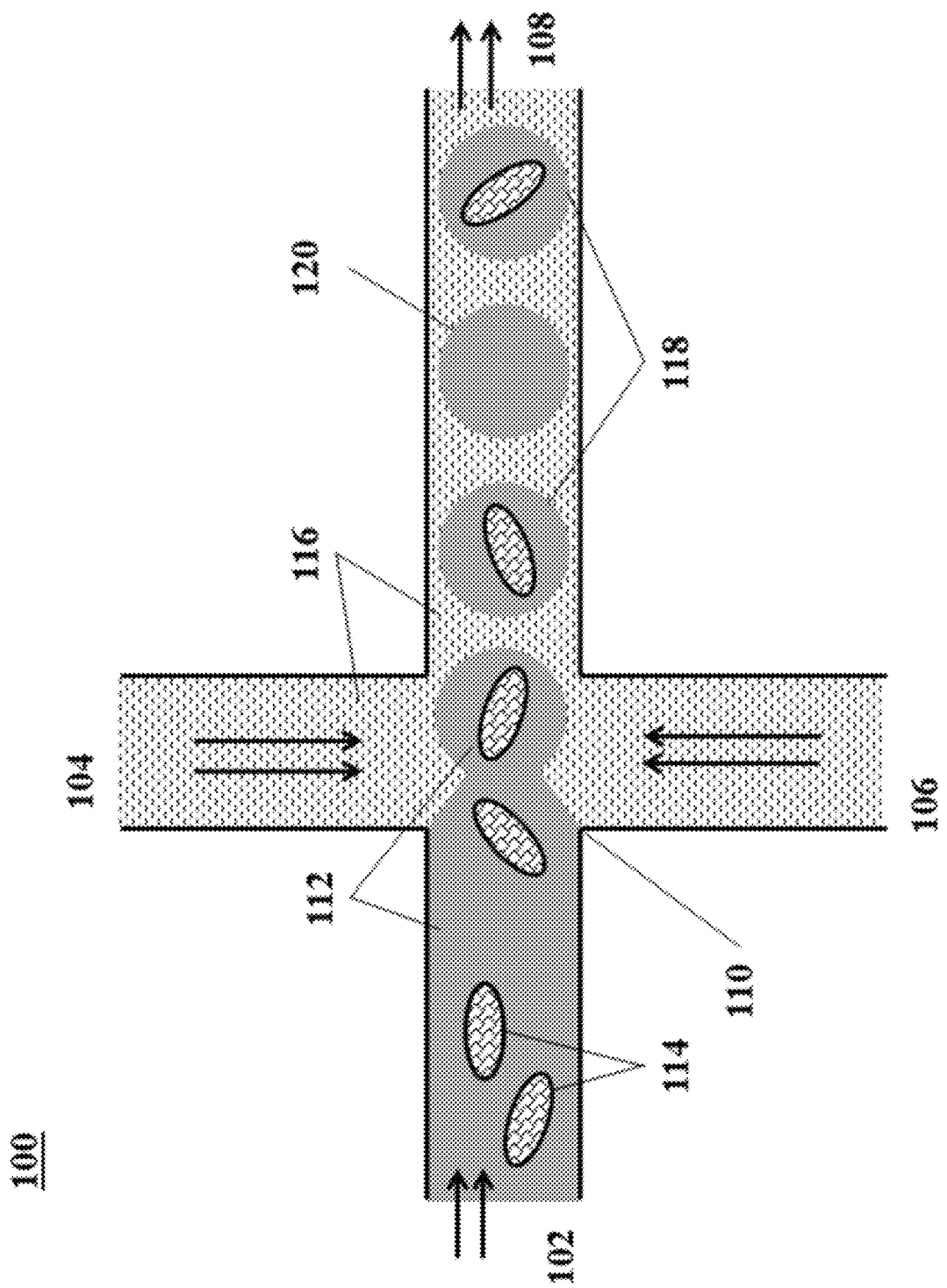
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The terms "barcode nucleic acid molecule" and "nucleic acid barcode molecule" may be used interchangeably herein. A barcode nucleic acid molecule may comprise a barcode. A barcode nucleic acid molecule may also comprise adapters, such as a unique molecular identifier sequence.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. The terms "adapter", "adapter molecule", and "adapter nucleic acid sequence" may also be used interchangeably herein. An adaptor or tag can be coupled to a polynucleotide sequence to be "tagged" by any approach, including ligation, hybridization, or other approaches. An adapter molecule, in some cases, may be any useful nucleic acid sequence and may include, for example, a sequencing primer site, a barcode sequence, a transposition site, a restriction site, a unique molecular identifier, a binding sequence, and any/or derivatives, variations, or combinations thereof.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

A cell bead may include a single cell or a plurality of cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles. In some cases, a cell or a plurality of cells may be alive, and the cells may be subjected to further processing, e.g., cell labeling.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally, refers to a space or volume that may be suitable to contain one or more species or conduct one or more reactions. A partition may be a physical compartment, such as a droplet or well (e.g., a microwell). The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Provided herein are methods that may be used for various sample processing and/or analysis applications. A method of the present disclosure may allow barcoding a nucleic acid molecule (e.g., a ribonucleic acid (RNA) molecule) within a partition without performing reverse transcription. The nucleic acid molecule barcoded may be a targeted nucleic acid molecule. Such a method may involve attaching a probe to the nucleic acid molecule, and subsequently attaching a nucleic acid barcode molecule comprising a barcode sequence to the probe. For example, the nucleic acid barcode molecule may attach to an overhanging sequence of the probe or to the end of the probe. Extension from an end of the probe to an end of the nucleic acid barcode molecule may form an extended nucleic acid molecule comprising both a sequence complementary to the barcode sequence and a sequence complementary to a target region of the nucleic acid molecule. The extended nucleic acid molecule may then be denatured from the nucleic acid barcode molecule and the nucleic acid molecule and duplicated. This method may avoid the use of reverse transcription, which may be highly error prone. One or more processes of the method may be carried out within a partition such as a droplet or well.

The present disclosure also provides a method of processing a sample that provides a barcoded nucleic acid molecule having linked probe molecules attached thereto. The method may comprise one or more ligation-mediated reactions. The method may comprise providing a sample comprising a nucleic acid molecule (e.g., an RNA molecule) having adjacent first and second target regions; a first probe having a first probe sequence that is complementary to the first target region and a second probe sequence; and a second probe having a third probe sequence that is complementary to the second target region. The first and third probe sequences may also comprise first and second reactive moieties, respectively. Upon hybridization of the first probe sequence of the first probe to the first target region of the nucleic acid molecule, and hybridization of the third probe sequence of the second probe to the second target region of the nucleic acid molecule, the reactive moieties may be adjacent to one another. Subsequent reaction between the adjacent reactive moieties under sufficient conditions may link the first and second probes to yield a probe-linked nucleic acid molecule. The probe-linked nucleic acid molecule may also be referred to as a probe-ligated nucleic acid molecule. The probe-linked nucleic acid molecule may then be barcoded with a barcode sequence of a nucleic acid barcode molecule to provide a barcoded probe-linked nucleic acid molecule. Barcoding may be achieved by hybridizing a binding sequence of the nucleic acid barcode molecule to the second probe sequence of the first probe of the probe-linked nucleic acid molecule. The barcoded probe linked-nucleic acid molecule may be subjected to amplification reactions to yield an amplified product comprising the first and second target regions and the barcode sequence or sequences complementary to these sequences. Accordingly, the method may provide amplified products without the use of reverse transcription. One or more processes may be performed within a partition such as a droplet or well.

Further provided herein are methods of processing a sample that provides a barcoded nucleic acid molecule having linked probe molecules attached thereto. The method may comprise one or more nucleic acid reactions. The method may comprise providing a sample comprising a nucleic acid molecule (e.g., an RNA molecule) having first and second target regions on a same strand (e.g., adjacent or non-adjacent target regions); a first probe having a first probe sequence that is complementary to the first target region and a second probe sequence; and a second probe having a third probe sequence that is complementary to the second target region. The third probe sequence may be known or degenerate (i.e., randomly generated). The first and third probe sequences may also comprise first and second reactive moieties, respectively. Where the nucleic acid molecule has non-adjacent first and second target regions, the nucleic acid molecule may comprise one or more gap regions between the first and second target regions. Upon hybridization of the first probe sequence of the first probe to the first target region of the nucleic acid molecule, and the third probe sequence of the second probe to the second target region of the nucleic acid molecule, to yield a probe-associated nucleic acid molecule, the reactive moieties may be adjacent or non-adjacent to one another. Subsequent reaction between the adjacent or non-adjacent probes may generate a probe-linked nucleic acid molecule. The probe-linked nucleic acid molecule may also be referred to herein as a probe-ligated nucleic acid molecule. The probe-linked nucleic acid molecule may then be barcoded with a barcode sequence of a nucleic acid barcode molecule to provide a barcoded probe-linked nucleic acid molecule. Barcoding may be achieved by hybridizing a binding sequence of the nucleic acid barcode molecule to the second probe sequence of the first probe of the probe-linked nucleic acid molecule. Barcoding may also be achieved by hybridizing a binding sequence of a barcode nucleic acid molecule to a nucleic acid adaptor sequence, where the nucleic acid adaptor sequence comprises a binding sequence that can hybridize to one or more nucleic acid probes. The barcoded probe linked-nucleic acid molecule may be subjected to amplification reactions to yield an amplified product comprising the first and second target regions and the barcode sequence or sequences complementary to these sequences. Accordingly, the method may provide amplified products without the use of reverse transcription. One or more processes may be performed within a cell bead and/or a partition, such as a droplet or well.

Methods of Nucleic Acid Analysis

In an aspect, the present disclosure provides a method comprising providing a sample comprising a nucleic acid molecule (e.g., a ribonucleic acid (RNA) molecule) comprising a target region and a probe comprising (i) a first probe sequence complementary to the sequence of the target region of the nucleic acid molecule and (ii) a second probe sequence; attaching (e.g., hybridizing) the first probe sequence of the probe to the target region of the nucleic acid molecule; providing a nucleic acid barcode molecule comprising (i) a first binding sequence that is complementary to the second probe sequence, (ii) a barcode sequence, and (iii) a second binding sequence; attaching (e.g., hybridizing) the first binding sequence of the nucleic acid barcode molecule to the second probe sequence of the probe; extending the probe from an end of the second probe sequence to an end of the second binding sequence of the nucleic acid barcode molecule to form an extended nucleic acid molecule comprising both a sequence complementary to the barcode sequence and a sequence complementary to the target region of the nucleic acid molecule; denaturing the extended nucleic acid molecule from the nucleic acid barcode molecule and the target region of the nucleic acid molecule to regenerate the nucleic acid barcode molecule and the nucleic acid molecule; and duplicating the extended nucleic acid molecule. The extended nucleic acid molecule may be further amplified (e.g., using polymerase chain reactions (PCR) or linear amplification, as described herein) to facilitate the detection of the extended nucleic acid molecule or a complement thereof (e.g., an amplified product) by, e.g., sequencing.

The methods described herein may facilitate gene expression profiling with single cell resolution using, for example, chemical ligation-mediated barcoding, amplification, and sequencing. The methods described herein may allow for gene expression analysis while avoiding the use of specialized imaging equipment and reverse transcription, which may be highly error prone and inefficient. For example, the methods may be used to analyze a pre-determined panel of target genes in a population of single cells in a sensitive and accurate manner. In some cases, the nucleic acid molecule analyzed by the methods described herein may be a fusion gene (e.g., a hybrid gene generated via translocation, interstitial deletion, or chromosomal inversion).

The nucleic acid molecule analyzed by the methods described herein may be a single-stranded or a double-stranded nucleic acid molecule. A double-stranded nucleic acid molecule may be completely or partially denatured to provide access to a target region (e.g., a target sequence) of a strand of the nucleic acid molecule. Denaturation may be achieved by, for example, adjusting the temperature or pH of a solution comprising the nucleic acid molecule; using a chemical agent such as formamide, guanidine, sodium salicylate, dimethyl sulfoxide, propylene glycol, urea, or an alkaline agent (e.g., NaOH); or using mechanical agitation (e.g., centrifuging or vortexing a solution including the nucleic acid molecule).

The nucleic acid molecule may be an RNA molecule. The RNA molecule may be, for example, a transfer RNA (tRNA) molecule, ribosomal RNA (rRNA) molecule, mitochondrial RNA (mtRNA) molecule, messenger RNA (mRNA) molecule, non-coding RNA molecule, synthetic RNA molecule, or another type of RNA molecule. For example, the RNA molecule may be an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be target regions of the nucleic acid molecule.

The nucleic acid molecule (e.g., RNA molecule) may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). For example, the nucleic acid molecule may comprise one or more features selected from the group consisting of a 5' cap structure, an untranslated region (UTR), a Kozak sequence, a Shine-Dalgarno sequence, a coding sequence, and a poly(A) sequence (e.g., a poly(A) tail).

Features of the nucleic acid molecule may have any useful characteristics. A 5' cap structure may comprise one or more nucleoside moieties joined by a linker such as a triphosphate (ppp) linker. A 5' cap structure may comprise naturally occurring nucleoside and/or non-naturally occurring (e.g., modified) nucleosides. For example, a 5' cap structure may comprise a guanine moiety or a modified (e.g., alkylated, reduced, or oxidized) guanine moiety such as a 7-methylguanylate ($m^7G$) cap. Examples of 5' cap structures include, but are not limited to, $m^7GpppG$, $m^7Gpppm^7G$, $m^7GpppA$, $m^7GpppC$, $GpppG$, $m^{2,7}GpppG$, $m^{2,2,7}GpppG$, and anti-reverse cap analogs such as $m^{7,2'Ome}GpppG$, $m^{7,2'd}GpppG$, $m^{7,3'Ome}GpppG$, and $m^{7,3'd}GpppG$. An untranslated region (UTR) may be a 5' UTR or a 3' UTR. A UTR may include any number of nucleotides. For example, a UTR may comprise at least 3, 5, 7, 10, 20, 30, 40, 50, 60, 70, 80, 90, 100, or more nucleotides. In some cases, a UTR may comprise fewer than 20 nucleotides. In other cases, a UTR may comprise at least 100 nucleotides, such as more than 200, 300, 400, 500, 600, 700, 800, 900, or 1000 nucleotides. Similarly, a coding sequence may include any number of nucleotides, such as at least 3, 5, 10, 20, 30, 40, 50, 60, 70, 80, 90, 100, or more nucleotides. A UTR, coding sequence, or other sequence of a nucleic acid molecule may have any nucleotide or base content or arrangement. For example, a sequence of a nucleic acid molecule may comprise any number or concentration of guanine, cytosine, uracil, and adenine bases. A nucleic acid molecule may also include non-naturally occurring (e.g., modified) nucleosides. A modified nucleoside may comprise one or more modifications (e.g., alkylations, hydroxylation, oxidation, or other modification) in its nucleobase and/or sugar moieties.

The nucleic acid molecule may comprise one or more target regions. In some cases, a target region may correspond to a gene or a portion thereof. Each region may have the same or different sequences. For example, the nucleic acid molecule may comprise two target regions having the same sequence located at different positions along a strand of the nucleic acid molecule. Alternatively, the nucleic acid molecule may comprise two or more target regions having different sequences. Different target regions may be interrogated by different probes. Target regions may be located adjacent to one another or may be spatially separated along a strand of the nucleic acid molecule. As used herein with regard to two entities, "adjacent," may mean that the entities directly next to one other (e.g., contiguous) or in proximity to one another. For example, a first target region may be directly next to a second target region (e.g., having no other entity disposed between the first and second target regions) or in proximity to a second target region (e.g., having an intervening sequence or molecule between the first and second target regions). In some cases, a double-stranded nucleic acid molecule may comprise a target region in each strand that may be the same or different. For a nucleic acid molecule comprising multiple target regions, the methods described herein may be performed for one or more target regions at a time. For example, a single target region of the multiple target regions may be analyzed (e.g., as described herein) or two or more target regions may be analyzed at the same time. Analyzing two or more target regions may involve providing two or more probes, where a first probe has a sequence that is complementary to the first target region, a second probe has a sequence that is complementary to the second target region, etc. Each probe may further comprise one or more additional sequences (e.g., additional probe sequences, unique molecular identifiers (UMIs), or other sequences) that are different from one another such that each probe may bind to a different nucleic acid barcode molecule. In another example, where two target regions are non-adjacent, a first target region and a second target region may be separated by one or more gap regions disposed between the first target region and the second target region.

A target region of the nucleic acid molecule may have one or more useful characteristics. For example, a target region may have any useful length, base content, sequence, melting point, or other characteristic. A target region may comprise, for example, at least 10 bases, such as at least 20, 25, 30, 35, 40, 45, 50, 60, 65, 70, 75, 80, 85, 90, 95, 100, 110, 120, 130, 140, 150, 160, 170, 180, 190, 200, 250, 300, 350, 400, 450, 500, or more bases. A target region may have any useful base content and any useful sequence and combination of bases. For example, a target region may comprise one or more adenine, thymine, uracil, cytosine, and/or guanine bases (e.g., natural or canonical bases). A target region may also comprise one or more derivatives or modified versions of a natural or canonical base, such as an oxidized, alkylated (e.g., methylated), hydroxylated, or otherwise modified base. Similarly, a target region may comprise ribose or deoxyribose moieties and phosphate moieties or derivatives or modified versions thereof.

A target region of the nucleic acid molecule may comprise one or more sequences or features, or portions thereof, of the nucleic acid molecule. For example, a target region may comprise all or a portion of a UTR (e.g., a 3' UTR or a 5' UTR), a Kozak sequence, a Shine-Dalgarno sequence, a coding sequence, a polyA sequence, a cap structure, an intron, an exon, or any other sequence or feature of the nucleic acid molecule.

The nucleic acid molecule (e.g., RNA molecule, such as an mRNA molecule) of a sample may be included within a cell. For example, the sample may comprise a cell comprising the nucleic acid molecule. The cell may comprise additional nucleic acid molecules that may be the same as or different from the nucleic acid molecule of interest. In some cases, the sample may comprise a plurality of cells, and each cell may contain one or more nucleic acid molecules. The cell may be, for example, a human cell, an animal cell, or a plant cell. In some cases, the cell may be derived from a tissue or fluid, as described herein. The cell may be a prokaryotic cell or a eukaryotic cell. The cell may be a lymphocyte such as a B cell or T cell.

Access to a nucleic acid molecule included in a cell may be provided by lysing or permeabilizing the cell. Lysing the cell may release the nucleic acid molecule contained therein from the cell. A cell may be lysed using a lysis agent such as a bioactive agent. A bioactive agent useful for lysing a cell may be, for example, an enzyme (e.g., as described herein). An enzyme used to lyse a cell may or may not be capable of carrying out additional functions such as degrading, extending, reverse transcribing, or otherwise altering a nucleic acid molecule. Alternatively, an ionic or non-ionic surfactant such as TritonX-100, Tween 20, sarcosyl, or sodium dodecyl sulfate may be used to lyse a cell. Cell lysis may also be achieved using a cellular disruption method such as an electroporation or a thermal, acoustic, or mechanical disruption method. Alternatively, a cell may be permeabilized to provide access to a nucleic acid molecule included therein. Permeabilization may involve partially or completely dissolving or disrupting a cell membrane or a portion thereof. Permeabilization may be achieved by, for example, contacting a cell membrane with an organic solvent (e.g., methanol) or a detergent such as Triton X-100 or NP-40.

A nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell comprising the nucleic acid molecule or a derivative thereof (e.g., a cell bead) may be partitioned within a partition such as a well or droplet, e.g., as described herein. One or more reagents may be co-partitioned with a nucleic acid molecule or a derivative thereof or a cell comprising the nucleic acid molecule or a derivative thereof. For example, a nucleic acid molecule or a derivative thereof or a cell comprising the nucleic acid molecule or a derivative thereof may be co-partitioned with one or more reagents selected from the group consisting of lysis agents or buffers, permeabilizing agents, enzymes (e.g., enzymes capable of digesting one or more RNA molecules, extending one or more nucleic acid molecules, reverse transcribing an RNA molecule, permeabilizing or lysing a cell, or carrying out other actions), fluorophores, oligonucleotides, primers, probes, barcodes, nucleic acid barcode molecules (e.g., nucleic acid barcode molecules comprising one or more barcode sequences), buffers, deoxynucleotide triphosphates, detergents, reducing agents, chelating agents, oxidizing agents, nanoparticles, beads, and antibodies. In some cases, a nucleic acid molecule or a derivative thereof, or a cell comprising the nucleic acid molecule or a derivative thereof (e.g., a cell bead), may be co-partitioned with one or more reagents selected from the group consisting of temperature-sensitive enzymes, pH-sensitive enzymes, light-sensitive enzymes, reverse transcriptases, proteases, ligase, polymerases, restriction enzymes, nucleases, protease inhibitors, exonucleases, and nuclease inhibitors. For example, a nucleic acid molecule or a derivative thereof or a cell comprising the nucleic acid molecule or a derivative thereof may be co-partitioned with a polymerase and nucleotide molecules. Partitioning a nucleic acid molecule or a derivative thereof or a cell comprising the nucleic acid molecule or a derivative thereof and one or more reagents may comprise flowing a first phase comprising an aqueous fluid, the cell, and the one or more reagents and a second phase comprising a fluid that is immiscible with the aqueous fluid toward a junction. Upon interaction of the first and second phases, a discrete droplet of the first phase comprising the nucleic acid molecule or a derivative thereof or a cell comprising the nucleic acid molecule or a derivative thereof (e.g., a cell bead) and the one or more reagents may be formed. In some cases, the partition may comprise a single cell. The cell may be lysed or permeabilized within the partition (e.g., droplet) to provide access to the nucleic acid molecule of the cell.

In some embodiments, the cell may be lysed within the cell bead, and a subset of the intracellular contents may associate with the bead. In some cases, the cell bead may comprise thioacrydite-modified nucleic acid molecules that can hybridize with nucleic acids from the cell. For example, a poly-T nucleic acid sequence may be thioacrydite-modified and bound to the cell bead matrix. Upon cell lysis, the cellular nucleic acids (e.g., mRNA) may hybridize with the poly-T sequence. The retained intracellular contents may be released, for example, by addition of a reducing agent, e.g., DTT, TCEP, etc. The release may occur at any convenient step, such as before or after partitioning.

One or more processes may be carried out within a partition. For example, one or more processes selected from the group consisting of lysis, permeabilization, denaturation, hybridization, extension, duplication, and amplification of one or more components of a sample comprising the nucleic acid molecule may be performed within a partition. In some cases, multiple processes are carried out within a partition. The nucleic acid molecule or a cell comprising the nucleic acid molecule, may be co-partitioned with one or more reagents (e.g., as described herein) at any useful stage of the method. For example, the nucleic acid molecule contained within a cell may be co-partitioned with a probe and one or more additional reagents prior to hybridization of the probe with the target region of the nucleic acid molecule. Similarly, the nucleic acid molecule or a cell comprising the nucleic acid molecule may be released from a partition at any useful stage of the method. For example, the nucleic acid molecule or a cell comprising the nucleic acid molecule may be released from the partition subsequent to hybridization of a binding sequence of a nucleic acid barcode molecule to a sequence of a probe hybridized to the target region of the nucleic acid molecule. Alternatively, the nucleic acid molecule or a cell comprising the nucleic acid molecule, and/or another component of the sample comprising the same, may be released from the partition subsequent to denaturation of a complexed extended nucleic acid molecule that comprises a sequence complementary to the barcode sequence of a nucleic acid barcode molecule and a sequence complementary to the target region of the nucleic acid molecule. Duplication and/or amplification of the extended nucleic acid molecule may then be carried out within a solution. In some cases, the solution may comprise additional extended nucleic acid molecules generated through the same process carried out in different partitions. Each extended nucleic acid molecule may comprise a different barcode sequence or a sequence complementary to a different barcode sequence. In this instance, the solution may be a pooled mixture comprising the contents of two or more partitions (e.g., droplets).

Hybridization of a probe sequence of a probe to a target region of the nucleic acid molecule may be performed within or outside of a partition. In some cases, hybridization may be preceded by denaturation of a double-stranded nucleic acid molecule to provide a single-stranded nucleic acid molecule or by lysis or permeabilization of a cell. In some cases, the hybridization may occur in a cell bead comprising a cell. The sequence of the probe that is complementary to the target region may be situated at an end of the probe. Alternatively, this sequence may be disposed between other sequences such that when the probe sequence is hybridized to the target region, additional probe sequences extend beyond the hybridized sequence in multiple directions. The probe sequence that hybridizes to the target region of the nucleic acid molecule may be of the same or different length as the target region. For example, the probe sequence may be shorter than the target region and may only hybridize to a portion of the target region. Alternatively, the probe sequence may be longer than the target region and may hybridize to the entirety of the target region and extend beyond the target region in one or more directions. In addition to a probe sequence complementary to a target region of the nucleic acid molecule, the probe may comprise one or more additional probe sequences. For example, the probe may comprise the probe sequence complementary to the target region and a second probe sequence. The second probe sequence may have any useful length and other characteristics. The probe may comprise one or more additional sequences, such as one or more barcode sequences or unique molecule identifier (UMI) sequences. In some cases, one or more probe sequences of the probe may comprise a detectable moiety such as a fluorophore or a fluorescent moiety.

A probe sequence of the probe may be capable of hybridizing with a sequence of a nucleic acid barcode molecule. A nucleic acid barcode molecule may comprise a first binding sequence that is complementary to a probe sequence of the probe (e.g., a second probe sequence), a barcode sequence, and a second binding sequence. A nucleic acid barcode molecule may also comprise one or more additional functional sequences selected from the group consisting of primer sequences, primer annealing sequences, and immobilization sequences. The binding sequences may have any useful length and other characteristics. In some cases, the binding sequence that is complementary to a probe sequence of the probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions.

The barcode sequence of a nucleic acid barcode molecule may have any useful length and other characteristics (e.g., as described herein). The nucleic acid barcode molecule may be attached to a bead such as a gel bead (e.g., as described herein). The bead may be co-partitioned with the nucleic acid molecule or the cell comprising the nucleic acid molecule. The bead may comprise a plurality of nucleic acid barcode molecules that may be the same or different. The bead may comprise at least 10,000 nucleic acid barcode molecules attached thereto. For example, the bead may comprise at least 100,000, 1,000,000, or 10,000,000 nucleic acid barcode molecules attached thereto. In some cases, each nucleic acid barcode molecule of the plurality of nucleic acid barcode molecules may comprise a common barcode sequence. The nucleic acid barcode molecules may further comprise an additional barcode sequence that may be different for each nucleic acid barcode molecule attached to the bead. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, and a chemical stimulus. For example, the stimulus may be a reducing agent such as dithiothreitol Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead. In some cases, one or more nucleic acid barcode molecules may be released from the bead prior to hybridization of a binding sequence of a nucleic acid barcode molecule to a probe sequence of the probe hybridized to the nucleic acid molecule of interest. The one or more nucleic acid barcode molecules may be released from the bead within a partition including the bead and the nucleic acid molecule (or a cell comprising the nucleic acid molecule) and the probe. Releasing may take place before, after, or during hybridization of a probe sequence to a target region of the nucleic acid molecule.

Following hybridization of a binding sequence of the nucleic acid barcode molecule to a probe sequence of the probe hybridized to the target region of the nucleic acid molecule, the probe may be extended from an end of the probe to an end of the nucleic acid barcode molecule. Extension may comprise the use of an enzyme (e.g., a polymerase) to add one or more nucleotides to the end of the probe. Extension may provide an extended nucleic acid molecule comprising sequences complementary to the target region of the nucleic acid molecule of interest, the barcode sequence, and one or more additional sequences of the nucleic acid barcode molecule such as one or more binding sequences. Appropriate conditions and or chemical agents (e.g., as described herein) may then be applied to denature the extended nucleic acid molecule from the nucleic acid barcode molecule and the target nucleic acid molecule. In some cases, one or more processes may involve the use of thermosensitive agents. For example, in some cases, probes may be annealed or hybridized under one set of temperature conditions, and extension may occur under a different set of temperature conditions. In some cases, a Warm or Hot Start polymerase may be used. The nucleic acid barcode molecule and the target nucleic acid molecule may then undergo further analysis. For example, a second probe that may be identical to the first probe and comprise a probe sequence that is complementary to the target region of the nucleic acid molecule may hybridize to the target region, and the nucleic acid barcode molecule may hybridize to an additional probe sequence of the second probe. In some cases, hybridization of the nucleic acid barcode molecule to the probe may precede hybridization of the probe to the target region of the nucleic acid molecule. The extended nucleic acid molecule that has been released from the nucleic acid barcode molecule and the target nucleic acid molecule may be duplicated or amplified by, for example, one or more amplification reactions. The amplification reactions may comprise polymerase chain reactions (PCR) and may involve the use of one or more primers or polymerases. The extension, denaturation, and/or amplification processes may take place within a partition. Alternatively, materials may be released from a partition prior to extension, denaturation, or amplification. For example, materials may be released from a partition between the extension and denaturation processes. Denaturation may then take place within a solution comprising the extended nucleic acid molecule, nucleic acid barcode molecule, and target nucleic acid molecule. Alternatively, materials may be released from a partition subsequent to denaturation and prior to amplification. In some cases, the extended nucleic acid molecule may be duplicated or amplified within a partition to provide an amplified product. The extended nucleic acid molecule, or a complement thereof (e.g., an amplified product), may be detected via sequencing (e.g., as described herein).

Figure 9:
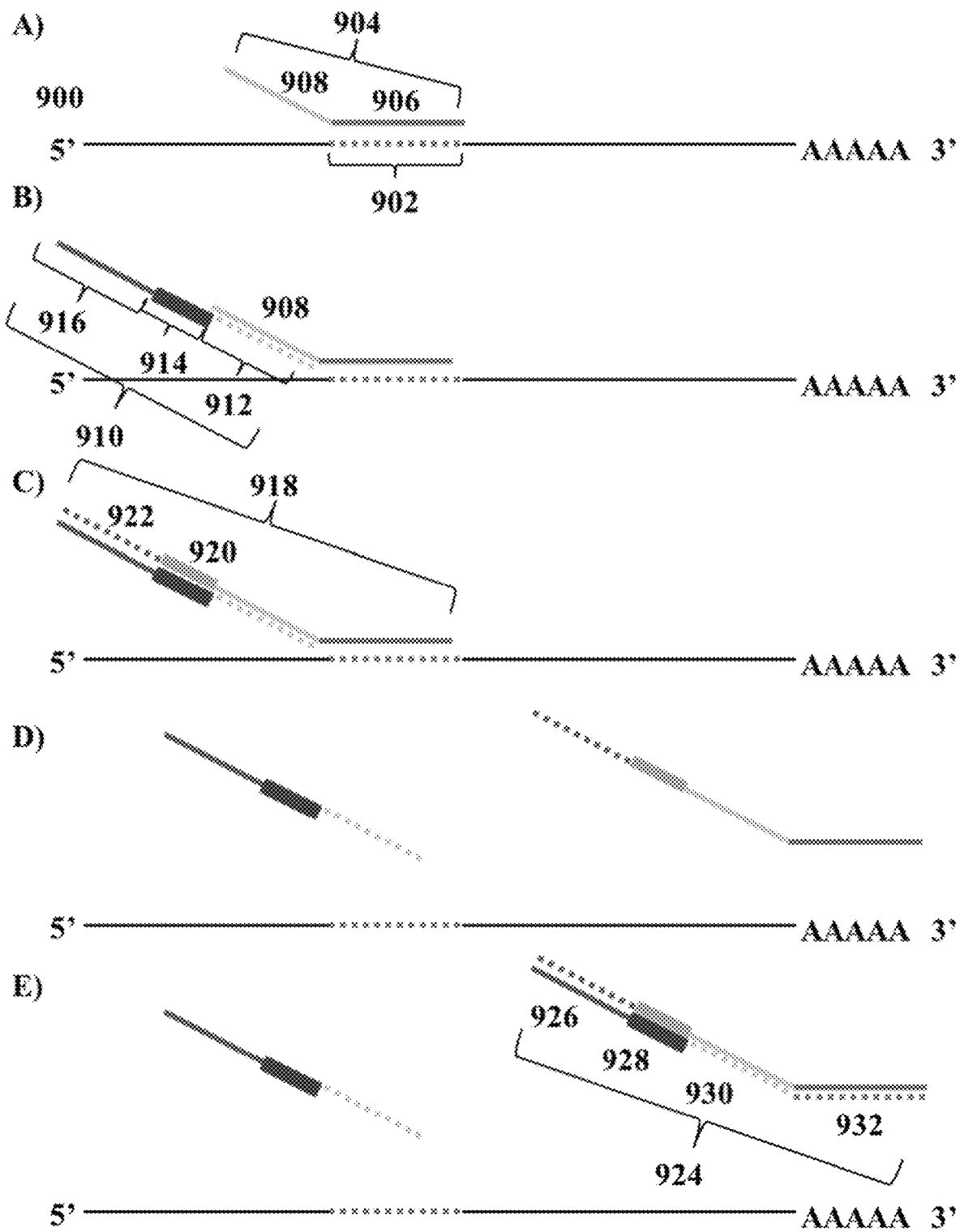
FIG. 9 schematically illustrates a method for analyzing a target nucleic acid molecule. Panel 9A illustrates a probe hybridized to a target nucleic acid molecule. Panel 9B illustrates a nucleic acid barcode molecule hybridized to a sequence of the probe and Panel 9C illustrates extension of the probe. Panel 9D illustrates optional denaturation of an extended nucleic acid molecule from the target nucleic acid molecule. Panel 9E illustrates amplification of the extended nucleic acid molecule.

FIG. 9 schematically illustrates a representative method of analyzing a nucleic acid molecule. Panel 9A shows a nucleic acid molecule 900 (e.g., a mRNA molecule) comprising a target region 902. Probe 904 comprises probe sequences 906 and 908. Probe sequence 906 has a sequence complementary to target region 902 of nucleic acid molecule 900 and hybridizes thereto. Unhybridized probes may be optionally removed using, e.g., one or more washing steps and/or enzymatic digestion reactions. Panel 9B shows nucleic acid barcode molecule 910 comprising binding sequence 912, adapter sequence 916 and barcode sequence 914 (which optionally may comprise a UMI sequence). Binding sequence 912 has a sequence complementary to probe sequence 908 and hybridizes thereto. Adapter sequence 916 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Panel 9C shows extension of probe 904 (and/or barcode molecule 910) to generate extended nucleic acid molecule 918, which comprises probe sequences 906 and 908; sequence 920, which is complementary to barcode sequence 914; and sequence 922, which is complementary to adapter sequence 916. Panel 9D shows denaturation of extended nucleic acid molecule 918 from nucleic acid molecule 900. In other embodiments, the nucleic acid extension reaction of Panel 9C generates a double stranded molecule (comprising strand 918, e.g., similar to 924) and the denaturation step described in Panel 9D is not performed. In still other embodiments, nucleic acid barcode molecule 910 is a partially double stranded molecule and is ligated to probe 904 in Panel 9C. Panel 9E shows optional duplication or amplification of extended nucleic acid molecule 918 (or a double stranded product comprising strand 918) to generate amplified product 924. Amplified product 924 comprises sequence 926, which is complementary to sequence 922 and the same or substantially the same as adapter sequence 916 of nucleic acid barcode molecule 910; sequence 928, which is complementary to sequence 920 and the same or substantially the same as barcode sequence 914 of nucleic acid barcode molecule 910; sequence 930, which is complementary to probe sequence 908 and the same or substantially the same as binding sequence 912 of nucleic acid barcode molecule 910; and sequence 932, which is complementary to probe sequence 906 and the same or substantially the same as target region 902 of nucleic acid molecule 900. The barcoded product, or a derivative thereof, may be detected, e.g., via nucleic acid sequencing (e.g., as described herein).

In some embodiments, nucleic acid molecule 900 is present in a cell. For instance, in some embodiments, a cell (which is optionally fixed) comprising nucleic acid molecule 900 is permeabilized and probe 904 is added and allowed to enter the cell and hybridize to region 902 as described above. Unbound probe 904 is then washed away (and/or enzymatically digested) and the cell is lysed to release probe 904 (which, in some instances, may still be hybridized to nucleic acid molecule 900) for barcoding as described above. Alternatively, nucleic acid barcode molecule 910 is allowed to enter the permeabilized cell for barcoding as described above.

In some embodiments, nucleic acid barcode molecule 910 is attached to a bead as described elsewhere herein. For example, nucleic acid barcode molecule 910 may be releasably attached to a bead (e.g., via labile bond as described herein). In some instances, the bead may be a gel bead as described herein, e.g., a degradable gel bead. In some embodiments, a permeabilized cell comprising nucleic acid molecule 900 is incubated with probe 904 and the cell is then partitioned into a partition (e.g., a droplet or well) with nucleic acid barcode molecule 910 (e.g., attached to a bead, such as a single bead) for barcoding. In other instances, a cell comprising nucleic acid molecule 900, probe 904, and nucleic acid barcode molecule 910 (e.g., attached to a bead, such as a single bead) are partitioned into a partition (e.g., a droplet or well) for probe-binding and barcoding.

In some instances, the methods described herein comprise contacting a plurality of permeabilized cells (or permeabilized nucleic or cell beads) with one or more probes (e.g., 904) targeted to one or more regions within one or more nucleic acid molecules (e.g., mRNA molecules). After probe binding and removal of excess probe, the plurality of cells and a plurality of beads (e.g., gel beads) comprising nucleic acid barcode molecules (e.g., releasably attached barcode molecules) may then be partitioned into a plurality of partitions (e.g., a plurality of droplets or a plurality of wells, e.g., in a microwell array) such that at least some partitions of the plurality of partitions comprise a single cell and a single bead. Probes (e.g., 904) may then be barcoded as generally described in FIG. 9. Barcoded nucleic acid molecules may then be analyzed by any suitable technique, including nucleic acid sequencing (e.g., Illumina sequencing).

The presently disclosed method may be applied to a single nucleic acid molecule or a plurality of nucleic acid molecules (e.g., a plurality of mRNA molecules). A method of analyzing a sample comprising a nucleic acid molecule may comprise providing a plurality of nucleic acid molecules (e.g., RNA molecules, such as a cell comprising a plurality of mRNA molecules), where each nucleic acid molecule comprises a target region, and a plurality of probes. In some cases, the target region of nucleic acid molecules of the plurality of nucleic acid molecules may comprise the same sequence. The plurality of probes may each comprise a first probe sequence complementary to a sequence of a target region of a nucleic acid molecule (e.g., mRNA molecule) of the plurality of nucleic acid molecules as well as a second probe sequence. One or more probes may comprise the same first probe sequence. A first probe sequence of a probe of the plurality of probes may be hybridized to a target region of a nucleic acid molecule of the plurality of nucleic acid molecules. A binding sequence of a nucleic acid barcode molecule of a plurality of nucleic acid barcode molecules may hybridize to the second probe sequence of a probe of the plurality of probes that is hybridized to a target region of a nucleic acid molecule of a plurality of nucleic acid molecules. Each nucleic acid barcode molecule of the plurality of nucleic acid barcode molecules may comprise a barcode sequence and a second binding sequence. The barcode sequence of each nucleic acid barcode molecule of the plurality of nucleic acid barcode molecules may be the same or different. Following hybridization of a binding sequence of a nucleic acid barcode molecule of the plurality of nucleic acid barcode molecules to a probe sequence of a probe of the plurality of probes that is hybridized to a target region of a nucleic acid molecule of the plurality of nucleic acid molecules, each probe of the plurality of hybridized probes may then be extended from an end of the probe to an end of the nucleic acid barcode molecule to which it is hybridized (e.g., an end of the second binding sequence of the nucleic acid barcode molecule). A plurality of extended nucleic acid molecules may thereby be created, where each extended nucleic acid molecule of the plurality of extended nucleic acid molecules comprises a sequence complementary to a target region of a nucleic acid molecule of the plurality of nucleic acid molecules and a sequence complementary to a barcode sequence of a nucleic acid barcode molecule of the plurality of nucleic acid barcode molecules.

In some cases, one or more processes described above may be performed within a partition. For example, each nucleic acid molecule of the plurality of nucleic acid molecules may be provided within a different partition. This may be achieved by partitioning a plurality of cells comprising the plurality of nucleic acid molecules within a plurality of separate partitions, where each cell comprises a target nucleic acid molecule and each partition of a plurality of different partitions of the plurality of separate partitions comprises a single cell. Access to a target nucleic acid molecule contained within a cell in a partition may be provided by lysing or permeabilizing the cell (e.g., as described herein). Nucleic acid barcode molecules provided within each partition of the plurality of different partitions of the plurality of separate partitions may be provided attached to beads. For example, each partition of the plurality of different partitions of the plurality of separate partitions may comprise a bead comprising a plurality of nucleic acid barcode molecules attached thereto (e.g., as described herein). The plurality of nucleic acid barcode molecules attached to each bead may comprise a different barcode sequence, such that each partition of the plurality of different partitions of the plurality of separate partitions comprises a different barcode sequence. Upon release of components from the plurality of different partitions of the plurality of separate partitions (e.g., following extension of each probe), each extended nucleic acid molecule may comprise a sequence complementary to a different barcode sequence, such that each extended nucleic acid molecule can be traced to a given partition and, in some cases, a given cell.

In another aspect, the present disclosure provides a method comprising providing a sample comprising a nucleic acid molecule (e.g., a ribonucleic acid (RNA) molecule) having a first target region and a second target region. The first target region may be adjacent to the second target region a first probe and a second probe. The first probe may comprise a first probe sequence and a second probe sequence, where the first probe sequence of the first probe is complementary to the first target region of the nucleic acid molecule. The second probe may comprise a third probe sequence that is complementary to the second target region of the nucleic acid molecule. The first probe sequence may also comprise a first reactive moiety, and the third probe sequence may comprise a second reactive moiety. The sample may be subjected to conditions sufficient to hybridize (i) the first probe sequence of the first probe to the first target region of the nucleic acid molecule and (ii) the third probe sequence of the second probe to the second target region of the nucleic acid molecule such that the first reactive moiety of the first probe sequence is adjacent to the second reactive moiety of the third probe sequence. The reactive moieties may then be subjected to conditions sufficient to cause them to react to yield a probe-linked nucleic acid molecule comprising the first probe linked to the second probe. The probe-linked nucleic acid molecule may then be barcoded (e.g., within a partition) to provide a barcoded probe-linked nucleic acid molecule. Barcoding may comprise hybridizing a binding sequence of a nucleic acid barcode molecule to the second probe sequence of the first probe. The first probe of the barcoded probe-linked nucleic acid molecule may subsequently be extended from an end of the first probe to an end of the nucleic acid barcode molecule to which it is hybridized to provide an extended nucleic acid molecule. The extended nucleic acid barcode molecule may comprise the first probe, the second probe, a sequence complementary to the barcode sequence of the nucleic acid barcode molecule, and a sequence complementary to another sequence (e.g., another binding sequence) of the nucleic acid barcode molecule. The extended nucleic acid molecule may be denatured from the nucleic acid barcode molecule and the nucleic acid molecule of interest and then duplicated or amplified (e.g., using polymerase chain reactions (PCR) or linear amplification) to facilitate detection of the extended nucleic acid molecule or a complement thereof (e.g., an amplified product) by, e.g., sequencing. One or more of the methods described herein may allow for genomic, transcriptomic, or exomic profiling with higher sensitivity. One or more of the methods described herein may allow for profiling of non-polyadenylated targets (e.g., non-poly-A RNAs), splice junctions, single nucleotide polymorphism s (SNPs), fixed cells, etc. One or more of the methods described herein may be compatible for multiplexed analysis, such as using feature barcoding, as described elsewhere herein.

The methods described herein may facilitate gene expression profiling with single cell resolution using, for example, chemical ligation-mediated barcoding, amplification, and sequencing. The methods described herein may allow for gene expression analysis while avoiding the use of enzymatic ligation, specialized imaging equipment, and reverse transcription, which may be highly error prone and inefficient. For example, the methods may be used to analyze a pre-determined panel of target genes in a population of single cells in a sensitive and accurate manner. In some cases, the nucleic acid molecule analyzed by the methods described herein may be a fusion gene (e.g., a hybrid gene generated via translocation, interstitial deletion, or chromosomal inversion).

The nucleic acid molecule analyzed by the method may be a single-stranded or double-stranded nucleic acid molecule (e.g., as described herein). The nucleic acid molecule may be an RNA molecule such as an mRNA molecule. In some cases, the nucleic acid molecule may be a viral or pathogenic RNA. In some cases, the nucleic acid molecule may be a synthetic nucleic acid molecule previously introduced into or onto a cell. For example, the nucleic acid molecule may comprise a plurality of barcode sequences, and two or more barcode sequences may be target regions of the nucleic acid molecule.

The nucleic acid molecule (e.g., mRNA molecule) may comprise one or more features selected from the group consisting of a 5' cap structure, an untranslated region (UTR), a 5' triphosphate moiety, a 5' hydroxyl moiety, a Kozak sequence, a Shine-Dalgarno sequence, a coding sequence, a codon, an intron, an exon, an open reading frame, a regulatory sequence, an enhancer sequence, a silencer sequence, a promoter sequence, and a poly(A) sequence (e.g., a poly(A) tail). Features of the nucleic acid molecule may have any useful characteristics. Additional details of nucleic acid molecules are provided in the preceding section.

The nucleic acid molecule may comprise two or more target regions. In some cases, a target region may correspond to a gene or a portion thereof. Each region may have the same or different sequences. For example, the nucleic acid molecule may comprise two target regions having the same sequence located at adjacent positions along a strand of the nucleic acid molecule. Alternatively, the nucleic acid molecule may comprise two or more target regions having different sequences at adjacent positions along a strand of the nucleic acid molecule. As used herein with regard to two entities, "adjacent," may mean that the entities directly next to one other (e.g., contiguous) or in proximity to one another. For example, a first target region may be directly next to a second target region (e.g., having no other entity disposed between the first and second target regions) or in proximity to a second target region (e.g., having an intervening sequence or molecule between the first and second target regions). In some cases, the nucleic acid molecule may comprise additional target regions disposed at different locations along the same or a different strand of the nucleic acid molecule. For example, a double-stranded nucleic acid molecule may comprise one or more target regions in each strand that may be the same or different. Different target regions may be interrogated by different probes. For example, a first target region may be interrogated by a first probe having a first probe sequence that is complementary to the first target region, and a second target region may be interrogated by a second probe having a second probe sequence that is complementary to the second target region. One or both probes may further comprise one or more additional sequences (e.g., additional probe sequences, unique molecular identifiers (UMIs), or other sequences). For example, the first probe may further comprise a second probe sequence. The second probe sequence of the first probe may undergo hybridization with a binding sequence of a nucleic acid barcode molecule. The second probe may also comprise an additional probe sequence. This sequence may be different from the second barcode sequence of the first probe so that the first and second probes may hybridize to different nucleic acid barcode molecules.

The target regions of the nucleic acid molecule may have any useful characteristics (e.g., as described in the preceding section).

The nucleic acid molecule (e.g., RNA molecule, such as an mRNA molecule) of a sample may be included within a cell (e.g., as described in the preceding section). For example, the sample may comprise a cell comprising the nucleic acid molecule that may be, for example, a human cell, an animal cell, or a plant cell. Access to a nucleic acid molecule included in a cell may be provided by lysing or permeabilizing the cell (e.g., as described in the preceding section).

Hybridization of a probe sequence of a probe to a target region of the nucleic acid molecule may be performed within or outside of a cell, partition, and/or container. In some cases, a cell may be lysed within a cell bead and a subset of the intracellular contents (e.g., mRNA) may be retained in the cell bead, as described elsewhere herein. In such cases, hybridization of a probe sequence of a probe to a target region of the nucleic acid may occur prior to partitioning. In some cases, hybridization may be preceded by denaturation of a double-stranded nucleic acid molecule to provide a single-stranded nucleic acid molecule or by lysis or permeabilization of a cell. The sequence of a probe that is complementary to a target region may be situated at an end of the probe. Alternatively, this sequence may be disposed between other sequences such that when the probe sequence is hybridized to a target region, additional probe sequences extend beyond the hybridized sequence in multiple directions. A probe sequence that hybridizes to a target region of the nucleic acid molecule may be of the same or different length as the target region. For example, a probe sequence may be shorter than a target region and may only hybridize to a portion of the target region. Alternatively, a probe sequence may be longer than a target region and may hybridize to the entirety of the target region and extend beyond the target region in one or more directions. In addition to a probe sequence complementary to a target region of the nucleic acid molecule, a probe may comprise one or more additional probe sequences. For example, a probe may comprise a probe sequence complementary to a target region and a second probe sequence. The second probe sequence may have any useful length and other characteristics. In an example, the first probe comprises a first probe sequence capable of hybridizing to the first target region of the nucleic acid molecule of interest and a second probe sequence, and the second probe comprises a third probe sequence capable of hybridizing to the second target region of the nucleic acid molecule of interest. In some cases, the second probe may further comprise a fourth binding sequence. Both the first probe and the second probe may comprise one or more additional sequences, such as one or more barcode sequences or unique molecule identifier (UMI) sequences. In some cases, one or more probe sequences of a probe may comprise a detectable moiety such as a fluorophore or a fluorescent moiety.

A probe may comprise a reactive moiety. For example, a probe sequence of a first probe capable of hybridizing to a first target region of a nucleic acid molecule may comprise a first reactive moiety, and a probe sequence of a second probe capable of hybridizing to a second target region of the nucleic acid molecule may comprise a second reactive moiety. When the first and second probes are hybridized to the first and second target regions of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phorphorothioate), acids, amines, and phosphates. For example, the first reactive moiety of a first probe may comprise an azide moiety, and a second reactive moiety of a second probe may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe sequence of a first probe hybridized to a first target region of the nucleic acid molecule and a second reactive moiety of a third probe sequence of a second probe hybridized to a second target region of the nucleic acid molecule may link the first probe and the second probe to provide a probe-linked nucleic acid molecule. Upon linking, the first and second probes may be considered ligated. Accordingly, reaction of the first and second reactive moieties may comprise a chemical ligation reaction such as a copper-catalyzed 5' azide to 3' alkyne "click" chemistry reaction to form a triazole linkage between two probes. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

Figure 15:
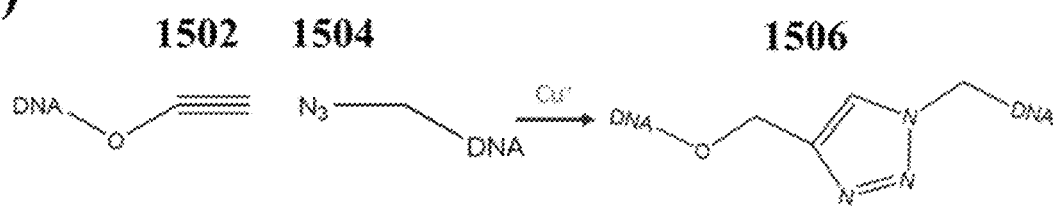
FIG. 15 shows various approaches for chemically-mediated nucleic acid ligation. Panel 15A illustrates formation of a triazole bond. Panel 15B illustrates formation of a phosphorothioate bond. Panel 15C illustrates formation of an amide bond. Panel 15D illustrates a formation of phosphoramidate bond. Panel 15E illustrates a conjugation reaction.
Figure 15:
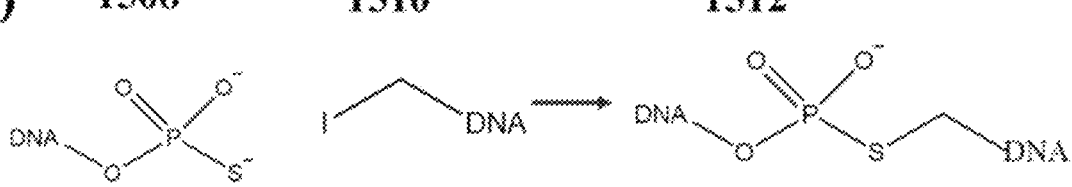
Figure 15:
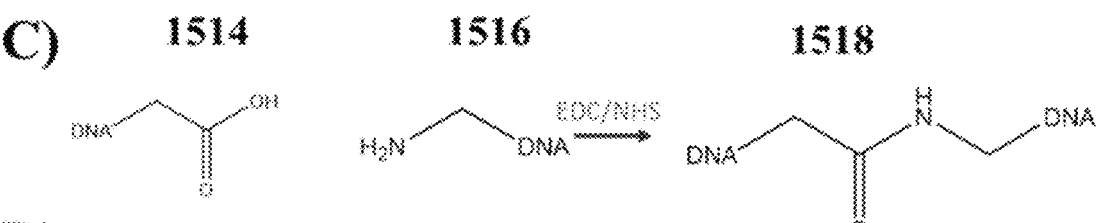
Figure 15:
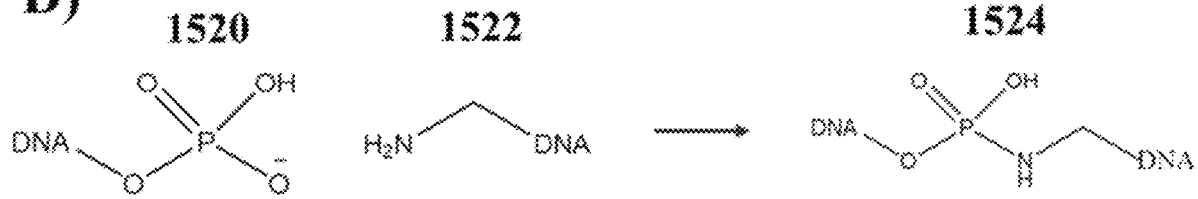
Figure 15:
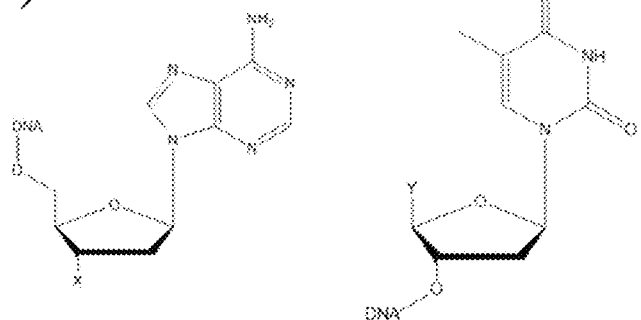

FIG. 15 illustrates examples of representative reactions. Panel 15A shows a chemical ligation reaction of an alkyne moiety 1502 and an azide moiety 1504 reacting under copper-mediated cycloaddition to form a triazole linkage 1506. Panel 15B shows a chemical ligation reaction of a phosphorothioate group 1508 with an iodide group 1510 to form a phosphorothioate linkage 1512. Panel 15C shows a chemical ligation reaction of an acid 1514 and amine 1516 to form an amide linkage 1518. Panel 15D shows a chemical ligation reaction of a phosphate moiety 1520 and an amine moiety 1522 to form a phosphoramidate linkage 1524. Panel 15E shows a conjugation reaction of two species 1526 and 1528.

In some instances, the first and second probes are hybridized to the first and second target regions of the nucleic acid molecule, and the first and second reactive moieties may be adjacent to one another. In some cases, the probes do not comprise reactive moieties and may be subjected to a nucleic acid reaction, providing a probe-linked nucleic acid molecule. For example, the probes may be subjected to an enzymatic ligation reaction, using a ligase (e.g., SplintR ligase KOD ligase, and/or T4 ligase). See, e.g., Zhang L., et al.; Archaeal RNA ligase from thermoccocus kodakarensis for template dependent ligation RNA Biol. 2017; 14(1): 36-44 for a description of KOD ligase. Following the enzymatic ligation reaction, the first and second probes may be considered ligated. In one embodiment, the first and second probes are both present in a linear nucleic acid molecule. In another embodiment, the linear nucleic acid molecule is a molecular inversion probe.

In other instances, the first and second probes are hybridized to the first and second target regions of the nucleic acid molecule, and the first and second reactive moieties may not be adjacent to one another. (e.g., comprise a gap region between the first and second probes). The first probe and the second probe may be positioned on (i.e., hybridized to) the nucleic acid molecule (e.g., mRNA) one or more nucleotides apart. For example, the first probe and the second probe may be spaced at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000 or more nucleotides apart. In some embodiments, the non-adjacent first and second probes may be ligated to form a probe-linked nucleic acid molecule. The probes may be subjected to an enzymatic ligation reaction, using a ligase, e.g., SplintR ligases, T4 ligases, KOD ligases, PBCV1 enzymes. Gaps between the probes may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, ribonucleotides are ligated between the first and second probes. In some embodiments, deoxyribonucleotides are ligated between the first and second probes. In one embodiment, the first and second probes are both present in a linear nucleic acid molecule. In another embodiment, the linear nucleic acid molecule may form a circularized nucleic acid molecule upon hybridization to target regions. The circularized nucleic acid molecule may then be subjected to conditions sufficient for ligation of its ends to form a circular probe-linked nucleic acid molecule.

A probe sequence of a probe (e.g., a probe of a probe-linked nucleic acid molecule) may be capable of hybridizing with a sequence (e.g., binding sequence) of a nucleic acid barcode molecule. In other cases, a probe may comprise a barcode molecule. A nucleic acid barcode molecule may comprise a first binding sequence that is complementary to a probe sequence of a probe (e.g., a second probe sequence), a barcode sequence, and a second binding sequence. In some cases, the binding sequence of a probe, a barcode nucleic acid molecule, or both, may be known and may bind to a target of interest (e.g., mRNA encoding a gene of interest). In some cases, the binding sequence may be degenerate (i.e., randomly generated). Employing degenerate or known sequences may be used in whole transcriptome or exome analysis or for targeted RNA sequencing, respectively. A nucleic acid barcode molecule may also comprise one or more additional functional sequences selected from the group consisting of primer sequences, primer annealing sequences, and immobilization sequences. The binding sequences may have any useful length and other characteristics. In some cases, the binding sequence that is complementary to a probe sequence of a probe may be the same length as the probe sequence. Alternatively, the binding sequence may be a different length of the probe sequence. For example, the binding sequence may be shorter than the probe sequence and may only hybridize to a portion of the probe sequence. Alternatively, the binding sequence may be longer than the probe sequence and may hybridize to the entirety of the probe sequence and extend beyond the probe sequence in one or more directions.

In some cases, the barcode nucleic acid molecule may hybridize to a binding sequence of one or more probes or adapters in a specific orientation. In some embodiments, a barcode may be configured to bind to the 3' end of a probe, an adapter, or an adapter-ligated probe. In some instances, binding of a probe to a barcode molecule is direct (e.g., through direct hybridization) or indirect, e.g., using a splint sequence as described elsewhere herein (e.g., FIG. 20). In some instances, probes and/or barcode molecules may comprise one or more ribonucleotides to facilitate binding and ligation. In one non-limiting example, a binding sequence of a probe may comprise a pair of 3' terminal ribonucleotides. A barcode nucleic acid molecule may be phosphorylated at the 5' end and may associate with the ribonucleotides via a splint molecule. The barcode nucleic acid molecule may then be ligated to the 3' end of the probe. Hybridization and ligation of a barcode nucleic acid molecule at the 3' end of a probe may be advantageous as this process may minimize downstream amplification artifacts, minimize barcode exchange, and may be compatible with removal of unligated probes.

In some cases, a first probe with a first probe sequence capable of hybridizing with a first target region of the nucleic acid molecule may comprise a second probe sequence capable of hybridizing with a sequence of a nucleic acid barcode molecule, and a second probe capable of hybridizing with a second target region of the nucleic acid molecule may not comprise a sequence capable of hybridizing with a nucleic acid barcode molecule. In other cases, the second probe may also comprise a probe sequence capable of hybridizing with a sequence of a nucleic acid barcode molecule. The first nucleic acid barcode molecule to which a first probe hybridizes may be different from a second nucleic acid barcode molecule to which a second probe hybridizes. For example, the first and second nucleic acid barcode molecules may comprise one or more different binding sequences and/or different barcode sequences.

In some cases, a first probe with a first probe sequence capable of hybridizing with a first target region of the nucleic acid molecule may comprise a second probe sequence capable of hybridizing with a first sequence of a nucleic acid adaptor molecule. The nucleic acid adaptor molecule may comprise this first sequence, or a complement thereof, and a second sequence that can hybridize with a first sequence of a nucleic acid barcode molecule. The nucleic acid adaptor molecule may also comprise a third sequence such as a primer region for downstream PCR (e.g., sequencing primer sequence), a barcode sequence, etc. The nucleic acid adaptor molecule may have any combination and derivatives or variants of the abovementioned sequences. In one non-limiting example, the nucleic acid adaptor molecule may comprise a first sequence that enables hybridization of the nucleic acid adapter molecule to the first probe and a second sequence that enables hybridization of the nucleic acid adapter molecule to a nucleic acid barcode molecule. The nucleic acid barcode molecule may hybridize to the adapter molecule. In some embodiments, the nucleic acid barcode molecule can comprise additional functional sequences, such as a barcode sequence, sequencing primer sequence, a UMI, a spacer sequence, and a plurality of ribonucleotides.

In some embodiments, the barcode nucleic acid molecule may comprise a splint nucleic acid sequence. The barcode nucleic acid molecule may be partially double-stranded and comprise a binding sequence and a barcode sequence. In some cases, the binding sequence may be complementary to a portion of the first probe, the second probe, or both probes. Hybridization of the binding sequence to the first probe or second probe or both probes may occur in a partition or outside of a partition. The nucleic acid barcode molecule may then be ligated to the first probe, the second probe, or both, using, for example, chemical or enzymatic ligation.

The barcode sequence of a nucleic acid barcode molecule may have any useful length and other characteristics (e.g., as described herein). The nucleic acid barcode molecule may be attached to a bead such as a gel bead (e.g., as described herein). The bead may be co-partitioned with the nucleic acid molecule or the cell comprising the nucleic acid molecule. The bead may comprise a plurality of nucleic acid barcode molecules that may be the same or different. The bead may comprise at least 10,000 nucleic acid barcode molecules attached thereto. For example, the bead may comprise at least 100,000, 1,000,000, or 10,000,000 nucleic acid barcode molecules attached thereto. In some cases, each nucleic acid barcode molecule of the plurality of nucleic acid barcode molecules may comprise a common barcode sequence. The nucleic acid barcode molecules may further comprise an additional barcode sequence that may be different for each nucleic acid barcode molecule attached to the bead. The plurality of nucleic acid barcode molecules may be releasably attached to the bead. The plurality of nucleic acid barcode molecules may be releasable from the bead upon application of a stimulus. Such a stimulus may be selected from the group consisting of a thermal stimulus, a photo stimulus, and a chemical stimulus. For example, the stimulus may be a reducing agent such as dithiothreitol. Application of a stimulus may result in one or more of (i) cleavage of a linkage between nucleic acid barcode molecules of the plurality of nucleic acid barcode molecules and the bead, and (ii) degradation or dissolution of the bead to release nucleic acid barcode molecules of the plurality of nucleic acid barcode molecules from the bead. In some cases, one or more nucleic acid barcode molecules may be released from the bead prior to hybridization of a binding sequence of a nucleic acid barcode molecule to a probe sequence of the probe hybridized to the nucleic acid molecule of interest. The one or more nucleic acid barcode molecules may be released from the bead within a partition including the bead and the nucleic acid molecule (or a cell comprising the nucleic acid molecule) and the probe.

Releasing may take place before, after, or during hybridization of a probe sequence to a target region of the nucleic acid molecule.

Figure 10:
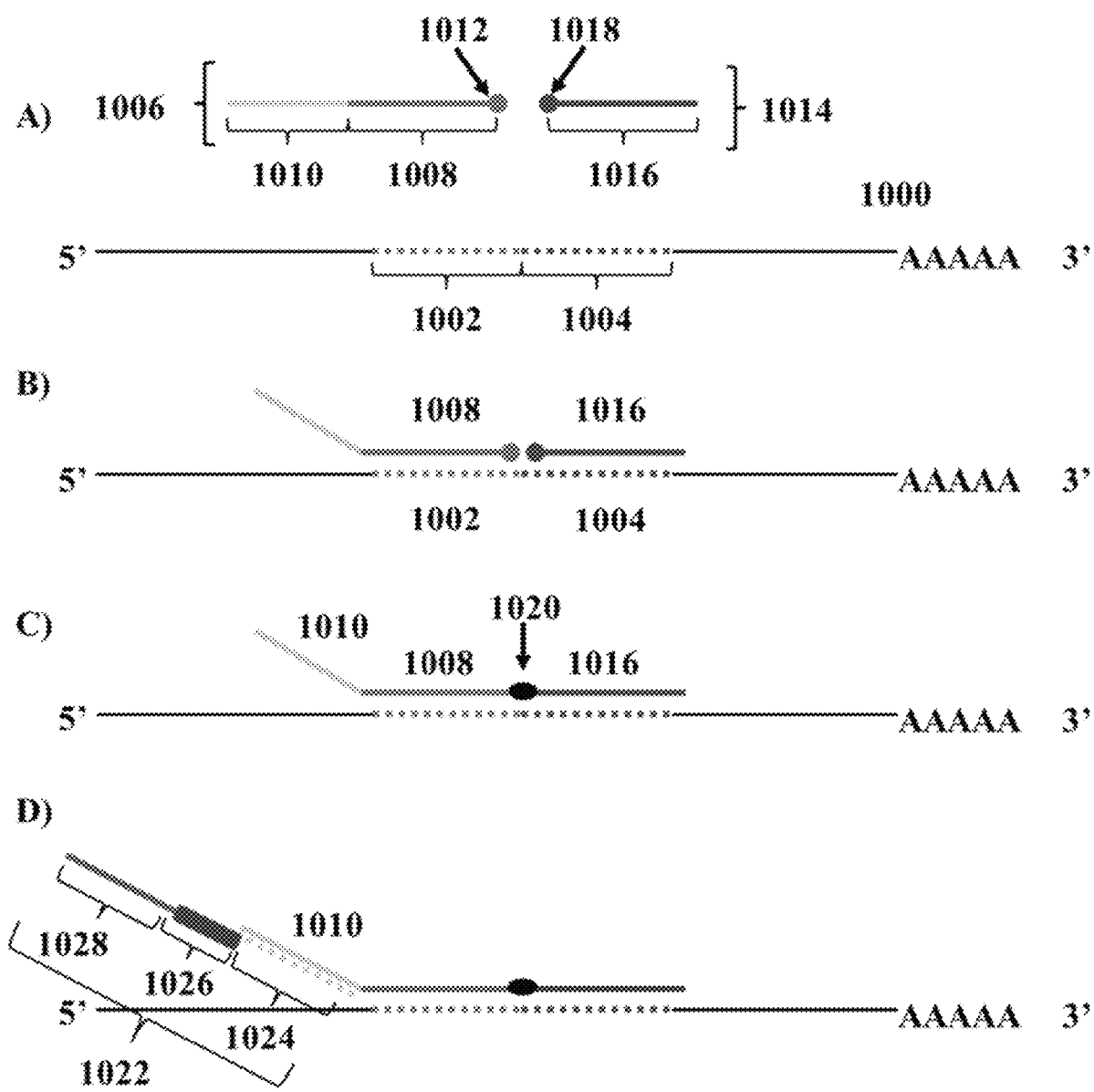
FIG. 10 schematically illustrates a method for analyzing a target nucleic acid molecule. Panel 10A illustrates a target nucleic acid molecule, a first probe, and a second probe, and Panel 10B illustrates a target nucleic acid molecule with the first and second probes hybridized thereto. Panel 10C illustrates a probe-linked nucleic acid molecule, while Panel 10D illustrates a barcoded probe-linked nucleic acid molecule.
Figure 11:
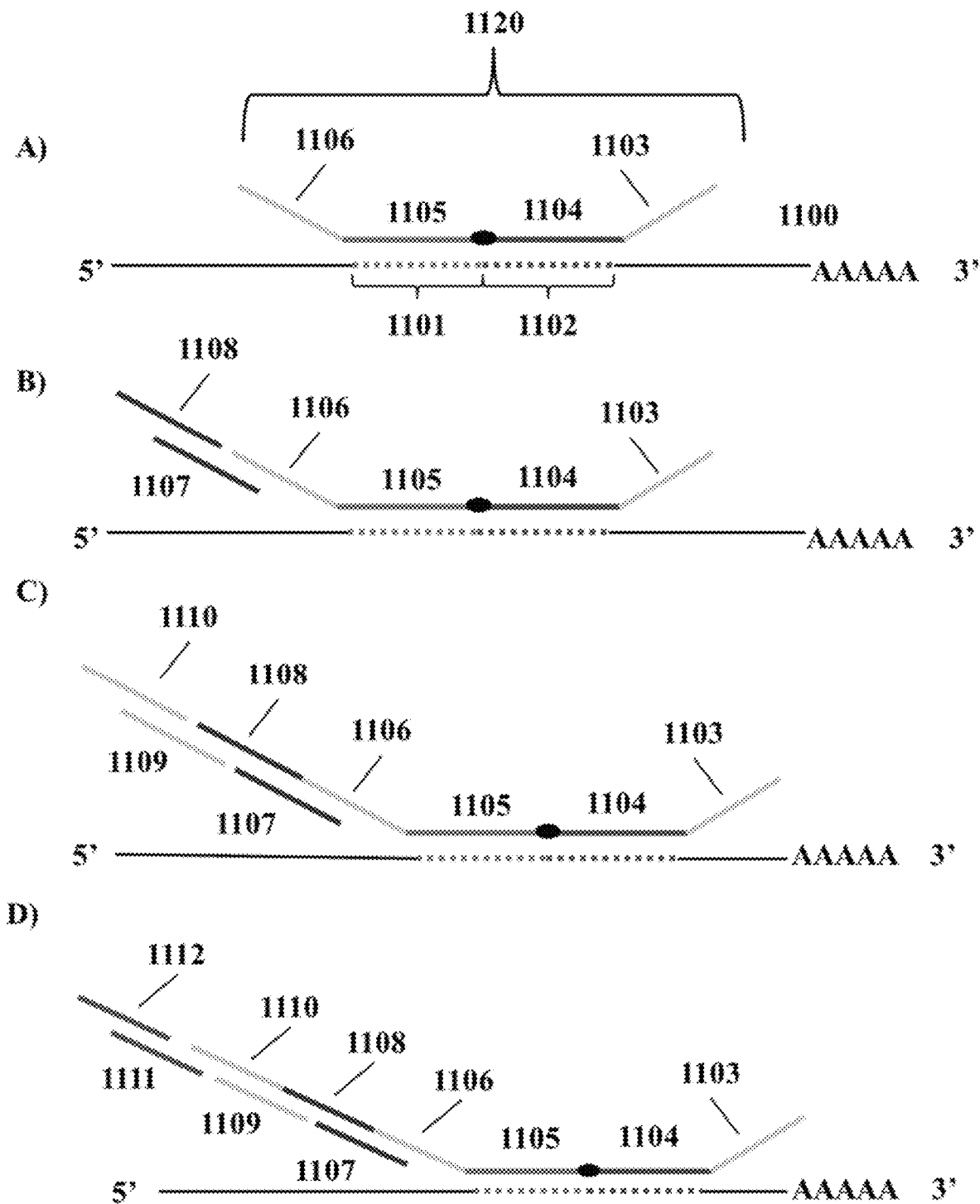
FIG. 11 illustrates a barcoding scheme using a split-pool approach. Panel 11A illustrates a probe-bound nucleic acid molecule. Panel 11B shows the addition of a first barcode sequence segment. Panel 11C shows the addition of a second barcode sequence segment. Panel 11D shows addition of a third barcode sequence segment.

FIG. 10 schematically illustrates a representative method of analyzing a nucleic acid molecule. Panel 10A shows a nucleic acid molecule 1000 (e.g., a mRNA molecule) comprising target regions 1002 and 1004. In some instances, target regions 1002 and 1004 are adjacent to one another. Probe 1006 comprises probe sequence 1008, binding sequence 1010, and reactive moiety 1012. Probe 1014 comprises probe sequence 1016 and reactive moiety 1018. Probe sequence 1008 of probe 1006 is complementary to target region 1002 of nucleic acid molecule 1000. Similarly, probe sequence 1016 of probe 1014 is complementary to target region 1004 of nucleic acid molecule 1000. Panel 10B shows probe sequence 1008 of probe 1006 hybridized to target region 1002 and probe sequence 1016 of probe 1014 hybridized to target region 1004. In some instances, reactive moiety 1012 of probe 1006 and reactive moiety 1018 of probe 1014 are adjacent to one another. Panel 10C shows linking moiety 1020 produced through a reaction of reactive moieties 1012 and 1018. In some cases, moieties 1012 and 1018 are ligated chemically (e.g., click chemistry), and in other cases, enzymatically (e.g., a ligase, such as SplintR, KOD ligase, or T4 ligase). Linked probes 1006 and 1014 comprise a probe-linked nucleic acid molecule comprising sequences 1010, 1008, and 1016. Panel 10D shows nucleic acid barcode molecule 1022 comprising adapter sequence 1028, barcode sequence 1026 (which optionally may comprise a UMI sequence), and binding sequence 1024, which is complementary to binding sequence 1010. Adapter sequence 1028 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Nucleic acid barcode molecule 1022 is then hybridized to binding sequence 1010 of the probe-linked nucleic acid molecule. A barcoded probe-linked nucleic acid molecule is then generated using, e.g., a nucleic acid extension reaction and/or ligation reaction as described in, e.g., Panel 9C. In some cases, probe 1014 may comprise an additional binding sequence (not shown). Probe sequence 1016 may hybridize to another nucleic acid barcode molecule or primer comprising a sequence complementary to probe sequence 1016. In some cases, moieties 1012 and 1018 may not be reactive and can be ligated using an enzyme (e.g., a ligase, such as SplintR, T4 ligase, KOD ligase, etc.). In some instances, where target regions 1002 and 1004 are not adjacent to one another, probe 1006 and/or 1014 may be extended in a nucleic acid extension reaction and ligated together as described elsewhere herein.

In some instances, following hybridization of a binding sequence 1024 of the nucleic acid barcode molecule 1022 to a binding sequence 1010 of a probe (e.g., probe-linked nucleic acid molecule) hybridized to a target region of the nucleic acid molecule 1000, the probe may be extended in a nucleic acid extension reaction to generate a barcoded probe-linked nucleic acid molecule. Extension may comprise the use of an enzyme (e.g., a polymerase) to add one or more nucleotides to the end of the probe and/or nucleic acid barcode molecule. Extension may provide a barcoded probe-linked nucleic acid molecule comprising sequences complementary to: (i) the first 1002 and second 1004 target regions of the nucleic acid molecule of interest 1000, (ii) the barcode sequence 1026, and (iii) one or more additional sequences of the nucleic acid barcode molecule such as one or more adapter sequences (e.g., 1028). In some instances, the barcoded probe-linked nucleic acid molecule is single stranded. In other instances, the barcoded probe-linked nucleic acid molecule is double stranded. In some instances, where the barcoded probe-linked nucleic acid molecule is single stranded, appropriate conditions and or chemical agents (e.g., as described herein) may then be applied to denature the extended nucleic acid molecule from the target nucleic acid molecule. The target nucleic acid molecule may then undergo further analysis. For example, another set of probes may hybridize to the target regions of the nucleic acid molecule, and a nucleic acid barcode molecule may be appended to a probe sequence of one of the additional probes. In some cases, hybridization of the nucleic acid barcode molecule to the first probe may precede hybridization of the first and second probes to the target region of the nucleic acid molecule. The barcoded probe-linked nucleic acid molecule may be duplicated or amplified by, for example, one or more amplification reactions, which may in some instances be isothermal. The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded probe-linked nucleic acid molecule, or a derivative thereof, may be detected via nucleic acid sequencing (e.g., as described herein).

In some embodiments, nucleic acid molecule 1000 is present in a cell. For instance, in some embodiments, a cell (which is optionally fixed) comprising nucleic acid molecule 1000 is permeabilized and probes 1006 and 1014 are added and allowed to enter the cell and hybridize to regions 1002 and 1004 as described above. Unbound probes are then washed away (and/or enzymatically digested) and the probes enzymatically or chemically linked together as described elsewhere herein. The cell may then be lysed to release probe-linked nucleic acid molecule 1030 (which, in some instances, may still be hybridized to nucleic acid molecule 1000) for barcoding as described above. Alternatively, nucleic acid barcode molecule 1022 is allowed to enter the permeabilized cell for barcoding as described above. In some embodiments, nucleic acid barcode molecule 1022 is attached to a bead as described elsewhere herein. For example, nucleic acid barcode molecule 1022 may be releasably attached to a bead (e.g., via labile bond as described herein). In some instances, the bead may be a gel bead as described herein, e.g., a degradable gel bead. In some embodiments, a permeabilized cell comprising nucleic acid molecule 1000 is incubated with probes 1006 and 1014 and the cell is then partitioned into a partition (e.g., a droplet or well) with nucleic acid barcode molecule 1022 (e.g., attached to a bead, such as a single bead) for barcoding. In other instances, a cell comprising nucleic acid molecule 1000, probes 1006 and 1014, and nucleic acid barcode molecule 1022 (e.g., attached to a bead, such as a single bead) are partitioned into a partition (e.g., a droplet or well) for probe-binding and barcoding.

In some instances, the methods described herein comprise contacting a plurality of permeabilized cells (or permeabilized nucleic or cell beads) with one or more probes (e.g., probes 1006 and 1014) targeted to one or more regions (e.g., 1002 and 1004) within one or more nucleic acid molecules (e.g., mRNA molecules). After probe binding and removal of excess probe, the plurality of cells and a plurality of beads (e.g., gel beads) comprising nucleic acid barcode molecules (e.g., releasably attached barcode molecules) may then be partitioned into a plurality of partitions (e.g., a plurality of droplets or a plurality of wells, e.g., in a microwell array) such that at least some partitions of the plurality of partitions comprise a single cell and a single bead. Probes may then be barcoded as generally described above. Barcoded nucleic acid molecules or derivatives thereof may then be optionally further processed and analyzed by any suitable technique, including nucleic acid sequencing (e.g., Illumina sequencing).

Figure 12:
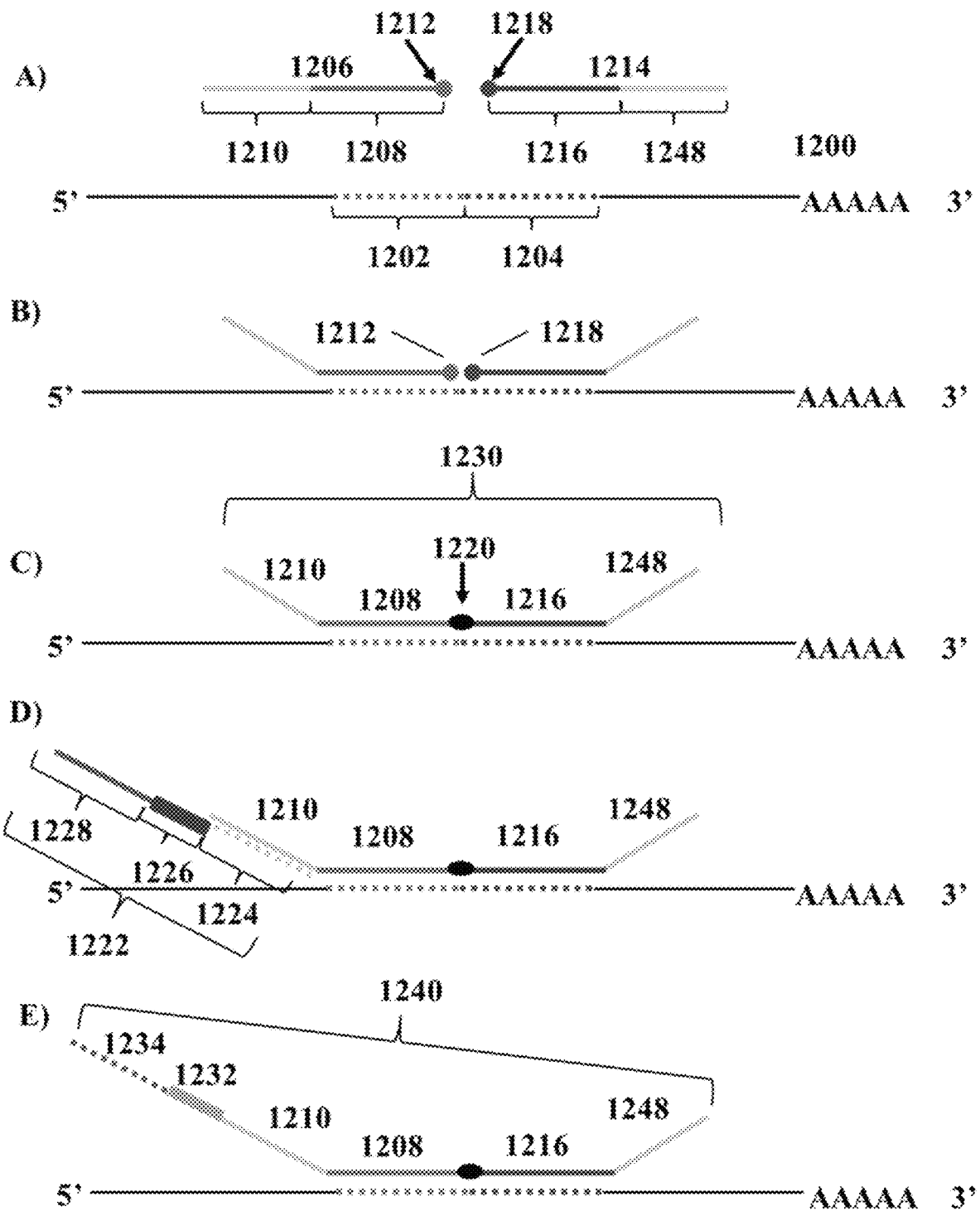
FIG. 12 schematically illustrates a method of analyzing a target nucleic acid molecule. Panel 12A illustrates a target nucleic acid molecule, a first probe, and a second probe, and Panel 12B illustrates a target nucleic acid molecule with the first and second probes hybridized thereto. Panel 12C illustrates a probe-linked nucleic acid molecule, while Panel 12D illustrates a barcode molecule hybridized to a probe-linked nucleic acid molecule. Panel 12E illustrates a barcoded probe-linked nucleic acid molecule.

FIG. 12 schematically illustrates a representative method of analyzing a nucleic acid molecule. Panel 12A shows a nucleic acid molecule 1200 (e.g., a mRNA molecule) comprising target regions 1202 and 1204. In some instances, target regions 1202 and 1204 are adjacent to one another. Probe 1206 comprises probe sequence 1208, binding sequence 1210 and reactive moiety 1212. Probe 1214 comprises probe sequences 1216, adapter sequence 1248, and reactive moiety 1218. Probe sequence 1208 of probe 1206 is complementary to target region 1202. Similarly, probe sequence 1216 of probe 1214 is complementary to target region 1204. Panel 12B shows probe sequence 1208 of probe 1206 hybridized to target region 1202 and probe sequence 1216 of probe 1214 hybridized to target region 1204. In some instances, reactive moiety 1212 of probe 1206 and reactive moiety 1218 of probe 1214 are adjacent to one another.

Panel 12C shows linking moiety 1220 produced through a reaction of reactive moieties 1212 and 1218. In some cases, moieties 1212 and 1218 are ligated chemically (e.g., click chemistry), and in other cases, enzymatically (e.g., a ligase, such as SplintR, KOD ligase, or T4 ligase). Linked probes 1206 and 1214 comprise a probe-linked nucleic acid molecule 1230 comprising sequences 1210, 1208, 1216, and 1248. Panel 12D shows nucleic acid barcode molecule 1222 comprising binding sequence 1224, barcode sequence 1226 (which optionally may comprise a UMI sequence), and binding sequence 1228, which is complementary to binding sequence 1210. Adapter sequence 1228 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Nucleic acid barcode molecule 1222 is then hybridized to binding sequence 1210 of the probe-linked nucleic acid molecule 1230. A barcoded probe-linked nucleic acid molecule 1240 is then generated using, e.g., a nucleic acid extension reaction and/or ligation reaction as described previously (see, e.g., Panel 9C). The barcoded probe-linked nucleic acid molecule 1240 may comprise sequences 1248, 1216, 1208, 1210, 1232 (complementary to barcode sequence 1226) and 1234 (complementary to adapter sequence 1228). In some instances, the barcoded probe-linked nucleic acid molecule 1240 is single stranded (e.g., only 1230 or 1222 is extended). In other instances, the barcoded probe-linked nucleic acid molecule 1240 is double stranded (e.g., both 1230 and 1222 are extended). In some instances, where the barcoded probe-linked nucleic acid molecule 1240 is single stranded, appropriate conditions and or chemical agents (e.g., as described herein) may then be applied to denature the extended nucleic acid molecule from the target nucleic acid molecule. The barcoded probe-linked nucleic acid molecule 1240 may be duplicated or amplified by, for example, one or more amplification reactions, which may in some instances be isothermal. The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded probe-linked nucleic acid molecule 1240, or a derivative thereof, may be detected via nucleic acid sequencing (e.g., as described herein).

In some embodiments, nucleic acid molecule 1200 is present in a cell. For instance, in some embodiments, a cell (which is optionally fixed) comprising nucleic acid molecule 1200 is permeabilized and probes 1206 and 1214 are added and allowed to enter the cell and hybridize to regions 1202 and 1204 as described above. Unbound probes are then washed away (and/or enzymatically digested) and the probes enzymatically or chemically linked together as described elsewhere herein. The cell may then be lysed to release probe-linked nucleic acid molecule 1230 (which, in some instances, may still be hybridized to nucleic acid molecule 1200) for barcoding as described above. Alternatively, nucleic acid barcode molecule 1222 is allowed to enter the permeabilized cell for barcoding as described above. In some embodiments, nucleic acid barcode molecule 1222 is attached to a bead as described elsewhere herein. For example, nucleic acid barcode molecule 1222 may be releasably attached to a bead (e.g., via labile bond as described herein). In some instances, the bead may be a gel bead as described herein, e.g., a degradable gel bead. In some embodiments, a permeabilized cell comprising nucleic acid molecule 1200 is incubated with probes 1206 and 1214 and the cell is then partitioned into a partition (e.g., a droplet or well) with nucleic acid barcode molecule 1222 (e.g., attached to a bead, such as a single bead) for barcoding. In other instances, a cell comprising nucleic acid molecule 1200, probes 1206 and 1214, and nucleic acid barcode molecule 1222 (e.g., attached to a bead, such as a single bead) are partitioned into a partition (e.g., a droplet or well) for probe-binding and barcoding. Nucleic acid barcode molecules and probes may be designed in any suitable 5' to 3' configuration. For example, a nucleic acid barcode molecule attached to a bead may be attached to the bead at the 3' end of the nucleic acid barcode molecule or at the 5' end of the nucleic acid barcode molecule.

In some instances, the methods described herein comprise contacting a plurality of permeabilized cells (or permeabilized nucleic or cell beads) with one or more probes (e.g., probes 1206 and 1214) targeted to one or more regions (e.g., 1202 and 1204) within one or more nucleic acid molecules (e.g., mRNA molecules). After probe binding and removal of excess probe, the plurality of cells and a plurality of beads (e.g., gel beads) comprising nucleic acid barcode molecules (e.g., releasably attached barcode molecules) may then be partitioned into a plurality of partitions (e.g., a plurality of droplets or a plurality of wells, e.g., in a microwell array) such that at least some partitions of the plurality of partitions comprise a single cell and a single bead. Probes (e.g., 1230) may then be barcoded as generally described above. Barcoded nucleic acid molecules (e.g., 1240) or derivatives thereof may then be optionally further processed and analyzed by any suitable technique, including nucleic acid sequencing (e.g., Illumina sequencing).

Figure 20:
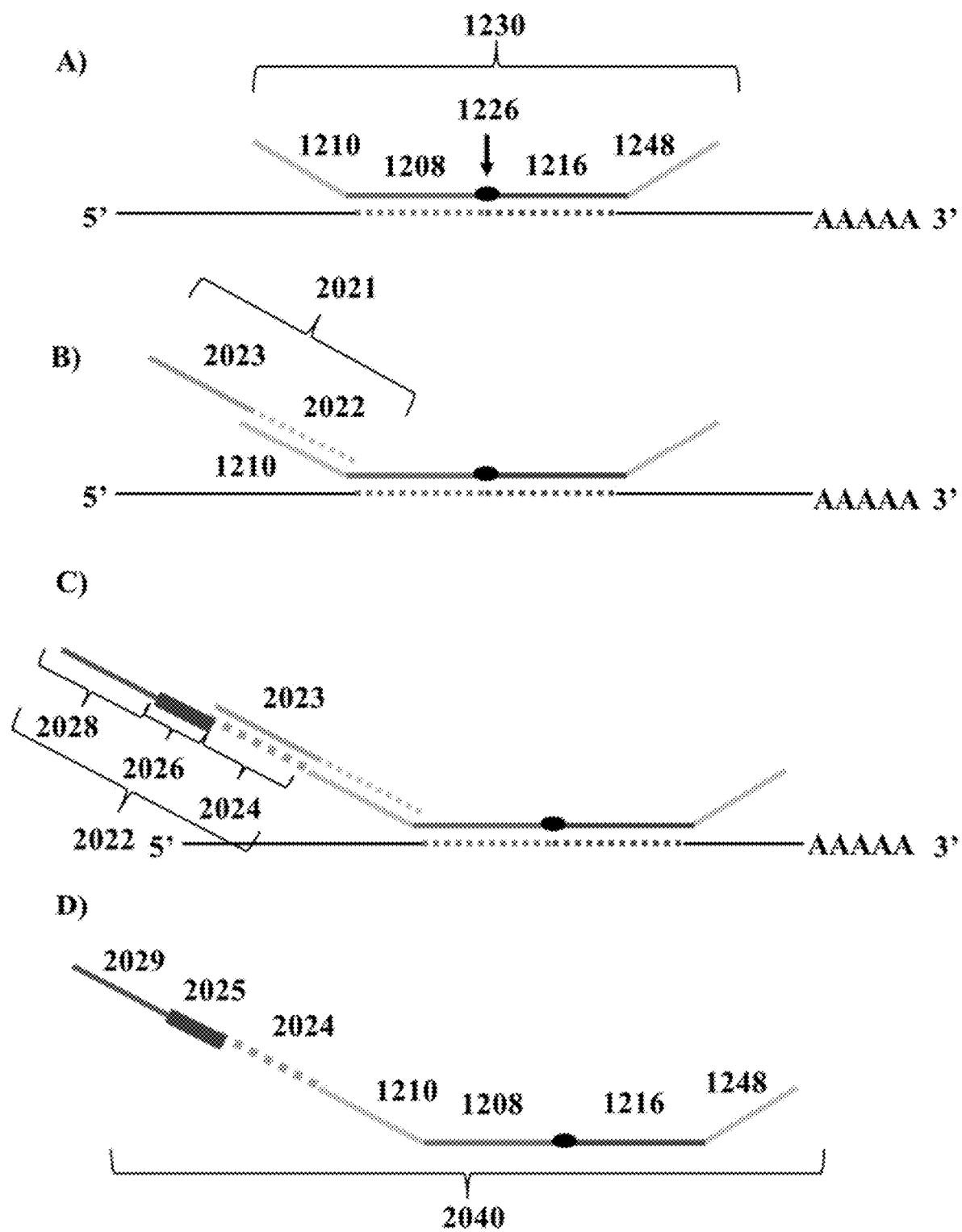
FIG. 20 schematically illustrates a method of analyzing a nucleic acid molecule.

In some cases, a nucleic acid barcode molecule (e.g., 1222) may be linked to the probe-linked nucleic acid molecule (e.g., 1230) via an adapter molecule. FIG. 20 schematically illustrates a representative method of analyzing a nucleic acid molecule using such adapter molecules. Panel 20A shows a probe-linked nucleic acid molecule, such as those described in, e.g., FIG. 10, and FIG. 12 (e.g., 1230). Panel 20B shows splint molecule 2021, which comprises a binding sequence 2022 complementary to a sequence of an adapter (e.g., 908, 1010, 1210, etc.) in a probe-linked nucleic acid molecule (e.g., 1230). The splint molecule 2021 may also comprise a binding sequence 2023. In some embodiments, the binding sequence 2023 may comprise or more ribonucleotides, such as ribo-guanines or ribo-cytosines. In some instances, the one or more ribonucleotides are present at the end (e.g., 5' terminus or 3' terminus) of the adapter sequence. In some instances, the splint molecule 2021 is a single stranded, or a partially double stranded molecule. Panel 20C shows hybridization of a barcode nucleic acid molecule 2022 to splint molecule 2021. The barcode nucleic acid molecule 2022 comprises an adapter sequence 2028, barcode sequence 2026, and binding sequence 2024, which is complementary to binding sequence 2023 of splint molecule 2021. Adapter sequence 2028 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). In some cases, the binding sequence 2024 of the barcode nucleic acid molecule 2022 comprises a plurality of ribonucleotides, such as ribo-cytosines or ribo-guanines. In some instances, the one or more ribonucleotides are present at the end (e.g., 5' terminus or 3' terminus) of the barcode nucleic acid molecule 2022. Following hybridization of the barcode nucleic acid molecule 2022, ligation (e.g., chemically or enzymatically) of the splinted, probe-linked nucleic acid molecule and barcode molecule 2022 may occur, to form, e.g., barcoded nucleic acid molecule 2040 as shown in Panel 20D. The barcoded probe-linked nucleic acid molecule 2040 may comprise sequences 1248, 1216, 1208, 1210, 2024 (complementary to binding sequence 2023), 2025 (complementary to barcode sequence 2026) and 2029 (complementary to adapter sequence 2028). Alternatively, the splinted, probe-linked nucleic acid molecule hybridized to the nucleic acid barcode molecule may be barcoded using a nucleic acid extension reaction as previously described. In some embodiments, a splint is not utilized, but instead the nucleic acid barcode molecule is partially double stranded and comprises a single stranded portion comprising, e.g., sequence 2022 to facilitate hybridization to the probe linked molecule 1230. In some instances, the barcoded probe-linked nucleic acid molecule is single stranded. In other instances, the barcoded probe-linked nucleic acid molecule is double stranded. The extended nucleic acid molecule may subsequently be subjected to one or more amplification reactions and/or further processing, such as those described in, e.g., FIG. 12. Splint molecule 2021 may be a DNA molecule or may be an RNA molecule.

In some instances, splint molecule 2021 is pre-hybridized to the barcode nucleic acid molecule 2022 to form a splint nucleic acid molecule. The splint nucleic acid molecule may be used in, e.g., Panel 20C to hybridize to the probe-linked nucleic acid molecule.

Figure 21:
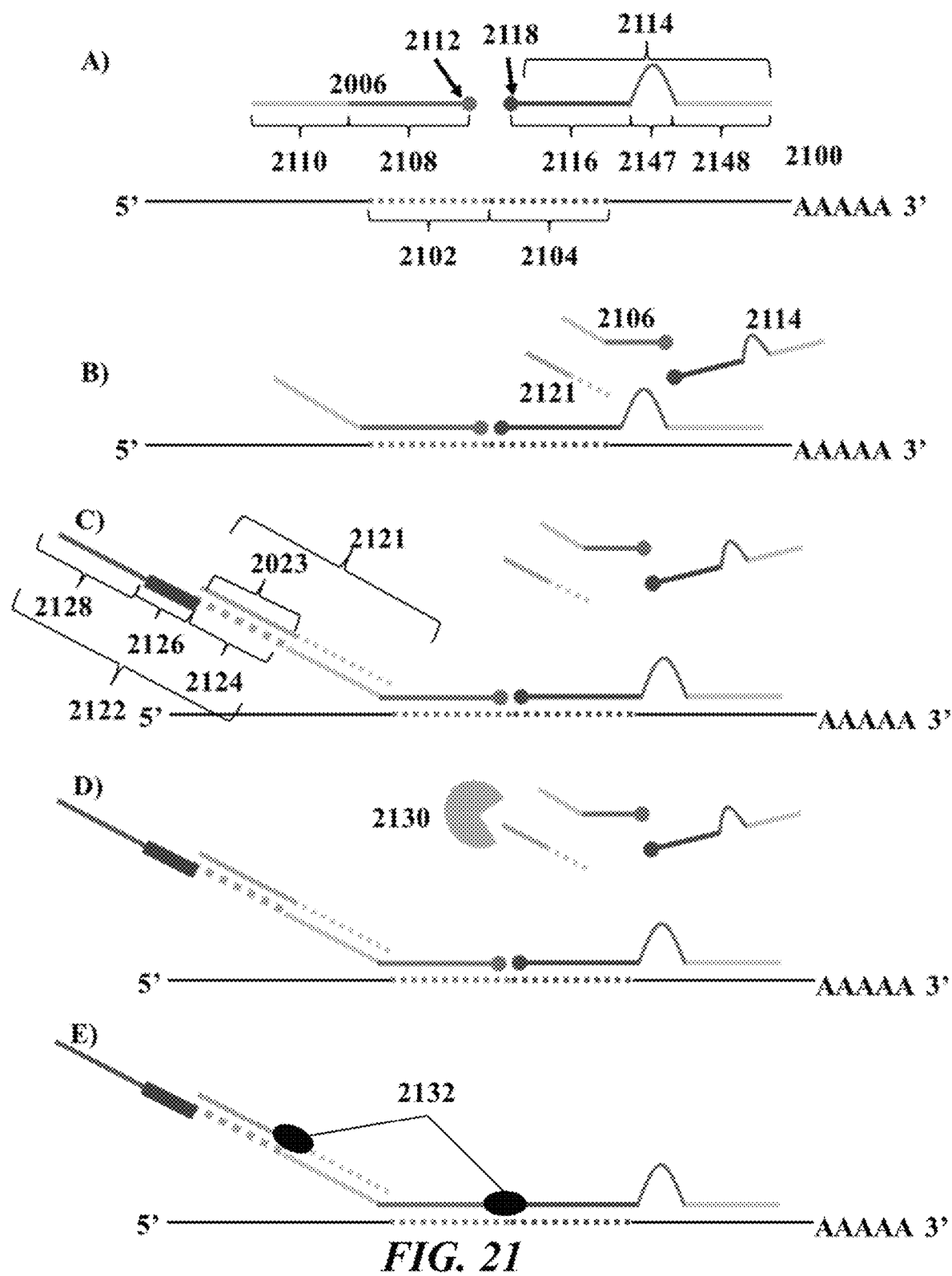
FIG. 21 schematically illustrates a method of analyzing a nucleic acid molecule. Panel 21A illustrates a nucleic acid molecule, a first probe, a second probe, and Panel 21B illustrates a nucleic acid molecule with the first and second probes hybridized thereto. Panel 21C illustrates a barcoded nucleic acid molecule, while Panel 21D illustrates digestion of unhybridized nucleic acid molecules. Panel 21E illustrates a probe-linked, barcoded nucleic acid molecule.

FIG. 21 schematically illustrates a representative method of analyzing a nucleic acid molecule using first and second probe molecules, an adapter molecule, and a barcode nucleic acid molecule. Panel 21A shows a nucleic acid molecule 2100 comprising adjacent target regions 2102 and 2104. Nucleic acid molecule 2100 is an mRNA molecule comprising a polyA sequence at its 3' end. Probe 2006 comprises probe sequences 2108 and 2110 and probe 2114 comprises probe sequences 2116 and 2148 and loop sequence 2147. Probe sequence 2108 of probe 2006 is complementary to target region 2102 and comprises reactive moiety 2112. Similarly, probe sequence 2116 of probe 2114 is complementary to target region 2104 and comprises reactive moiety 2118. Panel 21B shows probe sequence 2108 of probe 2006 hybridized to target region 2102 and probe sequence 2116 of probe 2114 hybridized to target region 2104. Reactive moiety 2112 of probe 2006 and reactive moiety 2118 of probe 2114 are adjacent to one another. An adapter molecule 2121 may also be introduced with probes 2106 and 2114. Panel 21C shows hybridization of an adapter molecule 2121 and barcode molecule 2122. The adapter molecule 2121 comprises a binding sequence that may hybridize with probe sequence 2110 of probe 2106. The adapter molecule 2121 may also comprise a spacer sequence 2023. In some embodiments, the spacer sequence 2023 may comprise a plurality of ribonucleotides, such as ribo-guanines or ribo-cytosines. Panel 21D shows hybridization of a barcode nucleic acid molecule 2122 to the adapter molecule 2121. The barcode nucleic acid molecule 2122 comprises a primer sequence 2128 (e.g., sequencing primer sequence), barcode sequence 2126, and binding sequence 2124, which is complementary to the spacer sequence 2023 of adapter molecule 2121. In some cases, the binding sequence 2124 of the barcode nucleic acid molecule 2122 comprises a plurality of ribonucleotides, such as ribo-cytosines or ribo-guanines. Panel 21D illustrates digestion of excess probe molecules. An exonuclease (e.g., a 3' exonuclease) 2130 may optionally be used to digest unhybridized probe molecules 2106, 2114 and adapter molecules 2121. Panel 21E shows ligation of the barcode molecule and the probes. Linking moiety 2132 may be produced through a reaction of reactive moieties 2112 and 2118. In some cases, moieties 2112 and 2118 are ligated using click chemistry, and in other cases, an enzyme (e.g., SplintR, KOD ligase, T4 ligase) may be used. Ligation of the probe molecules can produce a probe-linked molecule. Similarly, the barcode molecule 2122 may be linked by a linking moiety 2132 to one of the probes or the probe-linked molecule, generating a barcoded, probe-linked molecule. Further, extension of the linked probes of the probe-linked nucleic acid molecule may occur, to form an extended nucleic acid molecule similar to that shown in FIG. 12.

As will be appreciated, one or more processes described herein may occur inside a partition (e.g., well or droplet) or outside a partition (e.g., in bulk). One or more processes may occur in any convenient or useful order. For example, in some embodiments, a first probe may be hybridized to the target nucleic acid molecule. The first probe may then be barcoded, e.g., using an adapter molecule and a barcode molecule, a splinted barcode molecule, or any combination or derivatives thereof. The barcode molecule and the probe may be ligated (e.g., using click chemistry or enzymatically). In some cases, the unhybridized probes may then be digested (e.g., using an exonuclease). Subsequently, a second probe molecule may be introduced, which may hybridize to the target nucleic acid molecule, adjacent to the barcoded probe molecule. The second probe molecule may then be ligated (e.g. using click chemistry or enzymatically) to form a barcoded probe-linked nucleic acid molecule. In some cases, the barcoding may occur prior to, during, or following partitioning. Similarly, ligation and/or digestion may occur in a partition or outside of a partition.

Figure 16:
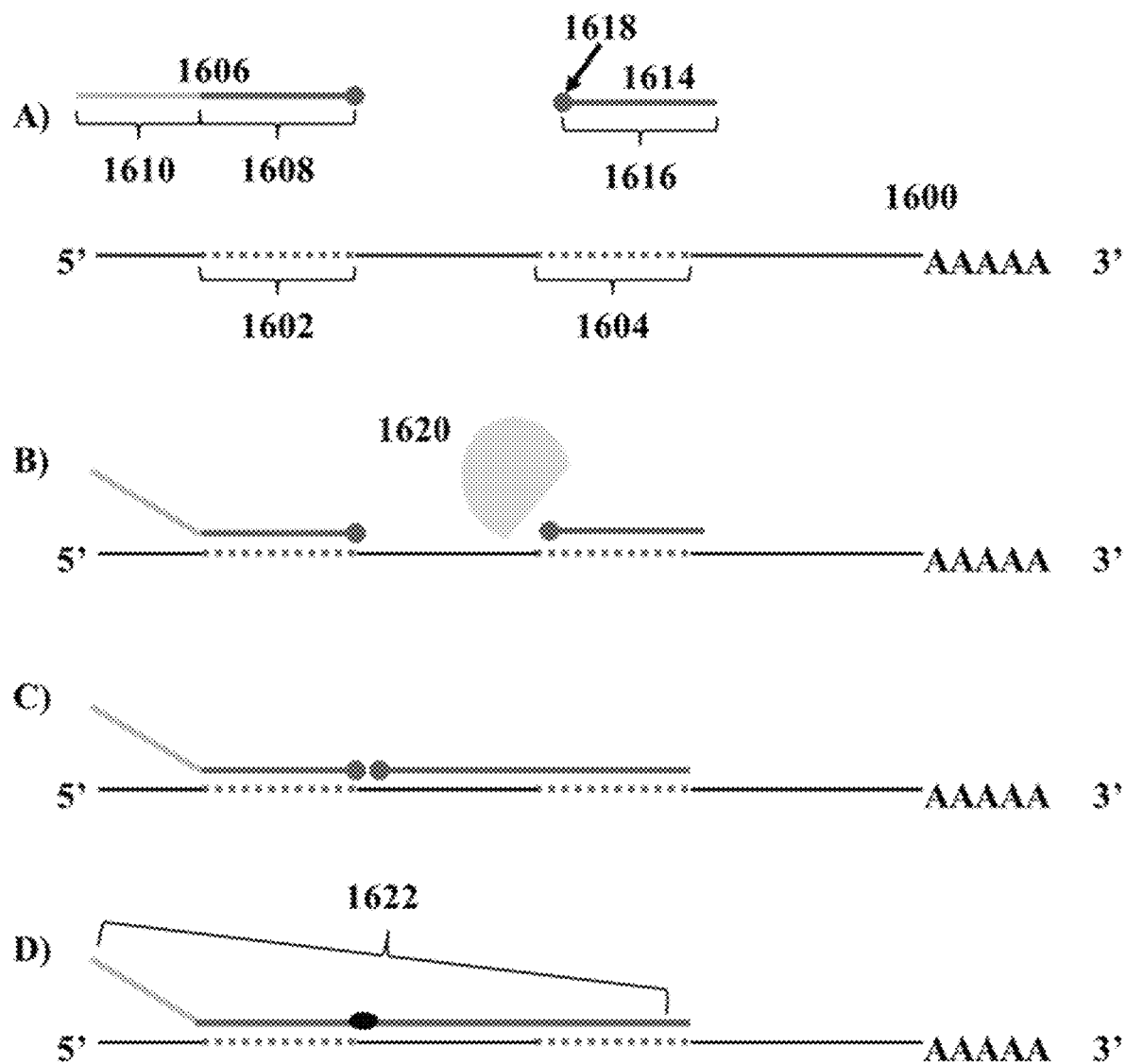
FIG. 16 shows a method for analyzing a nucleic acid molecule. Panel 16A illustrates a target nucleic acid molecule, a first probe, and a second probe, while Panel 16B illustrates a nucleic acid molecule with the first and second probes hybridized thereto and extension of the gap between probes. Panel 16C illustrates an extended nucleic acid molecule, and Panel 16D illustrates a probe-linked nucleic acid molecule.

FIG. 16 schematically illustrates a method of ligating non-adjacent probes to form a probe-linked nucleic acid molecule. Panel 16A shows a nucleic acid molecule 1600 comprising non-adjacent target regions 1602 and 1604. Nucleic acid molecule 1600 is an mRNA molecule comprising a polyA sequence at its 3' end. Probe 1606 comprises probe sequences 1608 and 1610 and probe 1614 comprises probe sequences 1616 and moiety 1618. Probe sequence 1608 of probe 1606 is complementary to target region 1602. Similarly, probe sequence 1616 of probe 1614 is complementary to target region 1604 and comprises a moiety 1618 onto which a polymerase may bind. Panel 16B shows probe sequence 1608 of probe 1606 hybridized to target region 1602 and probe sequence 1616 of probe 1614 hybridized to target region 1604. A polymerase 1620, such as Mu polymerase or DNA polymerase, extends probe 1616 by adding complementary ribonucleotides (e.g., ribonucleoside triphosphate (rNTP)) or deoxyribonucleotides (e.g., deoxyribonucleotide triphosphate (dNTP)), respectively (a gap-fill reaction). Panel 16C shows probes 1606 and extended probe 1614 as adjacent to one another. Panel 16D shows a ligation reaction of probe 1606 and extended probe 1614. Ligation may occur enzymatically, for example, by using a T4RNA ligase, KOD ligase, or a PBCV1 ligase, to form a probe-linked nucleic acid molecule 1622. Downstream analysis may subsequently be performed, such as barcoding and amplification, similar to as shown in Panels 12 D-F in FIG. 12.

Figure 17:
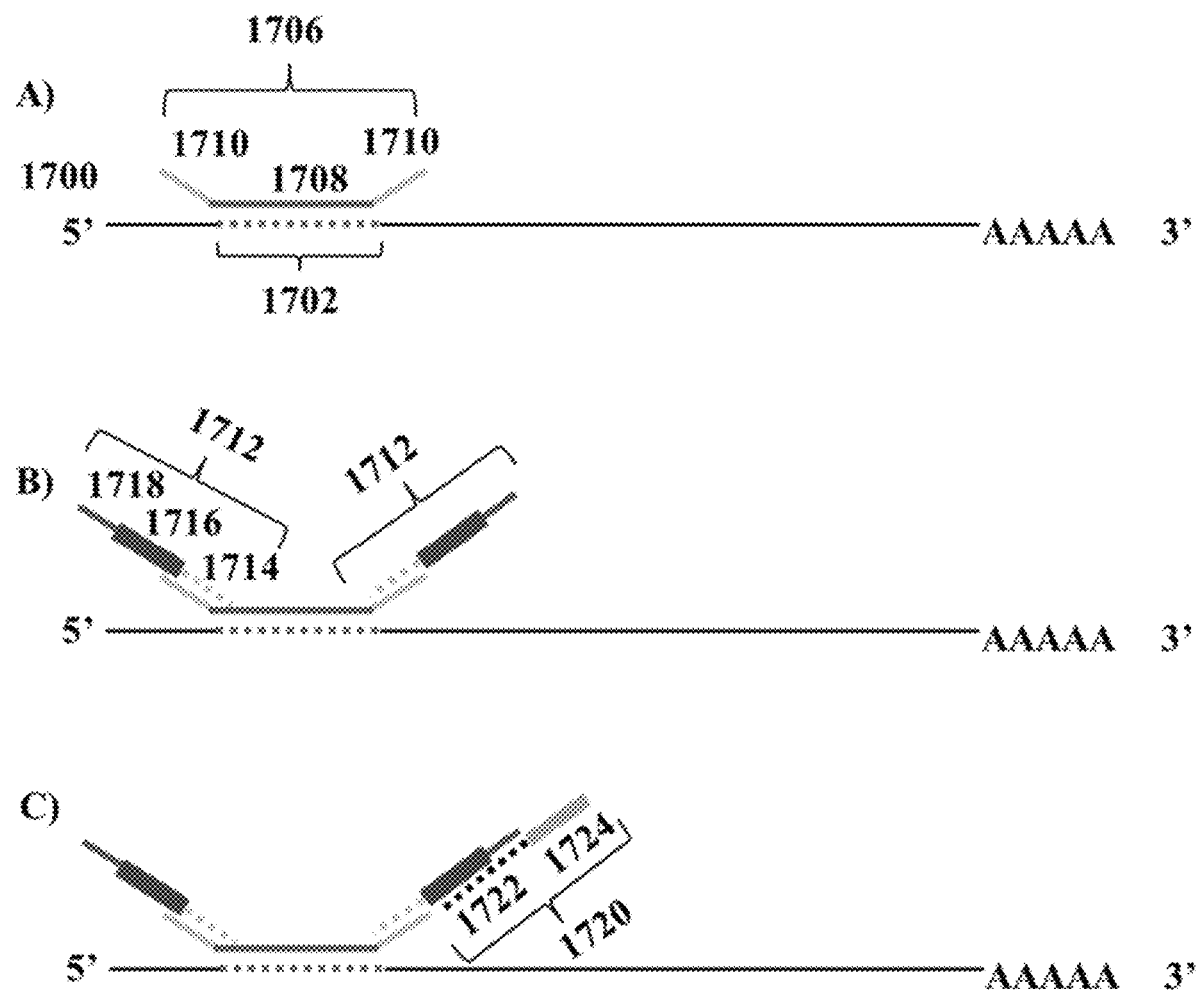
FIG. 17 illustrates a method for analyzing a target nucleic acid molecule. Panel 17A shows a target nucleic acid molecule and a first probe. Panel 17B illustrates a target nucleic acid molecule with the first probe hybridized thereto and a hybridization of an adaptor nucleic acid molecule to a sequence of the probe. Panel 17C illustrates hybridization of a barcode nucleic acid molecules to the adaptor nucleic acid molecule to generate a barcoded nucleic acid molecule.

FIG. 17 schematically shows an alternative method barcoding nucleic acid probes using adaptor nucleic acid molecules. Panel 17A shows a nucleic acid molecule 1700 comprising a target region 1702. Nucleic acid molecule 1700 is an mRNA molecule comprising a polyA sequence at its 3' end. Probe 1706 comprises probe sequences 1708 and adaptor sequences 1710. Probe sequence 1708 of probe 1706 is complementary to target region 1702. Panel 17B shows probe sequence 1708 of probe 1706 hybridized to target region 1702. An adaptor nucleic acid molecule 1712 comprises a sequence 1714 that hybridizes with the adaptor sequence 1710 of the nucleic acid probe 1706, and modular sequences 1716, 1718. Modular sequences 1716, 1718 may comprise, for example, a PCR primer sequence, a barcode, a constant sequence, and/or any variants or derivatives thereof. Panel 17C schematically shows a method of barcoding the probe nucleic acid 1706. A barcode nucleic acid molecule 1720 comprises a hybridization sequence 1722 that hybridizes with the adaptor nucleic acid molecule 1712 and a barcode sequence 1724. Hybridization of the barcode nucleic acid molecule may occur prior to or during partitioning. Following hybridization, other nucleic acid reactions may be performed, such as extension using DNA polymerase, to generate double-stranded, barcoded, nucleic acid probes (not shown). Subsequent amplification and sequencing may be performed. While FIGS. 10-12, 13, 20, 21 depict the first probe and the second probe as adjacent, it will be appreciated that these are for illustrative purposes only and are not meant to be limiting. In certain embodiments, the first probe and the second probe may not be adjacent, as depicted in FIG. 16. Thus, any of the processes, components, reagents, variations and derivatives of FIGS. 10-12, 13, 20, 21, may also apply to probes that are non-adjacent. Similarly, any of the processes, components, reagents, variations, and derivatives of FIG. 16 may also be applicable to those schemes depicted in FIGS. 10-12, 13, 20, 21.

In some cases, probe molecules that attach to the same target nucleic acid molecule may be linked to one another. For example, a single probe molecule (e.g., a probe nucleic acid molecule) may comprise (i) a first probe moiety at a first end that comprises a sequence complementary to a first target region of a nucleic acid molecule and (ii) a second probe moiety at a second end that comprises a sequence complementary to a second target region of the nucleic acid molecule that is adjacent to the first target region. A single probe molecule may comprise additional sequences, such as a sequencing primer binding site, or a primer site for downstream processing, e.g., rolling circle amplification. In some embodiments, the first probe and/or the second probe may comprise a cleavable linker. In some cases, the cleavable linker may comprise a restriction site and may be cleaved upon addition of a biological stimulus (e.g., restriction enzyme). In some embodiments, the cleavable linker may be cleaved upon the addition of a stimulus, e.g., a chemical, thermal, or photo stimulus. Upon hybridization of the first and second probe moieties to the target nucleic acid molecule, the first and second probe moieties may be adjacent and the probe molecule and target nucleic acid molecule may form a circular nucleic acid product. The circular nucleic acid product may then be subjected to conditions sufficient for ligation of the nucleic acid product, forming a circular probe-linked nucleic acid molecule. In some embodiments, the probe-linked nucleic acid molecule may be circularized. In some cases, linking of probes may occur before circularization or alternatively, linking of probes may occur simultaneously or subsequently to circularization. In some embodiments, circularization may occur via a splint nucleic acid, such as a circularization nucleic acid molecule. In such an embodiment, a circularization nucleic acid molecule may hybridize to a sequence on the first probe and a sequence on the second probe to form a circular nucleic acid product. In some embodiments, the first and second probe moieties may be connected as a single probe moiety. In some embodiments, the single probe moiety may be a circular nucleic acid product. In some embodiments, the single probe moiety may comprise single-stranded sequences that may be connected via a splint nucleic acid, such as a circularization nucleic acid molecule.

Hybridization kinetics of a circular nucleic acid product may be substantially different from those of a corresponding linear product involving two disconnected probes. In some cases, the use of a single probe molecule comprising two probe moieties may result in enhanced sensitivity of a target region of a nucleic acid molecule. For example, the use of a single probe molecule comprising two probe moieties may result in an increased number of target nucleic acid molecules having two probe moieties attached thereto relative to the use of two disconnected probes. Circularization of nucleic acid moieties may also facilitate removal of unwanted nucleic acid species and unhybridized probes by permitting the use of exonucleases without affecting ligation products. In some cases, unwanted nucleic acid species and unhybridized probes may be removed from a solution or partition including a circular nucleic acid product subsequent to its formation. For example, a circular nucleic acid product may be formed in a solution, and unwanted and unhybridized materials removed from the solution prior to barcoding or other processing. In such an example, the circular nucleic acid product may then be partitioned with one of more materials including one or more nucleic acid barcode molecules (e.g., coupled to a bead, as described herein) or nucleic acid binding molecules to undergo further processing. Alternatively, a circular nucleic acid product may be formed within a partition and hybridize with a nucleic acid barcode molecule and/or nucleic acid binding molecule within the partition to generate a barcoded circular nucleic acid product. The barcoded circular nucleic acid product may then be released from the partition to undergo further processing. A circular nucleic acid product may be opened at any useful time. For example, the circular nucleic acid product may be open following removal of unwanted and unhybridized materials. Alternatively, the circular nucleic acid product may be opened subsequent to hybridization of a nucleic acid barcode molecule and/or nucleic acid binding molecule to the circular nucleic acid product to generate a barcoded circular nucleic acid product. In some embodiments, the circular nucleic acid product may comprise a labile or cleavable linker. For example, the circular nucleic acid product may comprise a restriction site that is recognized by one or more restriction enzymes. Addition of one or more restriction enzymes may open the nucleic acid product. In another example, the circular nucleic acid product may comprise a photo- or thermal-sensitive linker that may be cleaved upon addition of light or heat. In some cases, a circular nucleic acid product may be amplified by rolling circle amplification (RCA) prior or subsequent to partitioning of the circular nucleic acid product. The use of RCA may increase efficiency of a barcoding process by generating multiple targets from the same original ligation event. An RCA product may be less susceptible to loss prior to partitioning due to its large size. An RCA product may be digested within a partition prior to a barcoding process by hybridization of a complementary probe and a restriction enzyme or other targeted endonuclease. RCA may be used in combination with or as an alternative to PCR.

In some embodiments, a first probe or a second probe may comprise a sequence that allows for further processing. In some cases, the first probe or the second probe may comprise a site. In some cases, the first probe and the second probe may be connected (e.g., the first probe and the second probe are parts of the same probe) and may comprise a transposition site. In some cases, the first probe and the second probe may form a circular nucleic acid product that comprises a transposition site. In some embodiments, a transposase may be used to add sequences to the first probe or the second probe or the circular nucleic acid product. For example, a transposase may be loaded with a transposase loop sequence. The transposase loop sequence may comprise sequences that may be used for further processing. For example, the transposase loop sequence may comprise a primer sequencing site, a barcode sequence, a sequencing primer sequence, a restriction site, a UMI sequence, a spacer sequence, an adapter sequence, and any combinations, variations, or derivatives thereof. In some cases, the transposase may introduce the transposase loop sequence into the first probe, the second probe, or the circular nucleic acid molecule. In some cases, the transposase may also introduce nicks or gaps in the first probe, the second probe, or the circular nucleic acid molecule. In such cases, the nicks or gaps may be filled, e.g., using one or more enzymes (e.g., polymerase, ligase). Further processing, e.g., amplification, rolling circle amplification may generate double-stranded probe molecules. In some cases, the double-stranded probe molecules may comprise a restriction site sequence and a barcode sequence and may be cleaved, e.g., upon addition of a restriction enzyme, to generate barcoded nucleic acid fragments. Further processing may be performed, such as an amplification reaction, to generate a sequencing library.

A transposase generally refers to an enzyme that is configured to bind a nucleic acid molecule, cleave the nucleic acid molecule and insert a nucleic acid sequence into the nucleic acid molecule (and optionally fragment the molecule, e.g., a tagmentation reaction). In some cases, a transposase can be configured to bind to a specific site on the nucleic acid molecule. In some cases, a transposase can be configured to bind to a random site on the nucleic acid molecule. Moreover, in some cases, a transposase can be configured to bind and optionally fragment open chromatin (e.g., euchromatin). Non-limiting examples of transposases include: a Tn transposase (e.g., Tn3, Tn5, Tn7, Tn10, Tn552, Tn903), a MuA tranposase, a Vibhar transposase (e.g., from *Vibrio harveyi*), a prokaryotic transposase, any member of the hAT superfamily of transposases (e.g., Hermes), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tol1, Tol2, TnlO, and Tyl. In some cases, the transposase may be derived from any of the above, such as a transposase including one or more mutations or modifications. In certain instances, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. Action of a transposase (e.g., insertion) may be facilitated and/or triggered by addition of one or more cations, such as one or more divalent cations (e.g., $Ca^{2+}$, $Mg^{2+}$, or $Mn^{2+}$) In a particular aspect, the transposase is a hyperactive transposase, such as Tn5.

Figure 13A:
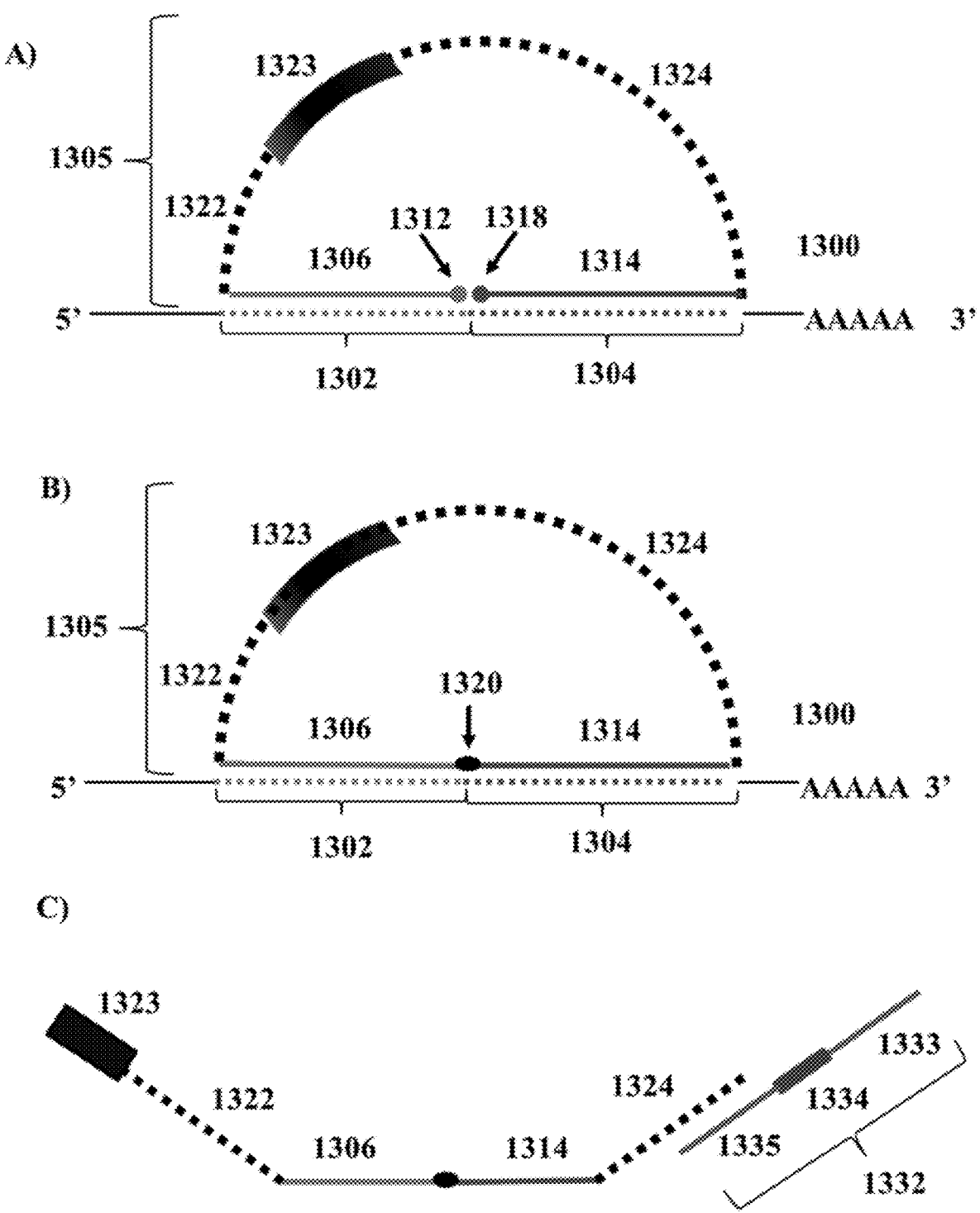
FIGS. 13A-13B schematically illustrate a method of analyzing a target nucleic acid molecule using a molecular inversion probe.
Figure 13B:
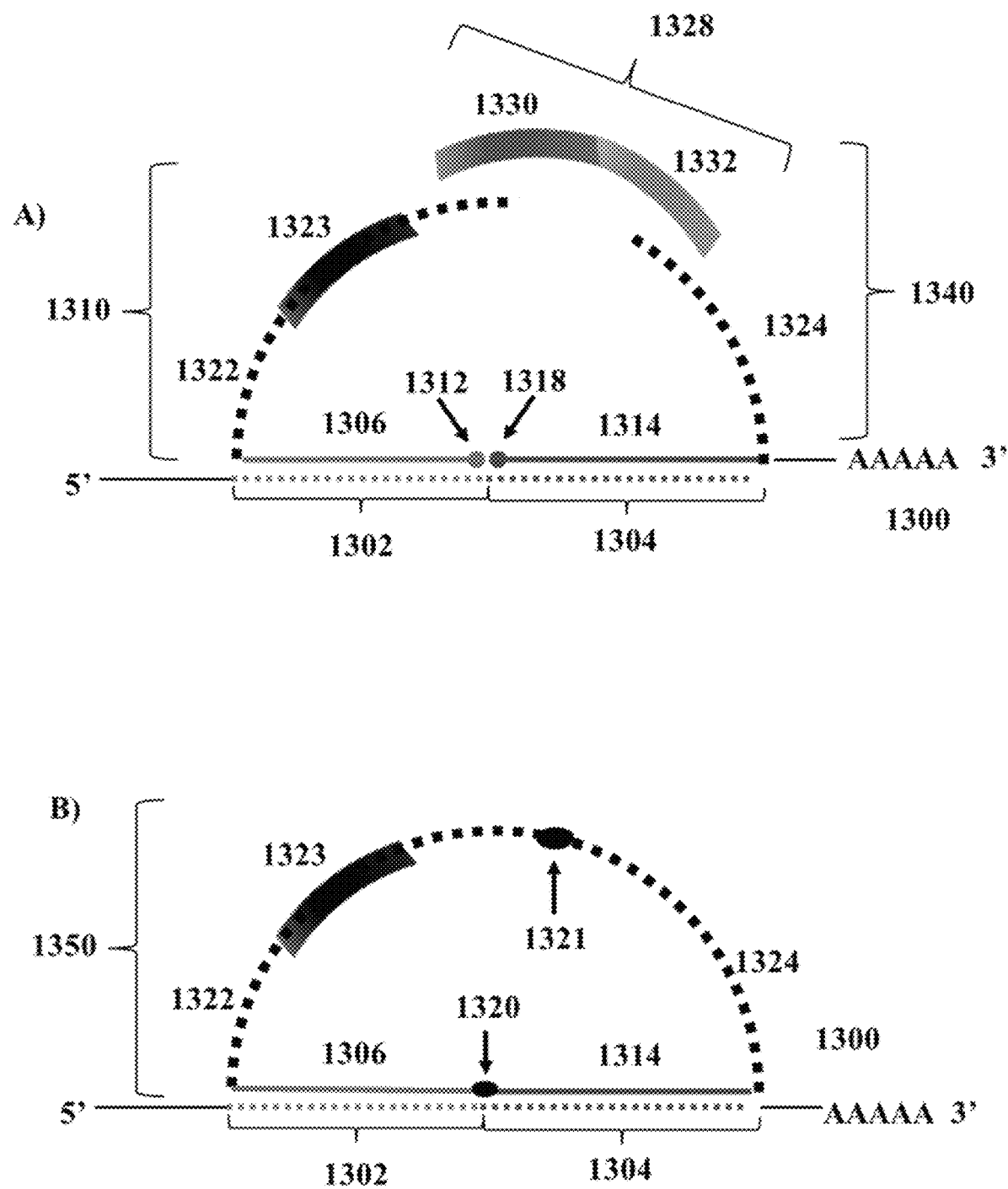

FIGS. 13A-B schematically illustrates a representative example of nucleic acid molecule analysis. Panel 13A of FIG. 13A shows probe molecule 1305 (e.g., a molecular inversion probe) comprising probe moiety 1306 at a first end and probe moiety 1314 at a second end. Probe moiety 1306 has a sequence complementary to target region 1302 of nucleic acid molecule 1300 (e.g., an mRNA molecule), while probe moiety 1314 has a sequence complementary to target region 1304 of nucleic acid molecule 1300. Probe moiety 1306 may comprise reactive moiety 1312, and probe moiety 1314 may comprise reactive moiety 1318. When probe moieties 1306 and 1314 are hybridized to nucleic acid molecule 1300, reactive moieties 1312 and 1318 may be adjacent. Probe moieties 1306 and 1314 are linked by a linking sequence. In some instances, the linking sequence comprises adapter sequence 1322, cleavable moiety 1323, and binding sequence 1324. Adapter sequence 1322 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). The linking sequence may also comprise one or more nucleic acid sequences and/or other moieties (amino acids, peptides, proteins, PEG moieties, hydrocarbon chains, or other linkers). In some embodiments, the linking sequence may comprise cleavable moiety 1323, such as a moiety comprising a thermolabile, photocleavable, or enzymatically cleavable bond. When probe moieties 1306 and 1314 are hybridized to nucleic acid molecule 1300, reactive moieties 1312 and 1318 may be adjacent.

Panel 13B of FIG. 13A shows ligation (e.g., chemical ligation, such as using a click chemistry reaction, or enzymatic ligation such as using a ligase) of reactive moieties 1312 and 1318 to form a linking moiety 1320, thereby circularizing probe 1305. As described elsewhere herein, linking moiety 1320 may comprise a triazole moiety generated by reaction of an alkyne moiety and an azide moiety. The ligation reaction of reactive moieties 1312 and 1318 may involve the use of a catalyst such as a copper species or a strained alkene and may take place within or outside of a partition. In some embodiments, the circular nucleic acid product may be cleaved and linearized by addition of a stimulus, e.g., biological, chemical, thermal or photo-stimulus. In one non-limiting example, the linking sequence may comprise a restriction site and application of a restriction enzyme cleaves site 1323, thereby linearizing probe 1305. In some instances, prior to barcoding, circularized probe 1305 is subjected to rolling circle amplification to generate multiple copies of probe sequence 1305. The concatemer of 1305 can be resolved to molecules suitable for barcoding by, e.g., cleaving cleavable moiety 1323. In some instances, cleavable moiety 1323 is a restriction site and the rolling circle amplification product can be cleaved by digesting the concatemer with a restriction enzyme specific of the restriction site. In some embodiments, adapter sequence 1322 comprises a UMI such that digested products from rolling circle amplification will each comprise a UMI to identify the probe 1305 of origin.

Panel 13C of FIG. 13A shows hybridization of sequence 1335 of nucleic acid barcode molecule 1332 to binding sequence 1324. Following hybridization, linearized probe 1305 (which may or may not have been subjected to rolling circle amplification and digestion) may be barcoded by, e.g., nucleic acid extension and/or ligation as previously described herein (e.g., FIG. 9, FIG. 10, FIG. 12, etc.). The barcoding reaction may be facilitated through use of a splint molecule as described elsewhere herein (e.g., FIG. 20).

Panel 13A of FIG. 13B shows probe molecule 1310 and probe molecule 1340 bound to nucleic acid molecule 1300. Probe molecule 1310 comprises a probe sequence 1306, adapter sequence 1322, cleavable moiety 1323 (e.g., as described above), and reactive moiety 1312. Probe sequence 1306 is complementary to target region 1302 of nucleic acid molecule 1300 (e.g., a mRNA molecule). Probe molecule 1340 comprises probe sequence 1314, binding sequence 1324, and reactive moiety 1318. Probe sequence 1314 is complementary to target region 1304 of nucleic acid molecule 1300 (e.g., a mRNA molecule).

Probe molecules 1310 and 1340 may also comprise one or more additional nucleic acid sequences and/or other moieties (amino acids, peptides, proteins, PEG moieties, hydrocarbon chains, or other linkers). A circularization nucleic acid molecule 1328 may be used to connect probe molecules 1310 and 1340. The circularization nucleic acid molecule 1328 may comprise sequences 1330 and 1332. Sequence 1330 of the circularization nucleic acid molecule may be capable of hybridizing with a sequence of probe molecule 1310, and sequence 1332 of the circularization nucleic acid molecule may be capable of hybridizing with a sequence (e.g., 1324) of probe molecule 1340. After hybridization of the circularization nucleic acid molecule with probe molecules 1310 and 1340, the two molecules may be ligated together at 1321. The ligation may be chemical or enzymatic as described elsewhere herein. When probe moieties 1306 and 1314 are hybridized to nucleic acid molecule 1300, reactive moieties 1312 and 1318 may be adjacent. Probe moieties 1306 and 1314 are linked by a linking sequence 1330. The ligation of 1306 to 1314 may be chemical or enzymatic as described elsewhere herein. As described elsewhere herein, the linking moiety (e.g., 1320 or 1321) may comprise a triazole moiety generated by reaction of an alkyne moiety and an azide moiety. The ligation reaction of reactive moieties 1312 and 1318 may involve the use of a catalyst such as a copper species or a strained alkene and may take place within or outside of a partition. In some cases, moieties 1312 and 1318 may be adjacent and may not comprise reactive moieties. In such cases, moieties 1312 and 1318 may be ligated enzymatically (e.g., using a ligase). In some instances, 1310 is ligated to 1340 at 1321 prior to ligation at 1320. In some instances, 1310 is ligated to 1340 at 1320 prior to ligation at 1321. In some instances, 1310 is ligated to 1340 at 1321 and 1320 simultaneously or substantially simultaneously. The circularized molecule 1350 may be barcoded as described in previously in FIG. 13A. Barcoded molecules or derivatives thereof may then be analyzed by, e.g., nucleic acid sequencing.

One or more processes of the presently disclosed method may be carried out within a partition (e.g., as described herein). For example, one or more processes selected from the group consisting of lysis, permeabilization, denaturation, hybridization, extension, duplication, and amplification of one or more components of a sample comprising the nucleic acid molecule may be performed within a partition. In some cases, multiple processes are carried out within a partition.

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or a cell comprising the nucleic acid molecule or a derivative thereof (e.g., a cell bead), as well as additional components (e.g., probes, nucleic acid barcode molecules, and reagents), may be provided within a partition. In some cases, the probes may be hybridized to the target regions of the nucleic acid molecule and linked or ligated to one another inside a partition. Alternatively, the probes may be hybridized to the target regions of the nucleic acid molecule and linked or ligated to one another outside of a partition. For example, the nucleic acid molecule or a cell comprising the nucleic acid molecule may be provided in a container other than a partition and undergo hybridization of the probes within the initial container or another container that is not a partition. In some cases, a cell may be permeabilized (e.g., as described herein) to provide access to the nucleic acid molecule of interest therein and hybridization of the probes to the target regions of the nucleic acid molecule of interest may take place within the cell. Ligation of the probes hybridized to the target regions of the nucleic acid molecule may then be initiated (e.g., under suitable conditions and through introduction of an appropriate catalyst) to provide a probe-linked nucleic acid molecule. For example, reaction between a first probe comprising an azide moiety and a second probe comprising an alkyne moiety may be catalyzed by a copper catalyst. Excess probes and catalyst may then be washed away and the cell may be partitioned (e.g., as described herein) for further analysis and processing. In another example, ligation of the hybridized probes may take place within a partition. Extension, denaturation, and/or amplification processes may also take place within a partition.

The nucleic acid molecule or a derivative thereof (e.g., a probe-linked nucleic acid molecule, a nucleic acid molecule having one or more probes hybridized thereto, a barcoded probe-linked nucleic acid molecule, or an extended nucleic acid molecule or complement thereof) or the cell comprising the nucleic acid molecule or a derivative thereof (e.g., a cell bead) may be co-partitioned with one or more reagents (e.g., as described herein) at any useful stage of the method. For example, the nucleic acid molecule or a derivative thereof contained within a cell may be co-partitioned with one or more reagents following generation of the probe-linked nucleic acid molecule. Similarly, the nucleic acid molecule or a derivative thereof or a cell comprising the nucleic acid molecule or a derivative thereof may be released from a partition at any useful stage of the method. For example, the nucleic acid molecule or a derivative thereof or a cell comprising the nucleic acid molecule or a derivative thereof may be released from the partition subsequent to hybridization of a binding sequence of a nucleic acid barcode molecule to a probe-linked nucleic acid molecule (e.g., to a sequence of a probe hybridized to the target region of the nucleic acid molecule) to provide a barcoded probe-linked nucleic acid molecule. In another example, release from the partition may take place subsequent to extension of the barcoded probe-linked nucleic acid molecule to provide an extended nucleic acid molecule that comprises a sequence complementary to the barcode sequence of a nucleic acid barcode molecule and one or more sequences complementary to one or more target regions of the nucleic acid molecule. Alternatively, the nucleic acid molecule or a derivative thereof or a cell comprising the nucleic acid molecule or a derivative thereof may be released from a partition subsequent to denaturation of an extended nucleic acid molecule from the nucleic acid molecule and the nucleic acid barcode molecule. Duplication and/or amplification of the extended nucleic acid molecule may then be carried out within a solution. In some cases, such a solution may comprise additional extended nucleic acid molecules and/or complements thereof generated through the same process carried out in different partitions. Each extended nucleic acid molecule or complement thereof (e.g., amplified product) may comprise a different barcode sequence or a sequence complementary to a different barcode sequence. In this instance, the solution may be a pooled mixture comprising the contents of two or more partitions (e.g., droplets).

One or more additional components such as one or more reagents may be co-partitioned with a nucleic acid molecule or derivative thereof or a cell comprising a nucleic acid molecule or a derivative thereof (e.g., as described in the preceding section).

In some cases, the methods described herein may be used to facilitate gene expression analysis. For example, a target nucleic acid molecule comprising a hybrid gene may be contacted by a plurality of different probes. One or more probes of the plurality of probes may have a sequence complementary to a first portion of the hybrid gene (e.g., a first target region), and one or more probes of the plurality of probes may have a sequence complementary to a second portion of the hybrid gene (e.g., a second target region) in proximity to the first portion of the hybrid gene. The two probes may each comprise a reactive moiety such that, upon hybridization to the hybrid gene and exposure to appropriate reaction conditions, the two probes may ligate to one another. The solution including the probe-ligated hybrid gene may undergo processing to remove unhybridized probes and may be partitioned with one or more reagents including one or more nucleic acid barcode molecules. A nucleic acid barcode molecule included within the partition including the probe-ligated hybrid gene may have a sequence complementary to a sequence of a probe hybridized to the hybrid gene and may hybridize thereto to generate a barcoded probe-ligated hybrid gene. Subsequent extension and amplification may take place within or outside of the partition. Following amplification to generate an amplified product comprising sequences of portions of the hybrid gene, or complements thereof, the amplified product may be detected using sequencing. Resultant sequence reads may be used to determine the components of the hybrid gene.

The presently disclosed method may be applied to a single nucleic acid molecule or a plurality of nucleic acid molecules. A method of analyzing a sample comprising a nucleic acid molecule may comprise providing a plurality of nucleic acid molecules (e.g., RNA molecules), where each nucleic acid molecule comprises a first target region and a second target region, a plurality of first probes, and a plurality of second probes. In some cases, one or more target regions of nucleic acid molecules of the plurality of nucleic acid molecules may comprise the same sequence. The first and second target regions of a nucleic acid molecule of the plurality of nucleic acid molecules may be adjacent to one another. The plurality of first probes may each comprise a first probe sequence complementary to the sequence of a first target region of a nucleic acid molecule of the plurality of nucleic acid molecules as well as a second probe sequence. A first probe sequence of a first probe of the plurality of first probes may comprise a first reactive moiety. One or more first probes of the plurality of first probes may comprise the same first probe sequence and/or the same second probe sequence. The plurality of second probes may each comprise a third probe sequence complementary to the sequence of a second target region of a nucleic acid molecule of the plurality of nucleic acid molecules. The plurality of second probes may further comprise a fourth probe sequence. A third probe sequence of a second probe of the plurality of second probes may comprise a second reactive moiety. One or more probes of the second probes of the plurality of second probes may comprise the same third probe sequence and/or, if present, the same fourth probe sequence. A first probe sequence of a first probe of the plurality of first probes may hybridize to first target region of a nucleic acid molecule of the plurality of nucleic acid molecules. A third probe sequence of a second probe of the plurality of second probes may hybridize to the second target region of a nucleic acid molecule of the plurality of nucleic acid molecules. The first and third probe sequences hybridized to the first and second target regions, respectively, of a nucleic acid molecule of the plurality of nucleic acid molecules may be adjacent to one another such that a first reactive moiety of the first probe sequence is adjacent to a second reactive moiety of the third probe sequence. The first and second reactive moieties of the first and second probes hybridized to nucleic acid molecules of the plurality of nucleic acid molecules may react to provide a plurality of probe-linked nucleic acid molecules. A binding sequence of a nucleic acid barcode molecule of a plurality of nucleic acid barcode molecules may hybridize to the second probe sequence of a first probe of the plurality of first probes that is hybridized to a first target region of a nucleic acid molecule of a plurality of nucleic acid molecules or a probe-linked nucleic acid molecule of the plurality of probe-linked nucleic acid molecules. Each nucleic acid barcode molecule of the plurality of nucleic acid barcode molecules may comprise a barcode sequence and a second binding sequence. The barcode sequence of each nucleic acid barcode molecule of the plurality of nucleic acid barcode molecules may be the same or different. Following hybridization of a binding sequence of a nucleic acid barcode molecule of the plurality of nucleic acid barcode molecules to a second probe sequence of a first probe of the plurality of first probes that is hybridized to a first target region of a nucleic acid molecule of the plurality of nucleic acid molecules or a probe-linked nucleic acid molecule of the plurality of probe-linked nucleic acid molecules, each first probe of the plurality of hybridized probes may then be extended from an end of the probe to an end of the nucleic acid barcode molecule to which it is hybridized (e.g., an end of the second binding sequence of the nucleic acid barcode molecule). A plurality of extended nucleic acid molecules may thereby be created, where each extended nucleic acid molecule of the plurality of extended nucleic acid molecules comprises a sequence complementary to the first target region of a nucleic acid molecule of the plurality of nucleic acid molecules, a sequence complementary to the second target region of a nucleic acid molecule of the plurality of nucleic acid molecules, a second probe sequence of a first probe of the plurality of first probes, a sequence complementary to a barcode sequence of a nucleic acid barcode molecule of the plurality of nucleic acid barcode molecules, and one or more sequences complementary to one or more additional sequences (e.g., binding or barcode sequences) of a nucleic acid barcode molecule of the plurality of nucleic acid barcode molecules.

In some cases, one or more processes described above may be performed within a partition. For example, each nucleic acid molecule of the plurality of nucleic acid molecules may be provided within a different partition. This may be achieved by partitioning a plurality of cells comprising the plurality of nucleic acid molecules within a plurality of separate partitions, where each cell comprises a target nucleic acid molecule and each partition of a plurality of different partitions of the plurality of separate partitions comprises a single cell. The plurality of cells may be partitioned prior or subsequent to hybridization of probes to target regions of the nucleic acid molecules of interest included therein and linking of the probes to provide probe-linked nucleic acid molecules. Access to a target nucleic acid molecule or derivative thereof (e.g., as described herein) contained within a cell in a partition may be provided by lysing or permeabilizing the cell (e.g., as described herein). Nucleic acid barcode molecules provided within each partition of the plurality of different partitions of the plurality of separate partitions may be provided attached to beads. For example, each partition of the plurality of different partitions of the plurality of separate partitions may comprise a bead comprising a plurality of nucleic acid barcode molecules attached thereto (e.g., as described herein). The plurality of nucleic acid barcode molecules attached to each bead may comprise a different barcode sequence, such that each partition of the plurality of different partitions of the plurality of separate partitions comprises a different barcode sequence. Upon release of components from the plurality of different partitions of the plurality of separate partitions (e.g., following extension of each probe), each extended nucleic acid molecule may comprise a sequence complementary to a different barcode sequence, such that each extended nucleic acid molecule can be traced to a given partition and, in some cases, a given cell.

Figure 14:
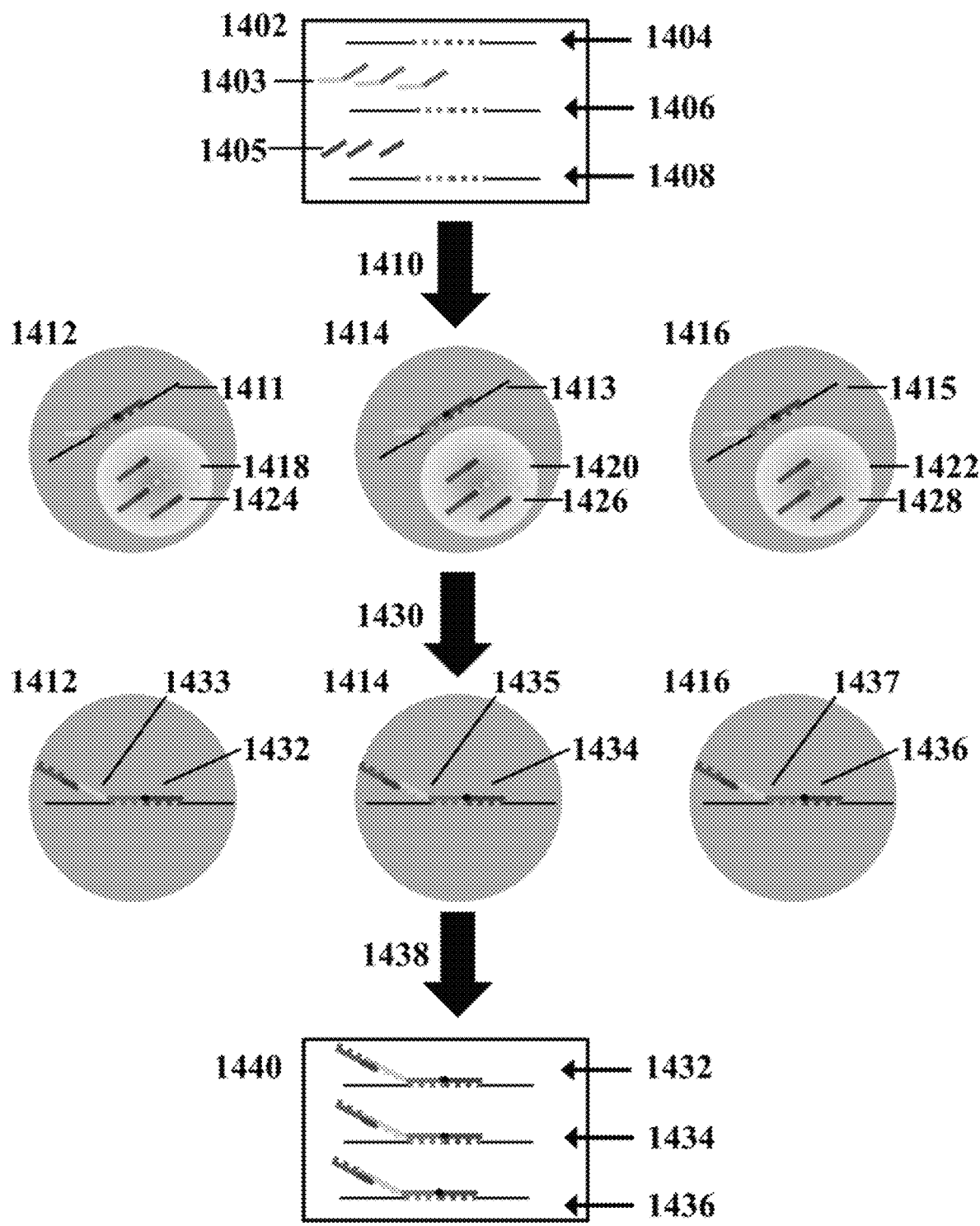
FIG. 14 shows a sample workflow for analysis of a plurality of nucleic acid molecules involving co-partitioning nucleic acid molecules with barcoded beads within droplets.

FIG. 14 illustrates a sample workflow for a method of analyzing a plurality of nucleic acid molecules comprising chemical-ligation mediated amplification. Nucleic acid molecules 1404, 1406, and 1408 are provided within container 1402. Each nucleic acid molecule comprises a first target region and a second target region indicated by dashed lines. The first target regions of each nucleic acid molecule may be the same or different. Similarly, the second target regions of each nucleic acid molecule may be the same or different. A plurality of first probes 1403 and a plurality of second probes 1405 may be provided in container 1402. First probes of the plurality of first probes 1403 may comprise a first probe sequence that is complementary to the first target region of nucleic acid molecule 1404, 1406, and/or 1408 and a second probe sequence. First probe sequences of the plurality of first probes 1403 may comprise a first reactive moiety. Second probes of the plurality of second probes 1405 may comprise a third probe sequence that is complementary to the second target region of nucleic acid molecule 1404, 1406, and/or 1408. Third probe sequences of the plurality of second probes 1405 may comprise a second reactive moiety. A first probe sequence of first probes of the plurality of first probes 1403 may hybridize to the first target regions of nucleic acid molecules 1404, 1406, and 1408. Similarly, a second probe sequence of second probes of the plurality of second probes 1405 may hybridize to the second target regions of nucleic acid molecules 1404, 1406, and 1408. The first and second reactive moieties of the first and third probe sequences may then react to provide probe-linked nucleic acid molecules 1411, 1413, and 1415.

In process 1410, probe-linked nucleic acid molecules 1411, 1413, and 1415 may be co-partitioned with beads 1418, 1420, and 1422 into separate droplets 1412, 1414, and 1416 such that each droplet includes a single probe-linked nucleic acid molecule and a single bead. Each bead may comprise a plurality of nucleic acid barcode molecules attached thereto. Bead 1418 comprises nucleic acid barcode molecule 1424, bead 1420 comprises nucleic acid barcode molecule 1426, and bead 1422 comprises nucleic acid barcode molecule 1428. Nucleic acid barcode molecules 1424, 1426, and 1428 each comprise first and second binding sequences and a barcode sequence. The barcode sequences of nucleic acid barcode molecules 1424, 1426, and 1428 are different such that each droplet comprises a different barcode sequence.

In process 1430, nucleic acid barcode molecules 1424, 1426, and 1428 are released from their respective beads (e.g., by application of a stimulus that degrades or dissolves the bead) within their respective droplets. A binding sequence of nucleic acid barcode molecules 1424, 1426, and 1428 hybridizes to the second probe sequence of probe-linked nucleic acid molecules 1411, 1413, and 1415, respectively, to provide a barcoded probe-linked nucleic acid molecule within each droplet. The barcoded probe-linked nucleic acid molecule within each droplet then undergoes extension to provide complexed extended nucleic acid molecules 1432, 1434, and 1436 comprising extended nucleic acid molecules 1433, 1435, and 1437. Extended nucleic acid molecules 1433, 1435, and 1437 comprise sequences complementary to a barcode sequence and the sequences of the target regions of the nucleic acid molecule from which they derive. For example, extended nucleic acid molecule 1433 comprises sequences complementary to the sequences of the target regions of nucleic acid molecule 1404 and a sequence complementary to the barcode sequence of nucleic acid barcode molecule 1424.

In process 1438, the contents of droplets 1412, 1414, and 1416 are pooled to provide a pooled mixture 1440 comprising complexed extended nucleic acid molecules 1432, 1434, and 1436. Complexed extended nucleic acid molecules 1432, 1434, and 1436 may then be denatured from the nucleic acid molecule and nucleic acid barcode molecule to which they are hybridized to provide extended nucleic acid molecules 1433, 1435, and 1437. Extended nucleic acid molecules 1433, 1435, and 1437 may then be amplified to provide amplified products corresponding to each extended nucleic acid molecule. The amplified products will comprise sequences that are the same or substantially the same as the barcode sequence and sequences of the target regions of the nucleic acid molecule from which they derive. For example, the amplified product corresponding to extended nucleic acid molecule 1433 comprises sequences that are the same or substantially the same as the sequences of the target regions of nucleic acid molecule 1404 and a sequence that is the same or substantially the same as the barcode sequence of nucleic acid barcode molecule 1424. Because each extended nucleic acid molecule and each amplified product comprises a different barcode sequence or complement thereof, the extended nucleic acid molecules and amplified products can be traced back to particular nucleic acid molecules and, in some cases, to particular cells. This barcoding method may therefore facilitate rapid analysis of nucleic acid molecules through, for example, sequencing without the need for reverse transcription.

In one aspect, the present invention provides methods of analysis that target specific sequences (e.g., RNA sequences) with a molecular inversion probe. In one embodiment, the molecular inversion probe can form a circularized nucleic acid molecule upon hybridization to target specific sequences.

Figure 18:
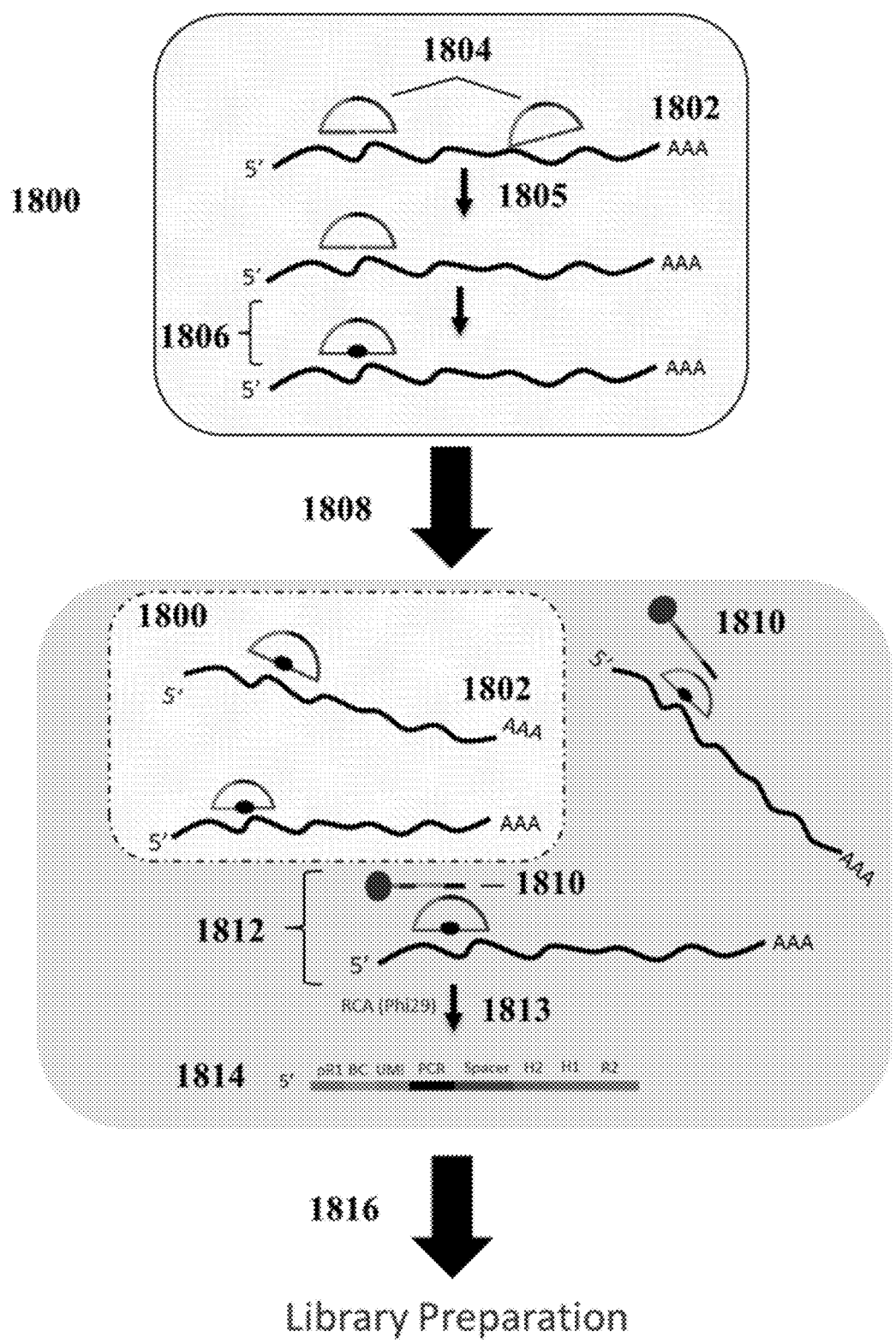
FIG. 18 schematically shows a method of analyzing a nucleic acid molecule.

FIG. 18 illustrates an example workflow for a method of analyzing a plurality of nucleic acid molecules comprising enzymatic ligation-mediated amplification. 1800 is a fixed and permeabilized cell comprising nucleic acid molecules 1802. Each nucleic acid molecule 1802 comprises a first target region and a second target region. The first target regions of each nucleic acid molecule may be the same or different. Similarly, the second target regions of each nucleic acid molecule may be the same or different. The first and second target regions of each nucleic acid molecule may be adjacent to one another. A plurality of first probes 1804 comprising first and second probe sequences that hybridize with the first and second target regions, respectively, may be introduced into the cell 1800. The probes 1804 may be provided as linear molecules and may comprise adapter sequences such as a PCR primer region, a sequencing site primer region, and/or a spacer region, as described elsewhere herein. The first probe sequence of the plurality of probes 1804 may hybridize to the first target regions of nucleic acid molecules 1802. Upon hybridization of the probes to the target regions, a circularized nucleic acid molecule may be formed. Similarly, the second probe sequence of the plurality of probes 1804 may hybridize to the second target regions of nucleic acid molecules 1802. In some cases, the first probe sequence and the second target probe sequence are adjacent to each other. In some cases, they are non-adjacent and may be ligated using polymerases, e.g., Mu polymerase, as described elsewhere herein. In some cases, the first and second probe sequences of probes 1804 comprise reactive moieties. Following hybridization, excess, unhybridized probes may be removed via a wash step 1805. The first and second probe sequences may then be connected via introduction of enzymes (e.g., polymerases, ligases) or through a chemical reaction (e.g., click chemistry of reactive moieties), generating a probe-linked nucleic acid molecule 1806.

In process 1808, probe-linked nucleic acid molecules 1806 within cell 1800 may be co-partitioned with barcode nucleic acid molecules 1810. The barcode nucleic acid molecules may comprise adaptor regions including, but not limited to, a unique molecular identifier sequence, a PCR primer sequence, a spacer sequence, and sequencing site primer region. The barcode nucleic acid molecules may be attached to beads (not shown). Each bead may comprise a plurality of nucleic acid barcode molecules attached thereto. A binding sequence of nucleic acid barcode molecule 1810 hybridizes to a sequence of the probe 1804 of the probe-linked nucleic acid molecules 1806, to provide a barcoded probe-linked nucleic acid molecule 1812. The barcoded probe-linked nucleic acid molecule 1812 then undergoes a nucleic acid reaction 1813 such as amplification, e.g., Phi29-based rolling circle amplification, to provide barcoded amplicons of interest 1814, which comprise sequences complementary to the sequences of the target regions of nucleic acid molecule 1802, a sequence complementary to the barcode sequence of nucleic acid barcode molecule 1810, and any adaptor sequences of probe 1804.

In process 1816, the contents of the one or more partitions are pooled. Barcoded amplicons of interest 1814 may then be subjected to conditions sufficient for library preparation. In some cases, the barcoded amplicons of interest may be subjected to nucleic acid reactions, such as amplification (e.g., PCR). The amplified products will comprise sequences that are the same or substantially the same as the barcode sequence and sequences of the target regions of the nucleic acid molecule from which they derive. The amplified products can be traced back to particular nucleic acid molecules and, in some cases, to particular cells. This barcoding method may therefore facilitate rapid analysis of nucleic acid molecules through, for example, sequencing without the need for reverse transcription.

Figure 19:
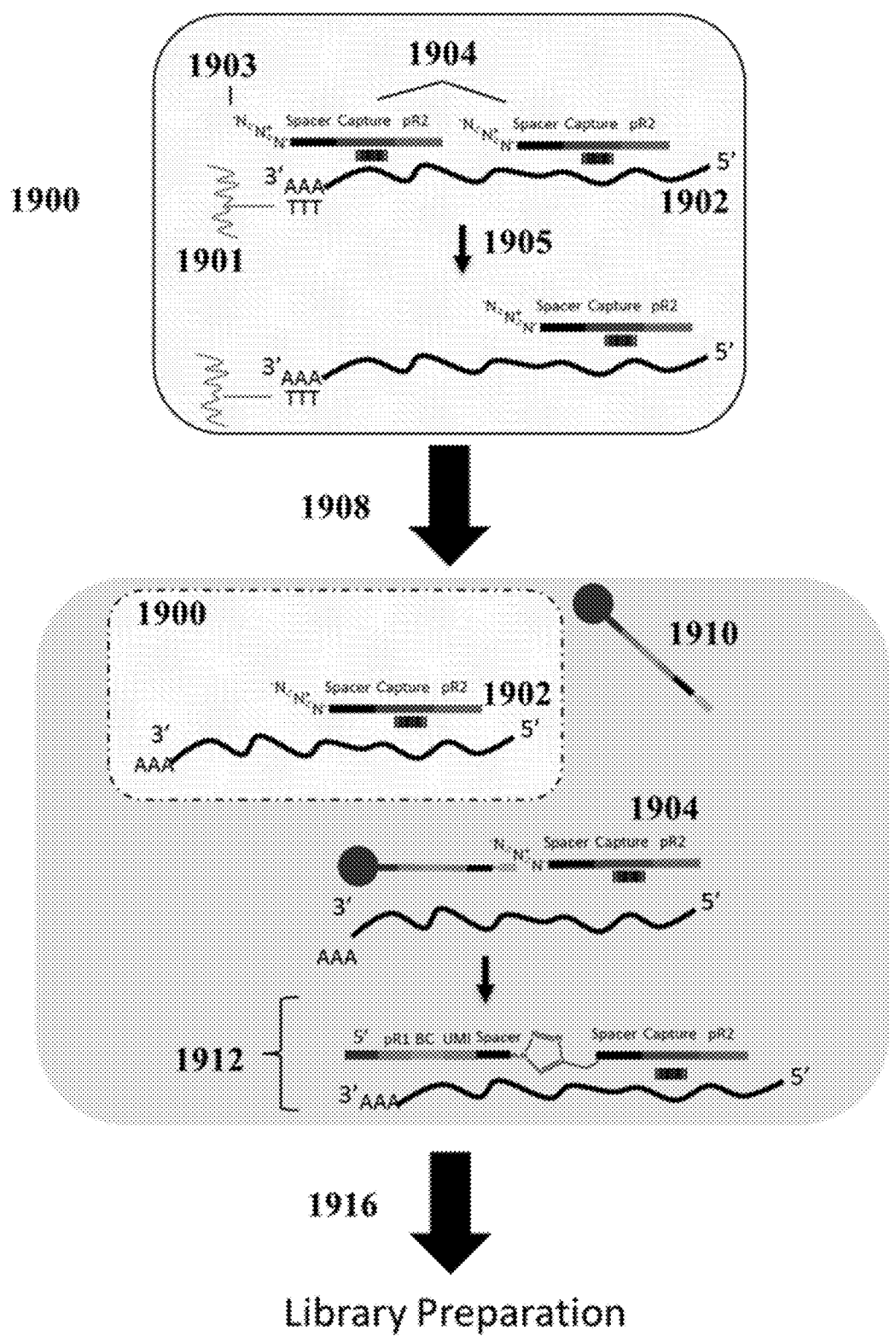
FIG. 19 schematically shows another example method of analyzing a nucleic acid molecule.

FIG. 19 illustrates an example workflow for a method of analyzing a plurality of nucleic acid molecules comprising chemical ligation-mediated amplification of nucleic acids in cell beads. 1900 is a cell bead comprising dissolvable nucleic acid molecule capture moieties 1901. These moieties may be thioacrydite-conjugated nucleic acid molecules that are bound to the gel bead matrix. Within the cell bead are nucleic acid molecules 1902, which comprise a target region. A plurality of first probes 1904 comprising a probe sequence that hybridizes with the target region, respectively, may be introduced into the cell bead 1900. The probes 1904 may additionally comprise adapter sequences such as a PCR primer region, a sequencing site primer region, and/or a spacer region, as described elsewhere herein. The probes 1904 may also comprise a reactive moiety 1903. Following hybridization, excess, unhybridized probes may be removed via a wash step 1905.

In process 1908, the cell bead 1900 comprising nucleic acid molecules 1902 is co-partitioned with barcode nucleic acid molecules 1910 which comprise a reactive moiety. The partition comprises conditions sufficient to release the nucleic acid molecules 1902 from the cell bead matrix. In some cases, a reducing agent such as DTT may be used to release the nucleic acid molecules from the cell bead into the partition. The barcode nucleic acid molecules may be attached to beads (not shown). Each bead may comprise a plurality of nucleic acid barcode molecules attached thereto. The partition may comprise conditions sufficient to release the nucleic acid barcode molecules from the beads into the partition. The barcode nucleic acid molecule 1910 may associate with the probe 1904 that is hybridized to the nucleic acid molecule 1902. The barcode nucleic acid molecule 1910 and the probe 1904 may then be ligated, e.g., via click chemistry of the reactive moieties on the barcode nucleic acid molecule and the reactive moiety on the probe 1904, to provide a barcoded, probe-linked nucleic acid molecule 1912. Reaction yield may be enhanced, for example, by incorporating splint nucleic acid sequences that hybridize with the spacer adapter sequences. For example, the barcode nucleic acid molecule 1910 may comprise a sequence (e.g., overhang sequence, not shown) that may hybridize with an adapter sequence (e.g., spacer sequence) on the probe 1904. Following hybridization, the reactive moieties on the barcode nucleic acid molecule 1910 and the reactive moiety on the probe 1904 may be ligated to provide a barcoded, probe-linked nucleic acid molecule. In other non-limiting examples, the barcode nucleic acid molecule 1910 may be partially double-stranded and comprise a sequence (e.g., overhang sequence) to form a splint nucleic acid sequence that can partially hybridize with the probe 1904 and be ligated to provide a barcoded, probe-linked nucleic acid molecule that is partially double-stranded.

In process 1916, the contents of the one or more partitions are pooled. The barcoded probe-linked nucleic acid molecules 1912 may then be subjected to conditions sufficient for library preparation. In some cases, the barcoded probe-linked nucleic acid molecules are cleaned up. In a non-limiting example of cleanup, samples may be enriched or purified via a magnetic-based pulldown assay of the of nucleic acid molecules. In some cases, the cleanup process may allow for size selection of nucleic acid molecules. In some cases, the cleanup process comprises removing DNA-templated ligation products. In other cases, the cleanup process comprises RNAse to cleave the RNA strand, e.g., in a DNA-RNA duplex. In some cases, the cleanup process comprises a pulldown assay (e.g., biotin pulldown of a ligation handle). In some cases, the cleanup process comprises post-ligation exonuclease treatment. In some cases, the cleanup process comprises, blocking free 3' ends on nucleic acid molecules, which may render them non-extendable by polymerase. In some cases, the probe-linked nucleic acid molecules may be subjected to nucleic acid reactions, such as amplification (e.g., PCR). The amplified products will comprise sequences that are the same or substantially the same as the barcode sequence and sequences of the target regions of the nucleic acid molecule from which they derive. The amplified products can be traced back to particular nucleic acid molecules and, in some cases, to particular cells. This barcoding method may therefore facilitate rapid analysis of nucleic acid molecules through, for example, sequencing without the need for reverse transcription.

In some embodiments, a target-specific probe (e.g., the probe-linked molecules described herein) hybridized to a sample nucleic acid molecule (e.g., a cellular mRNA molecule) may be barcoded through combinatorial assembly of barcode segments using, e.g., a split-pool approach. For example, a plurality of permeabilized cells (or permeabilized nuclei or cell beads) are contacted with one or more target-specific probes as described herein. Panel 11A of FIG.

11 depicts a target specific probe hybridized to a target mRNA molecule 1100. The target-specific probe(s) may be configured using any suitable methodology described elsewhere herein (see, e.g., FIGS. 9-12, 14, 16, 17, molecular inversion probes, etc.). For example, in some instances, a first probe comprising binding sequence 1105 and adapter sequence 1106 and a second probe comprising binding sequence 1104 and adapter sequence 1103 is hybridized to target nucleic acid molecule 1100 (e.g., a mRNA molecule) and the two probes are linked using, e.g., the enzymatic and/or chemical ligation schemes described elsewhere herein to generate a probe linked nucleic acid molecule 1120. Binding sequence 1105 is configured to hybridize to target region 1101 of target nucleic acid molecule 1100 while binding sequence 1104 is configured to hybridize to target region 1102 of target nucleic acid molecule 1100. Adapter sequences 1106 and 1103 may each optionally comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Probe-linked nucleic acid molecule 1120 may then be barcoded using a combinatorial assembly of barcode sequence segments (i.e., barcode subunits). For example, in some embodiments, probe-linked nucleic acid molecule 1120 is combinatorially barcoded using a split pool approach. In some embodiments, probe-linked nucleic acid molecule 1120 is combinatorially barcoded by successive addition of barcode sequence segments. A combinatorial barcode sequence may be synthesized by various methods including, for example, ligation, hybridization, nucleotide polymerization, or a combination thereof.

Panel 11B shows addition of a first barcode sequence segment to probe-linked nucleic acid molecule 1120. A partially double-stranded nucleic acid barcode molecule comprising (i) a first strand 1108 comprising a first barcode sequence segment and an adapter sequence and (ii) a second strand 1107 comprising a binding sequence is hybridized to probe-linked nucleic acid molecule 1120. The binding sequence is complementary to at least a portion of adapter sequence 1106 such that the nucleic acid barcode molecule hybridizes to probe-linked nucleic acid molecule 1120. Strand 1108 is then attached to probe-linked nucleic acid molecule 1120 (e.g., using ligation and/or nucleic acid extension) to add the first barcode sequence segment.

Panel 11C shows addition of a second barcode sequence segment to probe-linked nucleic acid molecule 1120 comprising the nucleic acid barcode molecule comprising 1108. A partially double-stranded nucleic acid barcode molecule comprising (i) a first strand 1110 comprising a first barcode sequence segment and an adapter sequence and (ii) a second strand 1109 comprising a binding sequence is hybridized to probe-linked nucleic acid molecule 1120 comprising the nucleic acid barcode molecule comprising 1108. The binding sequence is complementary to at least a portion of the adapter sequence such that the nucleic acid barcode molecule hybridizes to probe-linked nucleic acid molecule 1120 comprising the nucleic acid barcode molecule comprising 1108. Strand 1110 is then attached to probe-linked nucleic acid molecule 1120 comprising the nucleic acid barcode molecule comprising 1108 (e.g., using ligation and/or nucleic acid extension) to add the second barcode sequence segment.

Panel 11D shows addition of a third barcode sequence segment to probe-linked nucleic acid molecule 1120 comprising 1108 and 1110. A partially double-stranded nucleic acid barcode molecule comprising (i) a first strand 1112 comprising a first barcode sequence segment and an adapter sequence and (ii) a second strand 1111 comprising a binding sequence is hybridized to probe-linked nucleic acid molecule 1120 comprising 1108 and 1110. The binding sequence is complementary to at least a portion of the adapter sequence such that the nucleic acid barcode molecule hybridizes to probe-linked nucleic acid molecule 1120 comprising 1108 and 1110. Strand 1112 is then attached to probe-linked nucleic acid molecule 1120 comprising 1108 and 1110 (e.g., using ligation and/or nucleic acid extension) to add the third barcode sequence segment.

The combinatorial barcoding scheme described above can be implemented using, e.g., a split-pool approach. For example, a plurality of permeabilized cells (or permeabilized nuclei or cell beads) comprising, e.g., probe-linked nucleic acid molecule 1120 (or any other probe described herein) may be partitioned into a first plurality of partitions (e.g., a plurality of wells) wherein each partition of the plurality of partitions comprises a different (i.e., unique) first barcode sequence segment. After addition of the first barcode sequence segment, cells (or nuclei or cell beads) can be collected from the first plurality of partitioned and pooled and partitioned into a second plurality of partitions (e.g., a plurality of wells) wherein each partition of the plurality of partitions comprises a different (i.e., unique) second barcode sequence segment. Repeating this split-pool process allows the generation of barcodes comprising any suitable amount of barcode sequence segments. Combinatorial barcoding as described herein may comprise at least 1, 2, 3, 4, 5, 6, 7, 8 or more operations (e.g., split-pool cycles). Combinatorial barcoding comprising multiple operations may be useful, for example, in generation of greater barcode diversity and to synthesize a unique barcode sequence on nucleic acid molecules derived from each single cell of a plurality of cells. For example, combinatorial barcoding comprising three operations, each comprising attachment of a unique nucleic acid sequence in each of 96 partitions, will yield up to 884,736 unique barcode combinations. Cells may be partitioned such that at least one cell (or nuclei or cell bead) is present in each partition of a plurality of partitions. Cells may be partitioned such that at least 1; 2; 3; 4; 5; 10; 20; 50; 100; 500; 1,000; 5,000; 10,000; 100,000; 1,000,000; or more cells are present in a single partition. Cells may be partitioned such that at most 1,000,000; 100,000; 10,000; 5,000; 1,000; 500; 100; 50; 20; 10; 5; 4; 3; 2; or 1 cell is present in a single partition. Cells may be partitioned in a random configuration.

In some instances, the methods described herein are performed in a cell bead. See, e.g., U.S. Pat. Pub. 2018/0216162 and U.S. Pat. Pub. 2019/0100632 for exemplary cell bead generation and processing methods. For example, in some embodiments, a cell bead comprising a cell is generated as described elsewhere herein. In some instances, the cell bead comprises, attached thereto (e.g., covalently attached to the cell bead polymer or cross-linked matrix), a plurality of nucleic acid molecules comprising a poly-T sequence. In some instances, the nucleic acid molecules comprising a poly-T sequence are releasably attached to the c el bead (e.g., via a labile bond as described elsewhere herein). Nucleic acid molecules comprising a poly-T sequence may also comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), a barcode sequence, UMI sequence, or complements of these sequences). Cells in the cell bead may then be lysed to release cellular constituents, including mRNA molecules comprising a poly-A tail. Alternatively, cells may be lysed prior to or concurrent with cell bead generation (e.g., in droplets prior to or concurrent with cell bead generation). Poly-A containing mRNA may then be hybridized to the poly-T sequence, thereby immobilizing mRNA in the cell bead. In some instances, captured mRNA is subjected to a reverse transcription reaction to convert captured mRNA into cDNA. In some instances, the cDNA is single stranded. In other instances, the cDNA is double stranded. Nucleic acid molecules immobilized in cell beads, can then be contacted by the probe molecules described herein and processed to detect cellular nucleic acid molecules (such as mRNA) as described herein. In some instances, the cell bead is used to contain cellular DNA during DNA denaturation by heat or chemical denaturation. The probes described above can be used to target and detect DNA sequences, analogous to the description above.

Also provided herein are methods that may involve cell multiplexing. Cells may be processed, partitioned, and labeled. Processed cells may be pooled and nucleic acid molecules from the cells may be further processed. One or more of the processes may involve a nucleic acid reaction, barcoding, partitioning, and/or any combinations or derivatives thereof. One or more of the methods disclosed herein may allow for cell multiplexing without the use of staining reagents and may result in improved occupancy of partitions. One or more of the processes may involve hybridizing a probe to a target region of a nucleic acid molecule of interest, barcoding the resultant complex, and performing an extension, denaturation, and amplification processes to provide nucleic acid molecules comprising a sequence the same or substantially the same as or complementary to that of the target region of the nucleic acid molecule of interest.

A multiplexing method may comprise hybridizing a first probe and a second probe to first and second target regions of the nucleic acid molecule, linking the first and second probes to provide a probe-linked nucleic acid molecule, and barcoding the probe-linked nucleic acid molecule. One or more processes of the methods provided herein may be performed within a partition such as a droplet or well.

In other cases, a multiplexing method may comprise hybridizing a first probe to a first target region of a nucleic acid molecule, barcoding the first probe within a first partition with a first barcode sequence, recovering the barcoded first probe from the partition, partitioning the first probe hybridized to the first target region of the nucleic acid molecule within a second partition, hybridizing a second probe to a second target region of the nucleic acid molecule within the second partition, and barcoding the first or second probe hybridized to the nucleic acid molecule with a second barcode sequence. In some cases, the first probe may comprise the first barcode sequence and barcoding with a first barcode sequence within the first partition may be simultaneous with hybridizing the first probe to the first target region. In some cases, the second probe may comprise the second barcode sequence and barcoding with a second barcode sequence may be simultaneous with hybridizing the second probe to the second target region. In some cases, the first probe may be linked to the second probe (e.g., via a chemical or enzymatic ligation process, as described herein). The first and second probes may be linked to one another within the second partition or outside of the second partition. This process may be repeated for a plurality of nucleic acid molecules (e.g., nucleic acid molecules included within cells, such as fixed cells or cell beads) across a plurality of first partitions and a plurality of second partitions. Each first partition of the plurality of first partitions may comprise a different first barcode sequence of a plurality of first barcode sequences, and each second partition of the plurality of second partitions may comprise a different second barcode sequence of a plurality of second barcode sequences. First barcode sequences may be components of first nucleic acid barcode molecules coupled to a first plurality of beads, while second barcode sequences may be components of second nucleic acid barcode molecules coupled to a second plurality of beads (e.g., as described herein). The plurality of first partitions may be wells, while the second plurality of partitions may be droplets (e.g., as described herein).

In an aspect, a multiplexing method provided herein comprises, (i) fixing a plurality of cells or cell beads, (ii) performing a first partitioning of the plurality of cells or cell beads, (iii) barcoding a plurality of nucleic acid molecules within the plurality of cells or cell beads to provide a plurality of labeled cells or cell beads comprising barcoded nucleic acid molecules, (iv) pooling the plurality of labeled cells or cell beads comprising the barcoded nucleic acid molecules, (v) performing a second partitioning of said plurality of labeled cells or cell beads comprising the barcoded nucleic acid molecules, and (vi) performing a second barcoding of the barcoded nucleic acid molecules to produce multiplexed barcoded nucleic acid molecules.

In some embodiments, the cell or cell bead may be processed to barcode the cell. The cell bead may comprise a cell. In some embodiments, the cell may be alive. In some embodiments, the cell may be fixed using a fixative agent such as paraformaldehyde, formaldehyde, ethanol, methanol, etc. In some cases, the fixed cell may also be permeabilized. In some embodiments, a plurality of cells (e.g., fixed, permeabilized cells) may be partitioned among a plurality of partitions. In some cases, a cell (e.g., a fixed cell) is permeabilized within a partition. Within the plurality of partitions, the plurality of cells (e.g., fixed, permeabilized cells) may be barcoded. In some embodiments, nucleic acid molecules within the plurality of cells (e.g., fixed, permeabilized cells) may be barcoded.

In some cases, the method may comprise providing a sample comprising a nucleic acid molecule (e.g., an RNA molecule) having adjacent first and second target regions; a first probe having a first probe sequence that is complementary to the first target region and a second probe sequence; and a second probe having a third probe sequence that is complementary to the second target region. The first and third probe sequences may also comprise first and second reactive moieties, respectively. Upon hybridization of the first probe sequence of the first probe to the first target region of the nucleic acid molecule, and hybridization of the third probe sequence of the second probe to the second target region of the nucleic acid molecule, the reactive moieties may be adjacent to one another. Subsequent reaction between the adjacent reactive moieties under sufficient conditions may link the first and second probes to yield a probe-linked nucleic acid molecule. The probe-linked nucleic acid molecule may also be referred to as a probe-ligated nucleic acid molecule. The probe-linked nucleic acid molecule may then be barcoded with a barcode sequence of a nucleic acid barcode molecule to provide a barcoded probe-linked nucleic acid molecule. Barcoding may be achieved by hybridizing a binding sequence of the nucleic acid barcode molecule to the second probe sequence of the first probe of the probe-linked nucleic acid molecule. In some cases, the first probe or the second probe may comprise a barcode sequence. In some cases, both the first probe and the second probe comprise a barcode sequence. In some cases, the first probe and the second probe may be parts of the same probe and may be connected. In some cases, the first probe and the second probe may be parts of a linear probe that forms a circularized nucleic acid product upon hybridization of the first probe and the second probe with the target nucleic acid molecule. The barcoded nucleic acid molecule may be subjected to amplification reactions to yield an amplified product comprising the first and second target regions and the barcode sequence or sequences complementary to these sequences. One or more processes may be performed within a partition such as a droplet or well.

In some cases, the method may comprise providing a sample comprising a nucleic acid molecule (e.g., an RNA molecule) having first and second target regions; a first probe having a first probe sequence that is complementary to the first target region and a second probe sequence; and a second probe having a third probe sequence that is complementary to the second target region. The first and second target regions may be adjacent to one another. Alternatively, the first and second target regions may be separated by a gap region of at least one nucleotide, such as at least 1, 10, 50, or 100 nucleotides. The first probe sequence of the first probe may hybridize to the first target region of the nucleic acid molecule, and the third probe sequence of the second probe may hybridize to the second target region of the nucleic acid molecule to provide a probe-associated nucleic acid molecule. Subsequent to hybridization of the first probe sequence of the first probe to the first target region of the nucleic acid molecule, and hybridization of the third probe sequence of the second probe to the second target region of the nucleic acid molecule, the first and second probes may be linked to one another (e.g., via a chemical or enzymatic ligation process, as described herein). For example, the first probe may comprise a first reactive moiety and the second probe may comprise a second reactive moiety, and the first and second reactive moieties may react under sufficient conditions may link the first and second probes to yield a probe-linked nucleic acid molecule. The probe-linked nucleic acid molecule may also be referred to as a probe-ligated nucleic acid molecule. The probe-linked nucleic acid molecule may then be barcoded with a barcode sequence of a nucleic acid barcode molecule to provide a barcoded probe-linked nucleic acid molecule. Alternatively, the probe-associated nucleic acid molecule may be barcoded to provide a barcoded probe-associated nucleic acid molecule. Barcoding may be achieved by hybridizing a binding sequence of the nucleic acid barcode molecule to the second probe sequence of the first probe of the probe-linked nucleic acid molecule. In some cases, the first probe or the second probe may comprise a barcode sequence. In some cases, both the first probe and the second probe comprise a barcode sequence. In some cases, the first probe and the second probe may be parts of the same probe and may be connected (e.g., by one or more linking sequences, as described herein). In some cases, the first probe and the second probe may be parts of a linear probe that forms a circularized nucleic acid product upon hybridization of the first probe and the second probe with the target nucleic acid molecule. The barcoded nucleic acid molecule may be subjected to amplification reactions to yield an amplified product comprising the first and second target regions and the barcode sequence or sequences complementary to these sequences. One or more processes may be performed within a partition such as a droplet or well.

In some cases, a second barcoding operation may be performed to generate multiplexed barcoded nucleic acid molecules. The operation may comprise (i) pooling a plurality of cells, wherein a cell of the plurality of cells comprises a barcoded nucleic acid molecule, (ii) partitioning the plurality of cells, and (iii) barcoding the barcoded nucleic acid molecule to produce a multiplexed barcoded nucleic acid molecule. One or more processes may be performed within a partition such as a droplet or well. In some cases, pooling of the cells comprising the barcoded nucleic acid molecule may be performed in a container, such as a vessel or a tube. The pooled cells may then be further partitioned. The partition may comprise conditions sufficient to barcode the barcoded nucleic acid molecule to generate a multiplexed barcoded nucleic acid molecule. In some cases, the conditions comprise a barcode molecule and an enzyme. In some cases, the conditions comprise a barcode molecule, an adapter molecule, and an enzyme. The enzyme may be a ligase, polymerase, or any other suitable enzyme or combinations of enzymes. In one non-limiting example, a cell comprising a barcoded nucleic acid molecule may be partitioned with an adapter molecule comprising a probe-binding sequence and a barcode-binding sequence. In some cases, the partition also comprises a barcode molecule and an enzyme. In some cases, the probe-binding sequence of the adapter molecule may hybridize with a sequence on the barcoded nucleic acid molecule. In some cases, the barcode-binding sequence of the adapter molecule may hybridize with a sequence of the barcode molecule. The barcode molecule may then be adjacent to the barcoded nucleic acid molecule. The barcode molecule may then be ligated (e.g., using an enzyme) to the barcoded nucleic acid molecule, generating a multiplexed barcoded nucleic acid molecule. The multiplexed barcoded nucleic acid molecules may be used to determine cellular occupancy in a partition and may provide a method for improved cellular loading, increased occupancy, determination of multiply-occupied partitions, and may obviate the need for cell staining reagents.

Figure 22A:
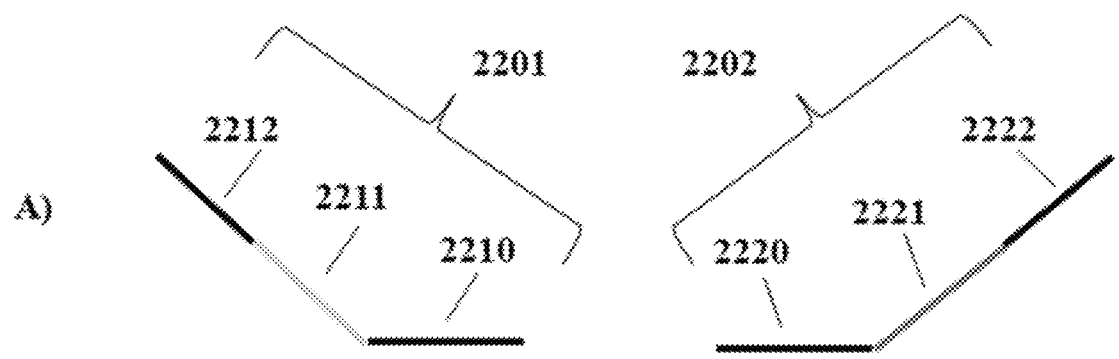
FIGS. 22A-C illustrates a method for multiplexed barcoding.
Figure 22B:
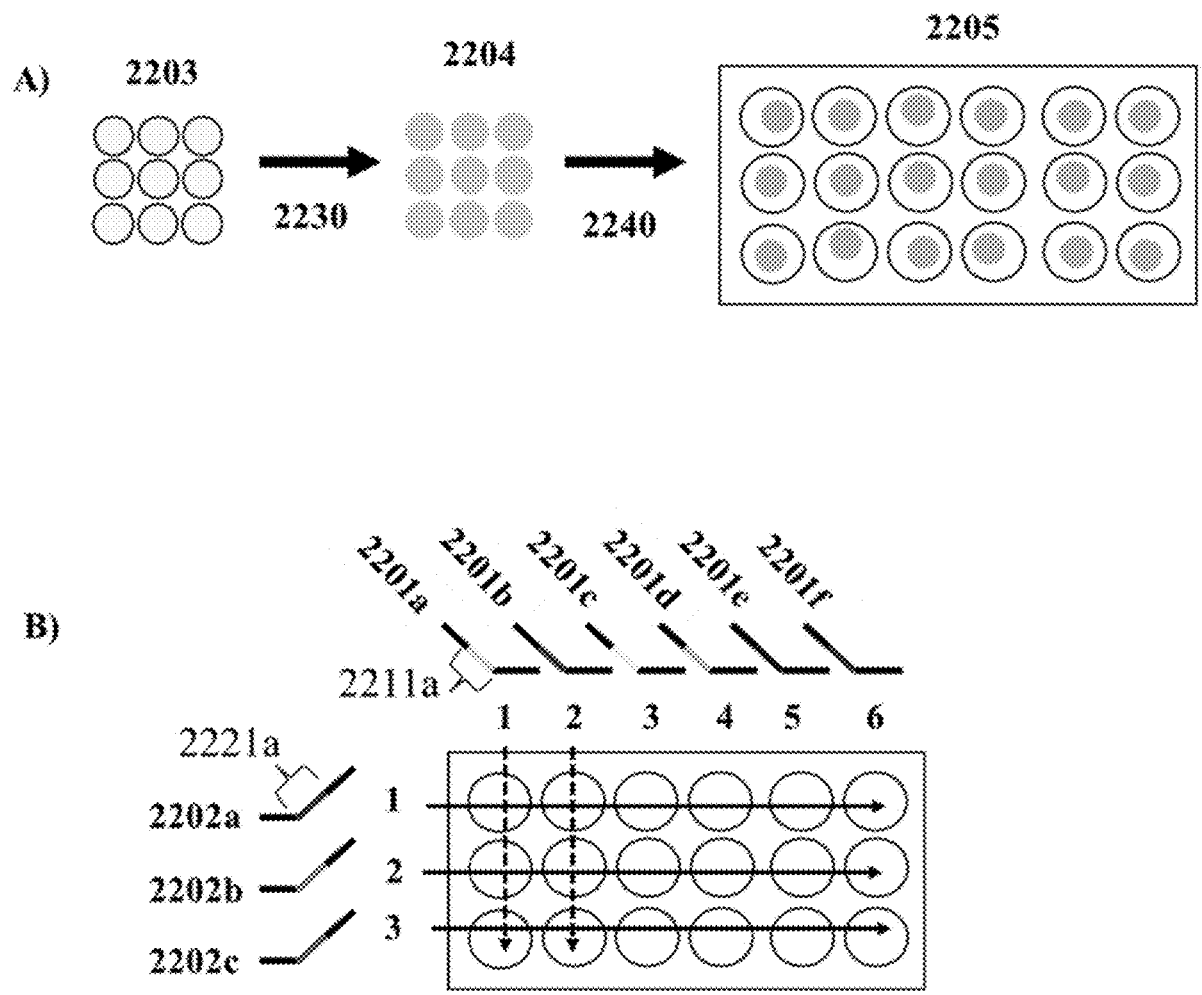
Figure 22C:
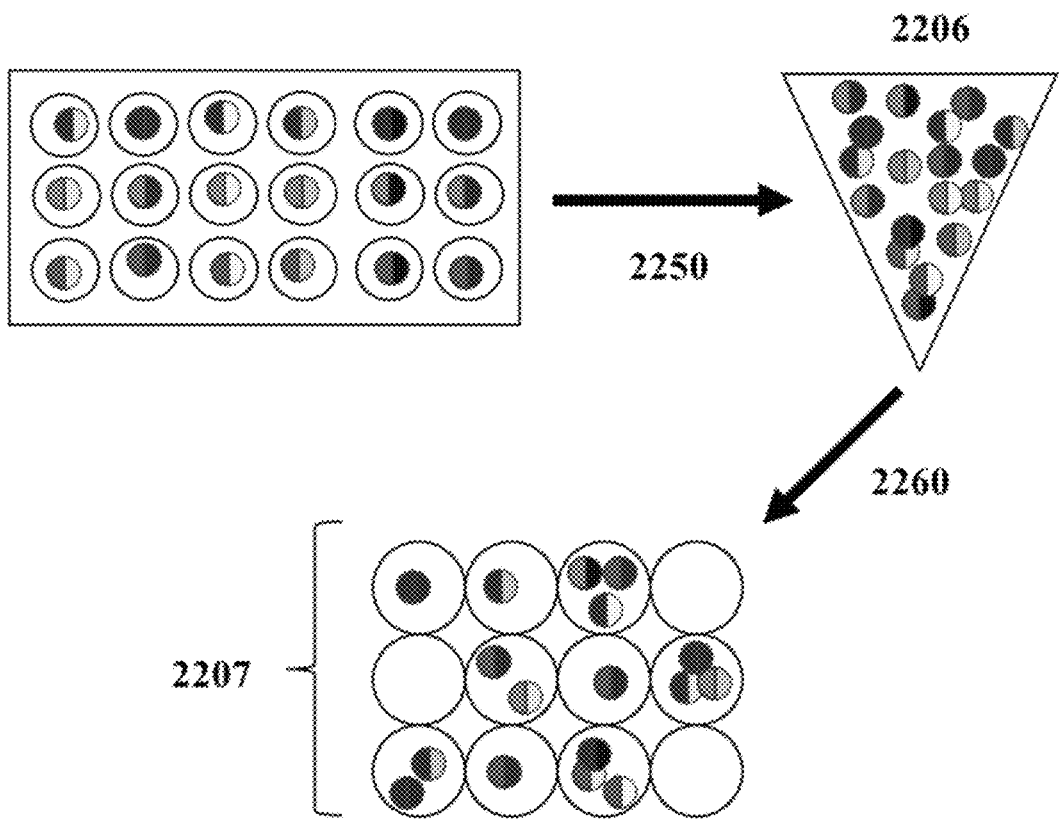
Figure 22C:
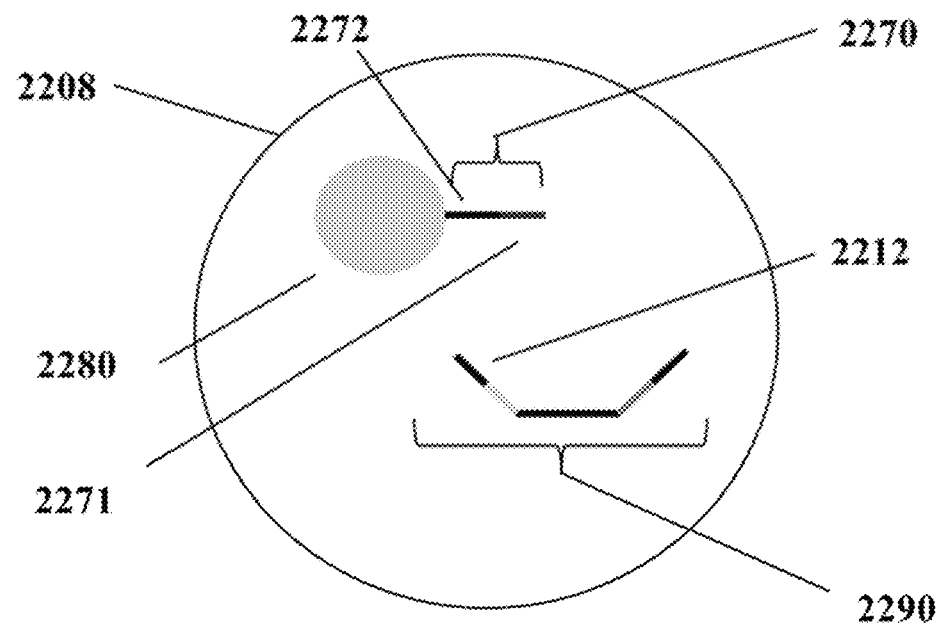

In some embodiments, the probes described herein (e.g., 1206, 2014, 1305, 1310, 1340, 1706, etc.) comprise a barcode sequence. In some instances, target nucleic acid molecules (e.g., mRNA molecules) within a cell (e.g., a fixed and/or permeabilized cell) are contacted with barcoded probes to facilitate cell multiplexing and/or more robust and efficient analysis of cellular polynucleotides. For example, FIGS. 22A-C schematically illustrates a method for improved processing nucleic acid molecules from a cell. Panel 22A illustrates exemplary barcoded probes (2201, 2202) that may be utilized with the methods described herein. Probe 2201 comprises probe sequences 2210, barcode sequence 2211, and adapter sequence 2212. Probe 2202 comprises probe sequences 2220, barcode sequence 2221, and adapter sequence 2222. Probe sequences 2210 and 2220 are complementary to a target region of a cellular polynucleotide (e.g., mRNA molecule) as described elsewhere herein. In some instances, probes 2201 and/or 2202 may comprise a reactive moiety (e.g., click chemistry moiety) as described elsewhere herein. In some cases, probes 2201 and 2202 are ligated chemically (e.g., click chemistry), and in other cases, enzymatically (e.g., a ligase, such as SplintR or T4 ligase) to generate a probe-linked nucleic acid molecule comprising sequences 2212, 2211, 2210, 2220, 2221, and 2222.

Panel A of FIG. 22B illustrates schematically an exemplary partitioning and processing scheme. A plurality of cells 2203 may be fixed and/or permeabilized in process 2230 to provide processed cells 2204. In some instances, cells 2203 are first partitioned followed by in-partition fixation and/or permeabilization. In process 2240, cells 2203 or 2204 are partitioned into a plurality of partitions, e.g., into wells of a multiwell array 2205. In some instances, each partition (e.g., well of a multiwell array) comprises a single cell. In other embodiments, each partition (e.g., well of a multiwell array) comprises a plurality of cells. For example, cells may be partitioned such that are 1; 2; 3; 4; 5; 10; 20; 50; 100; 500; 1,000; 5,000; 10,000; 100,000; 1,000,000; or more cells are present in a single partition. Cells may be partitioned such that at least 1; 2; 3; 4; 5; 10; 20; 50; 100; 500; 1,000; 5,000; 10,000; 100,000; 1,000,000; or more cells are present in a single partition. Cells may be partitioned such that at most 1,000,000; 100,000; 10,000; 5,000; 1,000; 500; 100; 50; 20; 10; 5; 4; 3; 2; or 1 cell is present in a single partition.

Barcoded probes are distributed into the partitions (either prior to, concurrent with, or subsequent to cell partitioning) such that each partition comprises probes comprising a partition-specific probe barcode. For example, in some instances, barcoded probes (e.g., 2201 and 2202) are partitioned into rows and columns as described in FIG. 22B, Panel B. In FIG. 22B, Panel B, barcoded probes (e.g., 2201) are distributed such that each well in a column of microwell array 2205 comprises a common barcode sequence (e.g., 2211) while each well in different columns of microwell array 2205 comprises probes (e.g., 2201) comprising different barcode sequences (e.g., 2211). For example, each well in column 1 will comprise probe molecule 2201a comprising target sequence 2210 and column barcode sequence 2211a. Likewise, each well in column 2 will comprise probe molecule 2201b comprising target sequence 2210 and column barcode sequence 2211b; while each well in column 3 will comprise probe molecule 2201c comprising target sequence 2210 and column barcode sequence 2211c, etc. Similarly, probe 2202 is distributed such that each well in a row of microwell array 2205 comprises a common barcode sequence 2221 while each well in different rows of microwell array 2205 will comprise probes 2202 comprising different barcode sequences 2221. For example, each well in row 1 will comprise probe molecule 2202a comprising target sequence 2220 and row barcode sequence 2221a. Likewise, each well in row 2 will comprise probe molecule 2202b comprising target sequence 2220 and row barcode sequence 2221b while each well in row 3 will comprise probe molecule 2202c comprising target sequence 2220 and row barcode sequence 2221c, etc. Thus, each well of microwell array 2205 comprises a unique partition barcode comprising column barcode sequence (e.g., 2211a-f) and a row barcode sequence (e.g., 2221a-c).

In this fashion, barcoded probe molecules specific for a panel of target polynucleotides (e.g., a panel of mRNA molecules) can be co-partitioned with cells, e.g., in the column and row format described above. For example, each well in column 1 may comprise a plurality of barcoded probe molecules (e.g., 2201) comprising a plurality of target sequences (e.g., 2210a, 2210b, 2210c, etc.) complementary to a plurality of cellular polynucleotides (e.g., a panel of mRNA molecules) and column barcode sequence 2211a. Likewise, each well in column 2 will comprise a plurality of probe molecules (e.g., 2201) comprising a plurality of target sequences (e.g., 2210a, 2210b, 2210c, etc.) complementary to the plurality of cellular polynucleotides (e.g., panel of mRNA molecules), but with column barcode sequence 2211b, etc. Similarly, each well in row 1 will comprise a plurality of barcoded probe molecules (e.g., 2202) comprising a plurality of target sequences (e.g., 2220a, 2220b, 2220c, etc.) complementary to the plurality of cellular polynucleotides (e.g., the panel of mRNA molecules) and row barcode sequence 2221a. Likewise, each row in column 2 will comprise a plurality of barcoded probe molecules (e.g., 2202) comprising a plurality of target sequences (e.g., 2220a, 2220b, 2220c, etc.) complementary to the plurality of cellular polynucleotides (e.g., the panel of mRNA molecules) and row barcode sequence 2221b, etc.

In some instances, only one of probe 2201 or 2202 will comprise a barcode sequence and probes 2201 and 2202 are partitioned such that each partition comprises a unique barcode sequence.

After co-partitioning of cells (e.g., 2204) and barcoded probes (e.g., 2201 and 2202), probes are hybridized to their target nucleic acid, unbound probes are optionally washed away, and probes are enzymatically (e.g., by ligation) or chemically (e.g., click chemistry) joined as previously described (see, e.g., FIG. 12 and accompanying text). In some instances, probes 2201 and 2202 are subjected to a gap-fill reaction as previously described (see, e.g., FIG. 16 and accompanying text). As schematically shown in FIG. 22C, Panel A, after processing of barcoded probes (e.g., chemical or enzymatic ligation), cells are pooled in process 2250 to provide a pooled plurality of cells 2206. The pooled plurality of cells 2206 may then be partitioned in process 2260 into a second set of partitions 2207 (e.g., droplets or wells) such that at least some partitions comprise (1) one or more cells of the pooled plurality of cells; and (2) nucleic acid barcode molecules. The cells are then processed to barcode the linked probe molecules as described elsewhere herein. In some instances, each partition may comprise a unique nucleic acid barcode molecule. Partitions 2207 may also comprise lysis reagents for lysis and release of the barcoded probes from cells. In one example, as shown in FIG. 22C, Panel B, a partition 2208 of the plurality of partitions 2207 comprises a bead comprising nucleic acid barcode molecules (e.g., 2270) attached thereto. In some instances, the bead is a gel bead as described elsewhere herein.

As shown in FIG. 22C, Panel B, nucleic acid barcode molecule 2270 comprises an adapter sequence 2271, and a barcode sequence 2272 (which optionally may comprise a UMI sequence), and binding sequence 2271, which is complementary to adapter sequence 2212 of the linked probe 2290. The adapter sequence 2271 may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), or complements of these sequences). Nucleic acid barcode molecule 2270 is then hybridized to sequence 2212 of the probe-linked nucleic acid molecule 2290. A barcoded probe-linked nucleic acid molecule is then generated using, e.g., a nucleic acid extension reaction and/or ligation reaction as described previously. The barcoded probe-linked nucleic acid molecule will comprise both the probe-specific barcode (e.g., 2211 and/or 2221) as well as the partition specific barcode 2272. Because of the presence of both the probe-specific barcode(s) (e.g., 2211 and/or 2221) and the partition specific barcode 2272, partitions comprising cell multiplets (e.g., cell doublets, triplets, etc.) could then be computationally deconvolved into single cells and this data retained where it typically would be discarded. Thus, in some instances, cells are "overloaded" into partitions using conditions such that a higher probability of cell multiplets (2,3,4,5+ cells per partition) are formed, wherein target libraries of these cell multiplets are computationally deconvolved into single cells.

After the partition-based barcoding step (FIG. 22C, Panel B), the contents of the partitions 2207 may be pooled and the barcoded probe-linked nucleic acid molecules may be duplicated or amplified by, for example, one or more amplification reactions, which may in some instances be isothermal. The amplification reactions may comprise polymerase chain reactions (PCR) and may involve the use of one or more primers or polymerases. The one or more primers may comprise one or more functional sequences (e.g., a primer sequence/primer binding sequence, a sequencing primer sequence (e.g., R1 or R2), a partial sequencing primer sequence (e.g., partial R1 or partial R2), a sequence configured to attach to the flow cell of a sequencer (e.g., P5 or P7, or partial sequences thereof), etc.) and may facilitate addition of said one or more functional sequences to the extended nucleic acid molecule. The barcoded probe-linked nucleic acid molecule, or a derivative thereof, may be detected via nucleic acid sequencing (e.g., as described herein).

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
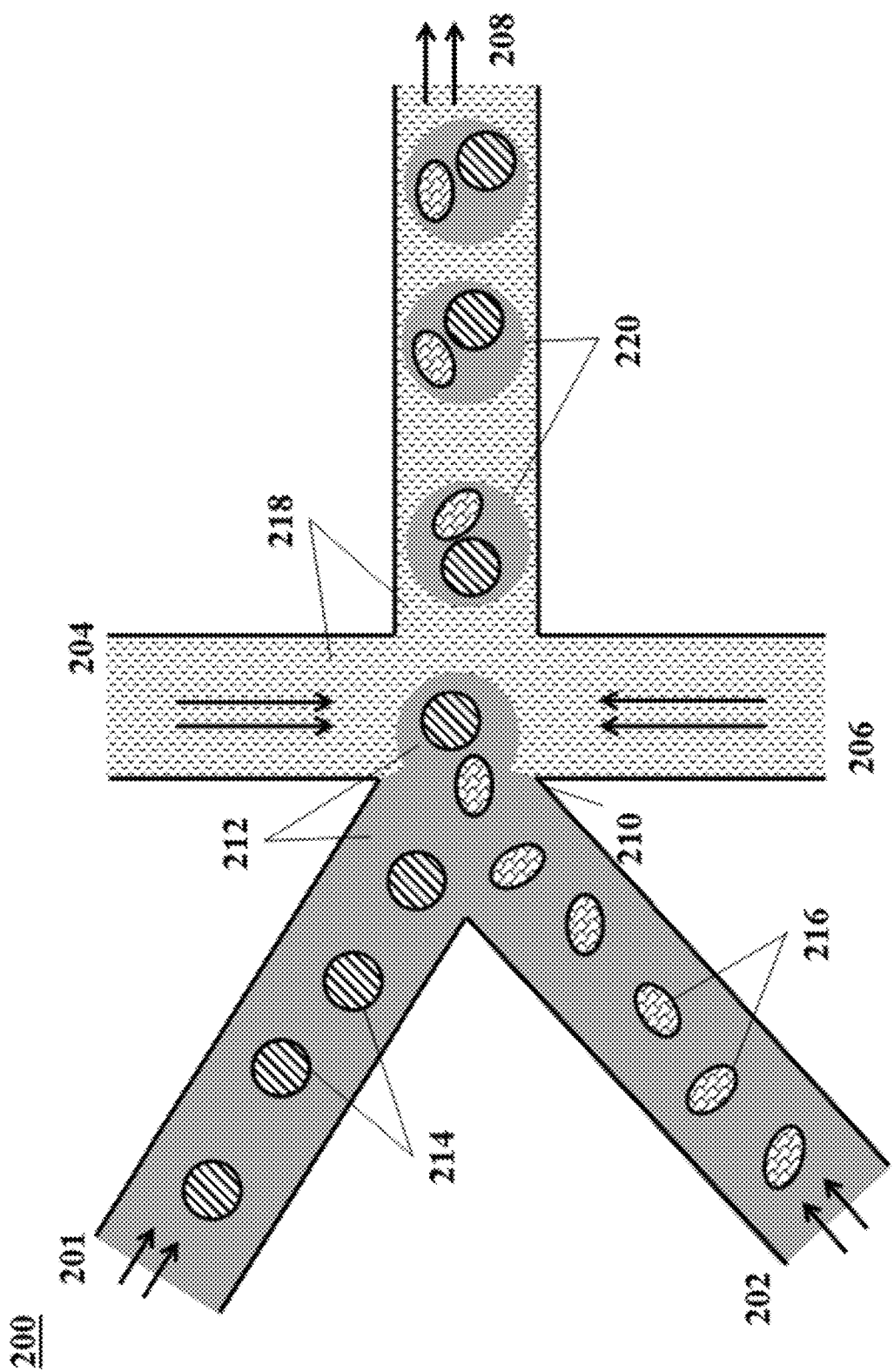
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
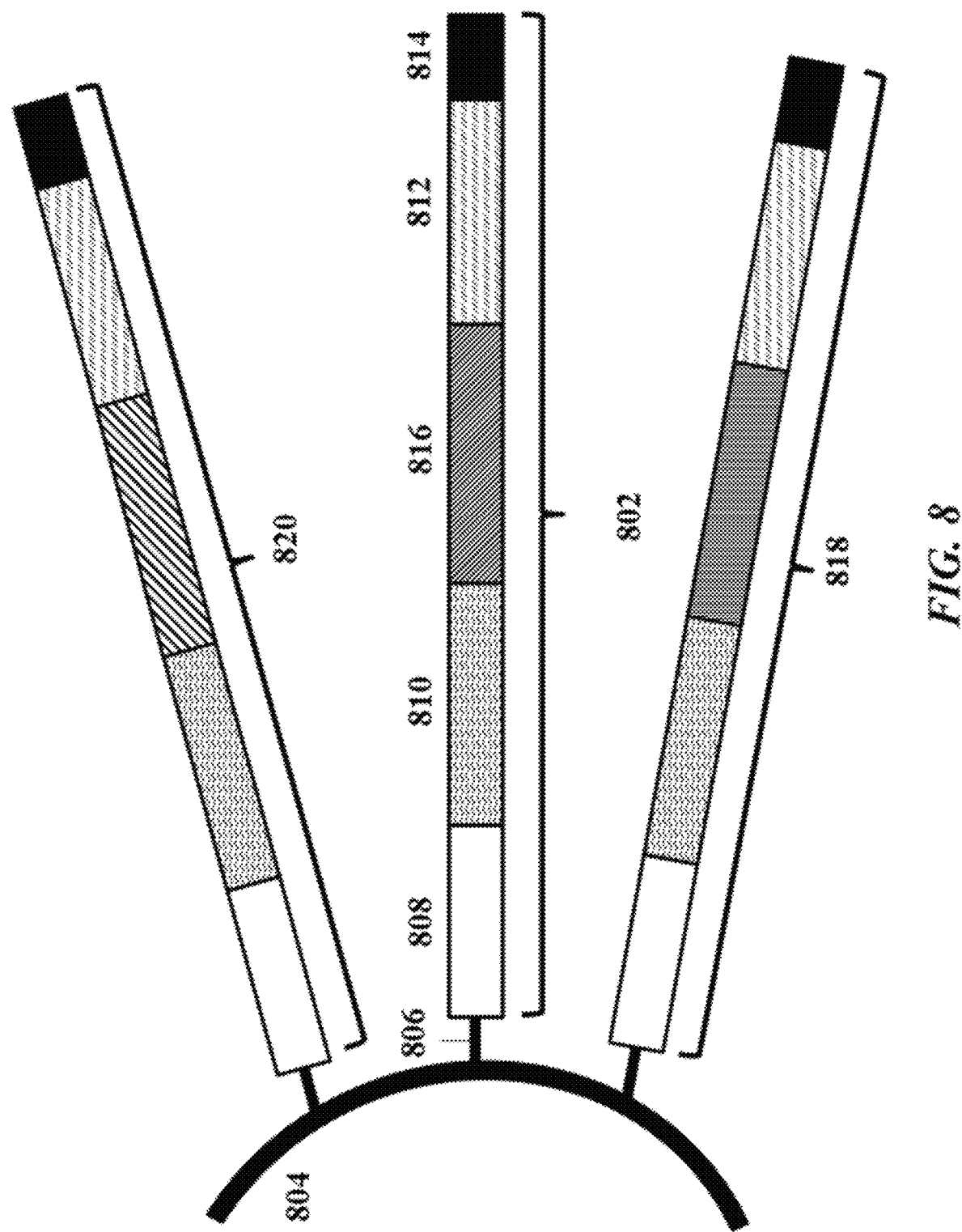
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of an mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 14, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
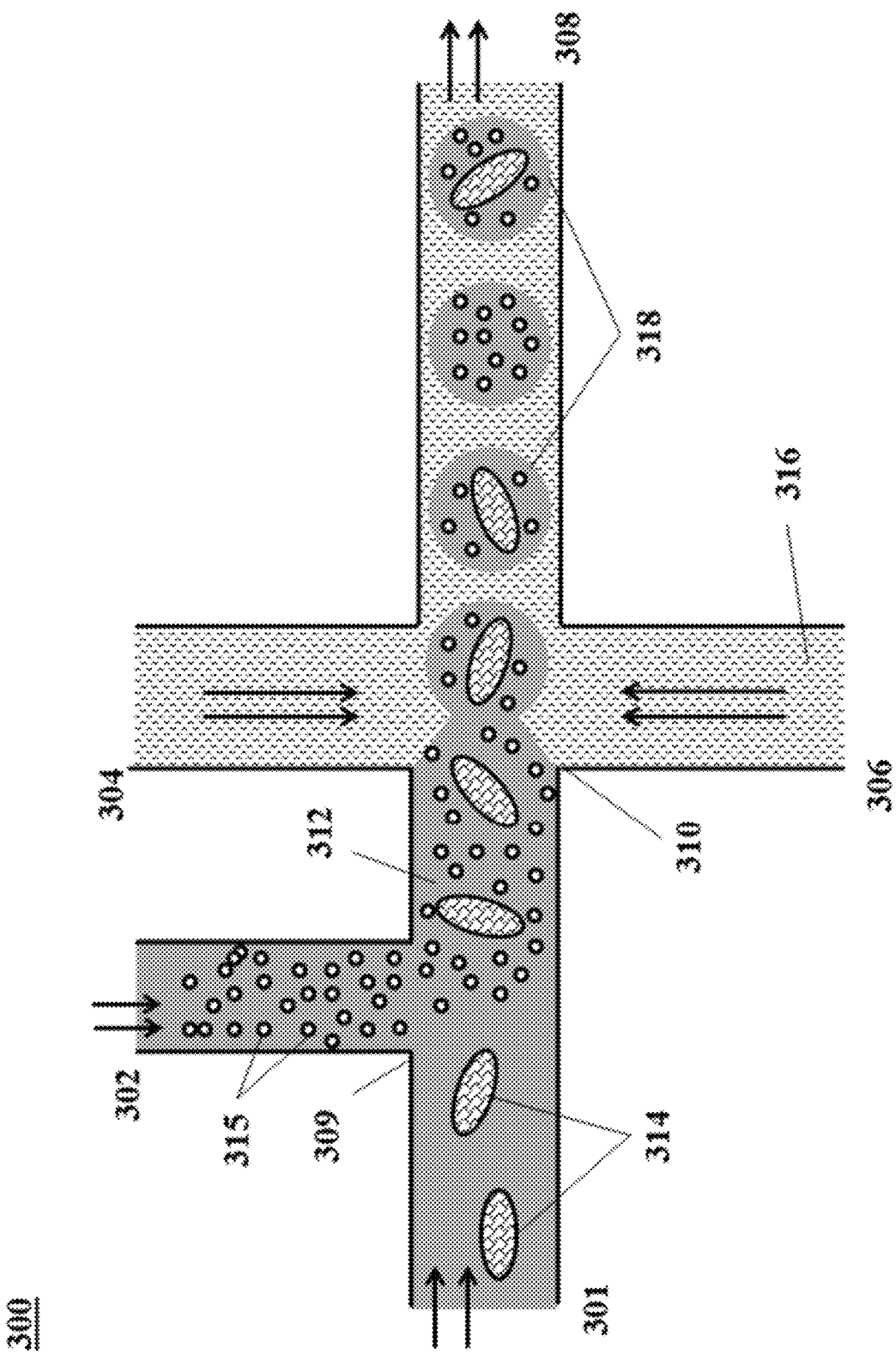
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particles's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
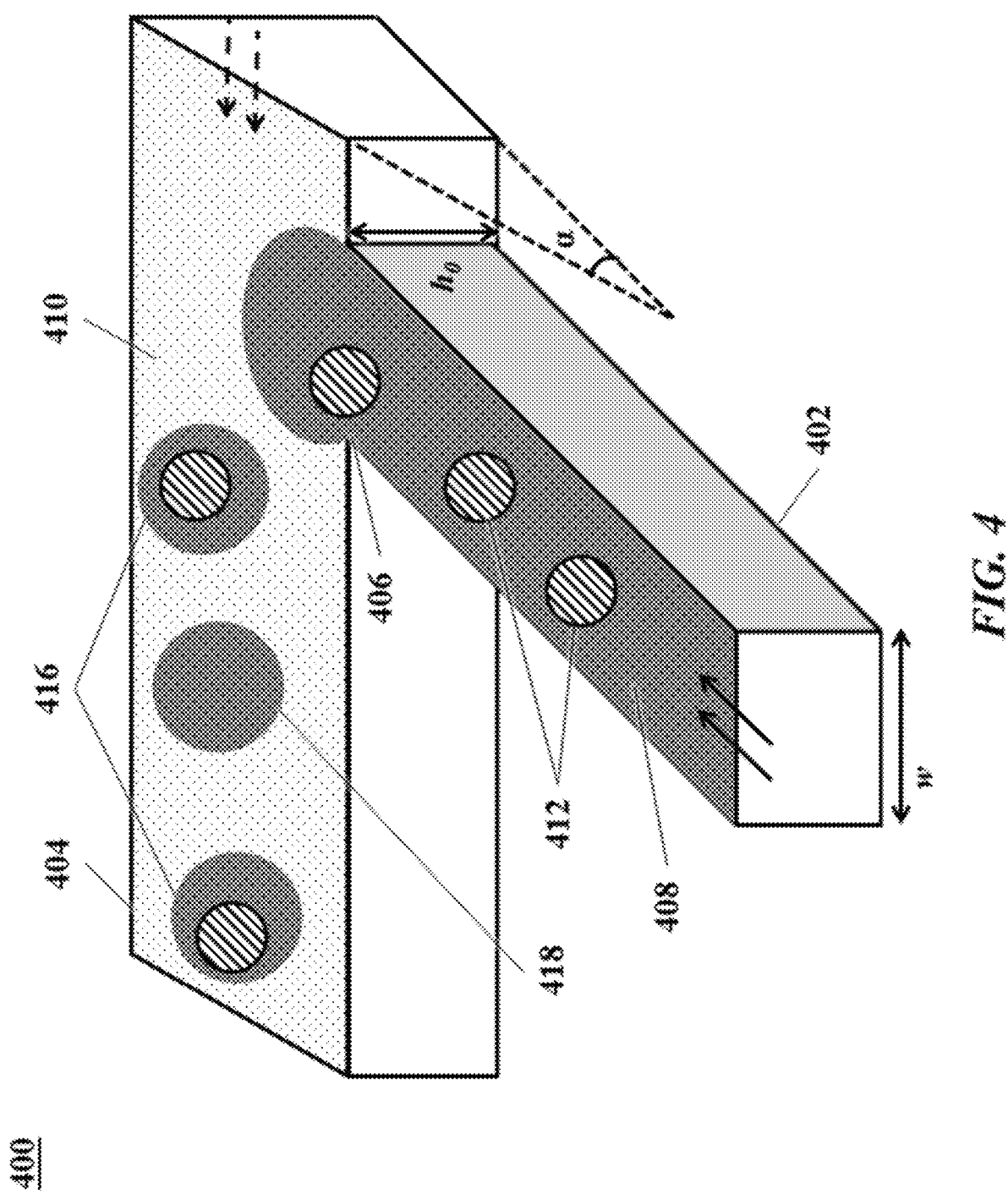
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, a. The expansion angle, a, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, Rd, may be predicted by the following equation for the aforementioned geometric parameters of $h_0$, w, and $\alpha$:

$$R_d \approx 0.44\left(1 + 2.2\sqrt{\tan\tan\alpha}\,\frac{w}{h_0}\right)\frac{h_0}{\sqrt{\tan\tan\alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, a, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
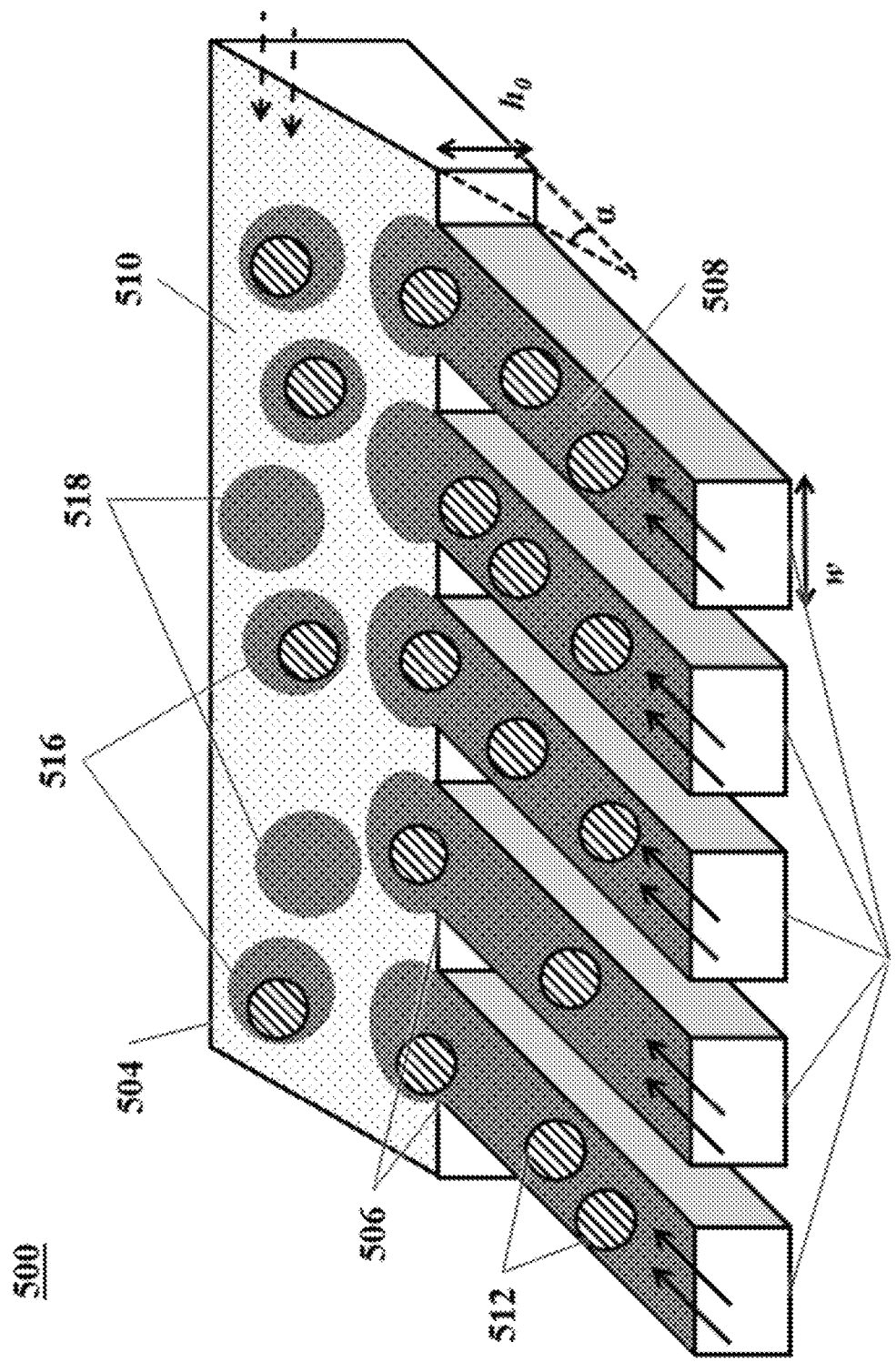
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, $\alpha$, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same.

The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and $\alpha$, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
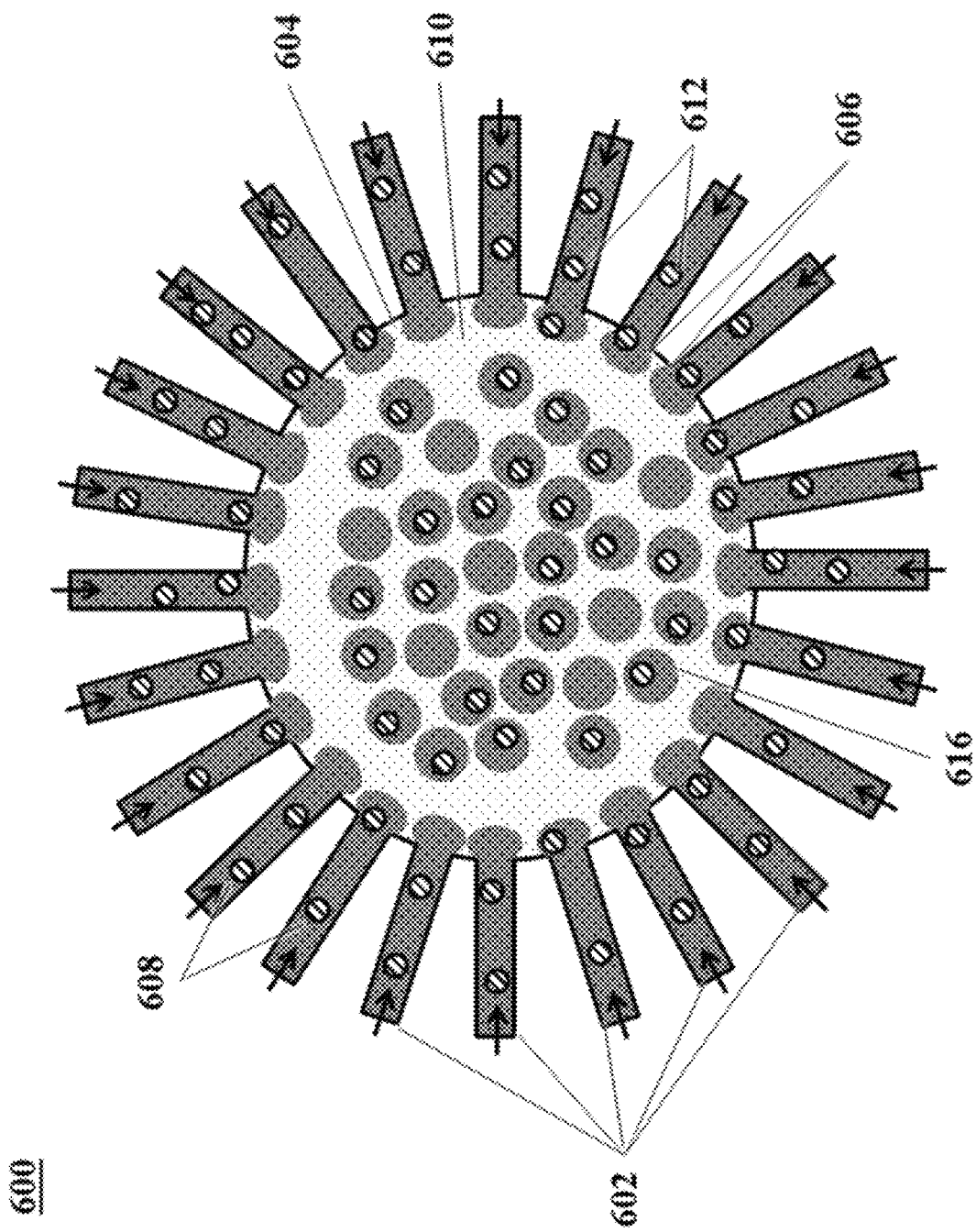
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, a (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
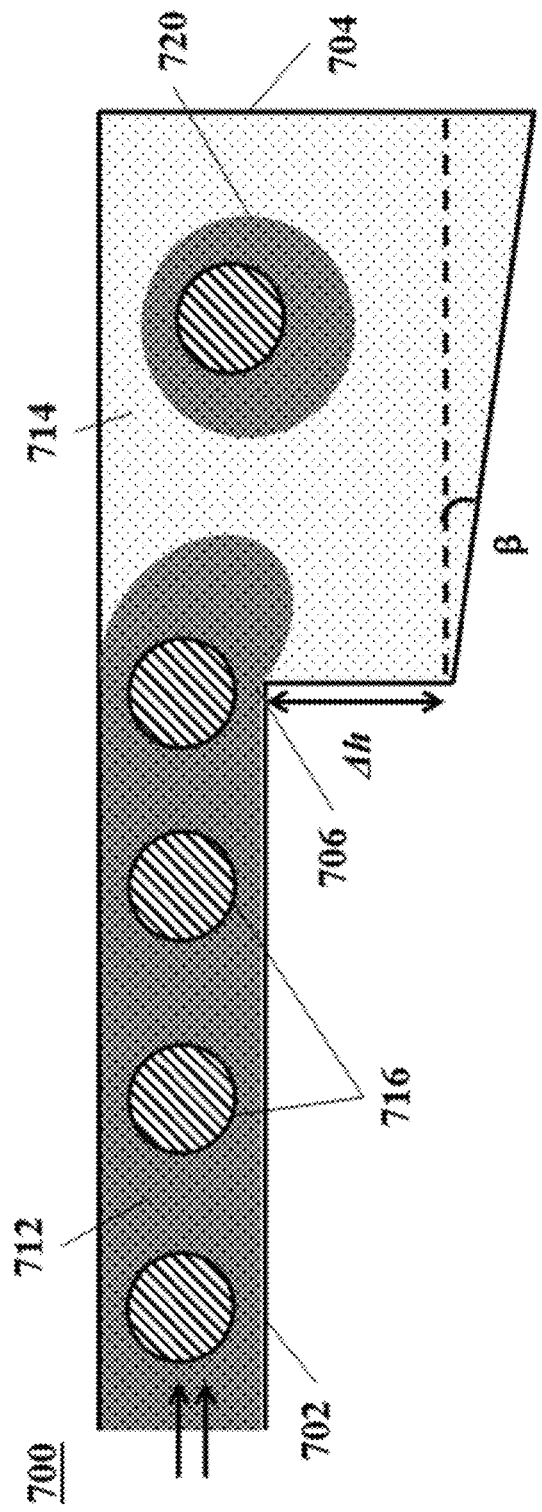
FIG. 7A shows a cross-section view of another example of a microfluidic channel structure with a geometric feature for controlled partitioning.
Figure 7B:
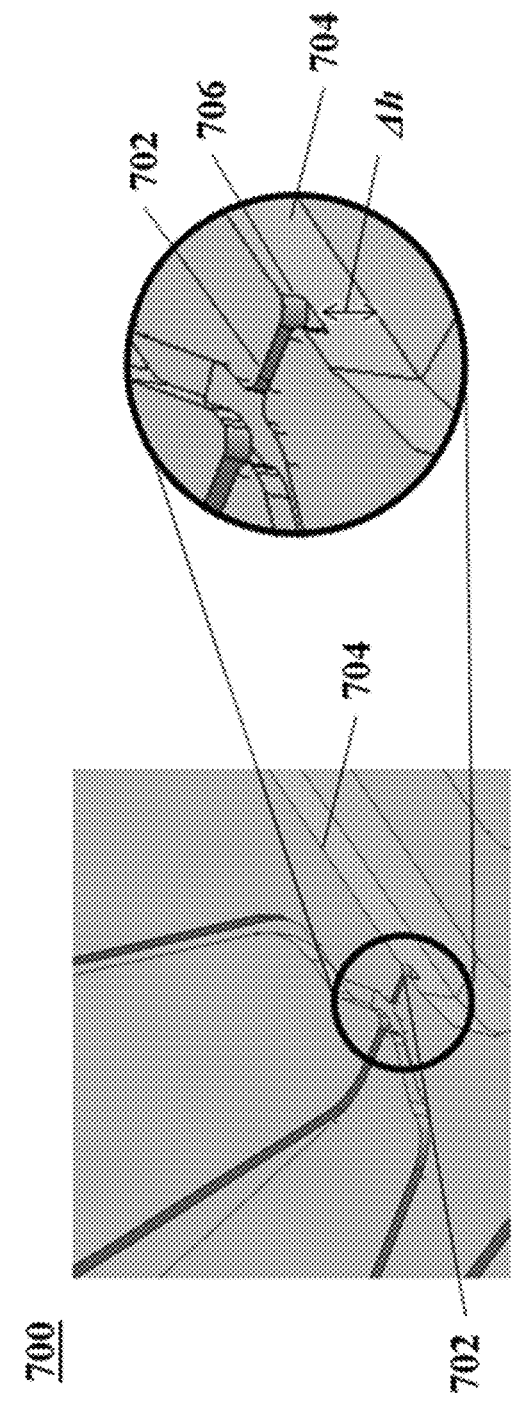
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., Δh, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of Δh. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, β, at or near the junction 706. The height difference, Δh, and/or expansion angle, β, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, β, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 712 entering the junction 706 can be between about 0.04 microliters (μL)/minute (min) and about 40 μL/min. In some instances, the flow rate of the aqueous fluid 712 entering the junction 706 can be between about 0.01 microliters (μL)/minute (min) and about 100 μL/min. Alternatively, the flow rate of the aqueous fluid 712 entering the junction 706 can be less than about 0.01 μL/min. Alternatively, the flow rate of the aqueous fluid 712 entering the junction 706 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, Δh, being abrupt at the junction 706 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Computer Systems

Figure 23:
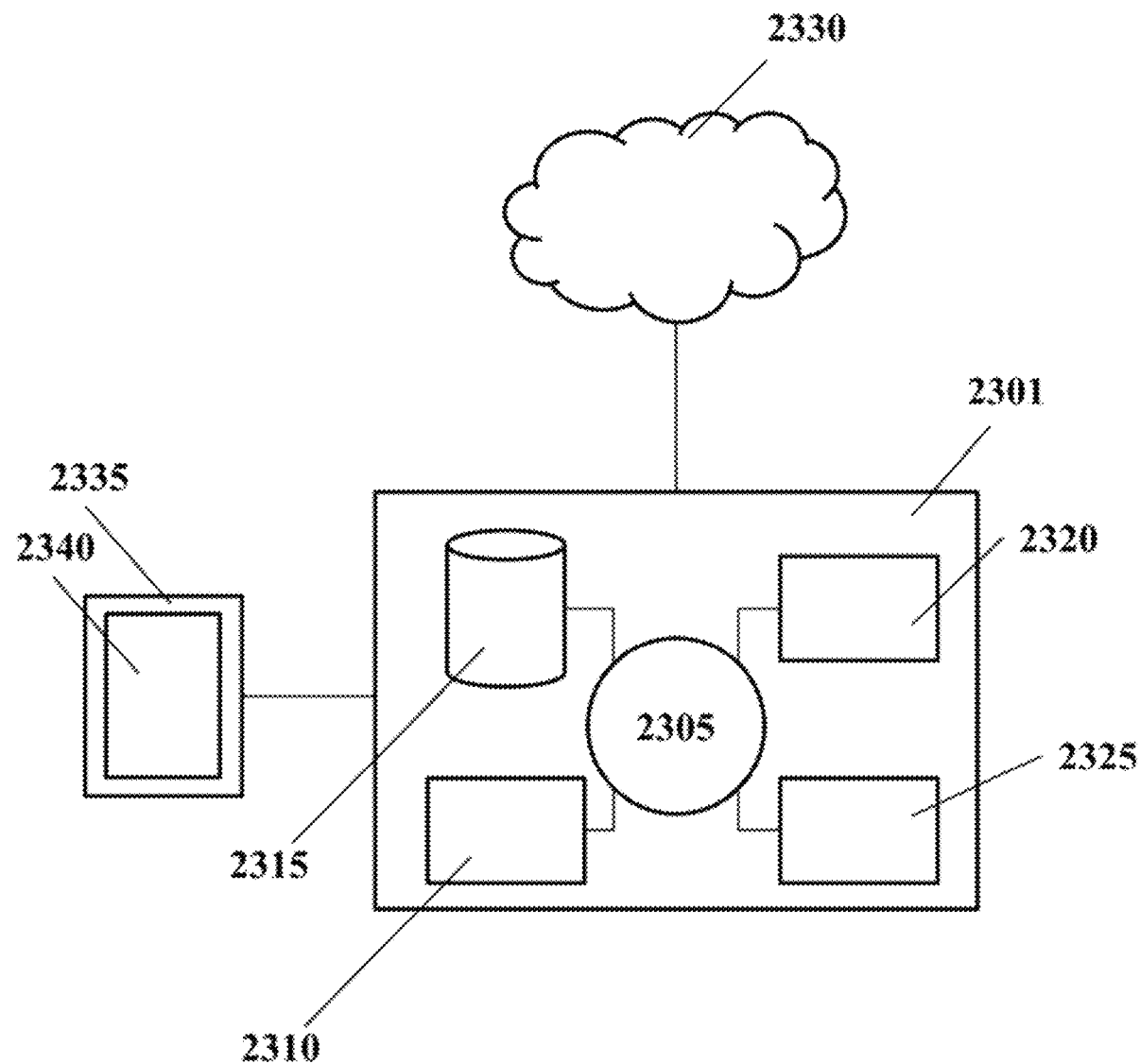
FIG. 23 shows a computer system that is programmed or otherwise configured to implement methods provided herein.

The present disclosure provides computer systems that are programmed to implement methods of the disclosure. FIG. 23 shows a computer system 2301 that is programmed or otherwise configured to, for example, (i) control a microfluidics system (e.g., fluid flow), (ii) sort occupied droplets from unoccupied droplets, (iii) polymerize droplets, (iv) perform sequencing applications, or (v) generate and maintain a library of nucleic acid molecules. The computer system 2301 can regulate various aspects of the present disclosure, such as, for example, fluid flow rates in one or more channels in a microfluidic structure, polymerization application units, etc. The computer system 2301 can be an electronic device of a user or a computer system that is remotely located with respect to the electronic device. The electronic device can be a mobile electronic device.

The computer system 2301 includes a central processing unit (CPU, also "processor" and "computer processor" herein) 2305, which can be a single core or multi core processor, or a plurality of processors for parallel processing. The computer system 2301 also includes memory or memory location 2310 (e.g., random-access memory, read-only memory, flash memory), electronic storage unit 2315 (e.g., hard disk), communication interface 2320 (e.g., network adapter) for communicating with one or more other systems, and peripheral devices 2325, such as cache, other memory, data storage and/or electronic display adapters. The memory 2310, storage unit 2315, interface 2320 and peripheral devices 2325 are in communication with the CPU 2305 through a communication bus (solid lines), such as a motherboard. The storage unit 2315 can be a data storage unit (or data repository) for storing data. The computer system 2301 can be operatively coupled to a computer network ("network") 2330 with the aid of the communication interface 2320. The network 2330 can be the Internet, an internet and/or extranet, or an intranet and/or extranet that is in communication with the Internet. The network 2330 in some cases is a telecommunication and/or data network. The network 2330 can include one or more computer servers, which can enable distributed computing, such as cloud computing. The network 2330, in some cases with the aid of the computer system 2301, can implement a peer-to-peer network, which may enable devices coupled to the computer system 2301 to behave as a client or a server.

The CPU 2305 can execute a sequence of machine-readable instructions, which can be embodied in a program or software. The instructions may be stored in a memory location, such as the memory 2310. The instructions can be directed to the CPU 2305, which can subsequently program or otherwise configure the CPU 2305 to implement methods of the present disclosure. Examples of operations performed by the CPU 2305 can include fetch, decode, execute, and writeback.

The CPU 2305 can be part of a circuit, such as an integrated circuit. One or more other components of the system 2301 can be included in the circuit. In some cases, the circuit is an application specific integrated circuit (ASIC).

The storage unit 2315 can store files, such as drivers, libraries and saved programs. The storage unit 2315 can store user data, e.g., user preferences and user programs. The computer system 2301 in some cases can include one or more additional data storage units that are external to the computer system 2301, such as located on a remote server that is in communication with the computer system 2301 through an intranet or the Internet.

The computer system 2301 can communicate with one or more remote computer systems through the network 2330. For instance, the computer system 2301 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2301 via the network 2330.

Methods as described herein can be implemented by way of machine (e.g., computer processor) executable code stored on an electronic storage location of the computer system 2301, such as, for example, on the memory 2310 or electronic storage unit 2315. The machine executable or machine readable code can be provided in the form of software. During use, the code can be executed by the processor 2305. In some cases, the code can be retrieved from the storage unit 2315 and stored on the memory 2310 for ready access by the processor 2305. In some situations, the electronic storage unit 2315 can be precluded, and machine-executable instructions are stored on memory 2310.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2301 can include or be in communication with an electronic display 2335 that comprises a user interface (UI) 2340 for providing, for example, results of sequencing analysis, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 2305. The algorithm can, for example, perform sequencing, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) form a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

Figure 24:
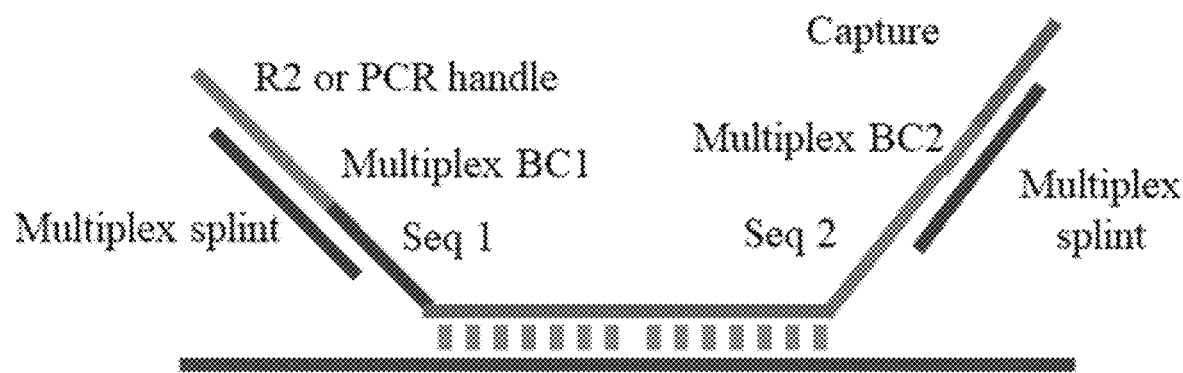
FIG. 24 illustrates an exemplary method for multiplexed barcoding.

Example 1: Alternate Method of Adding Multiplexing Information to 2-Part Probe Design Cells can be processed by barcoded probes as described generally in FIGS. 22A-C and the accompanying text. However, instead of including the barcode directly on the probes, the barcodes can be added post hybridization, but prior to pooling and partition-based barcoding (e.g., 2207). As shown in FIG. 24, Multiplexing can occur after a non-barcoded ligation probe pair is ligated and/or hybridized to the template. The free ends of the probe can be barcoded by attachment to barcode molecules by sticky end ligation, blunt end ligation, single stranded ligation, or extension. In some instances, a splint molecule is utilized to hybridize the barcodes to the probes for, e.g., ligation or extension. The multiplexed cell can now be partitioned and barcoded (e.g., hybridization of the capture sequence to a sequence on a nucleic acid barcode molecule (e.g., 2271)) as described elsewhere. This method allows the synthesis of a single set of diverse detection probes, and add the barcoding information using a less expensive reagent (barcoding oligonucleotides compatible with all probes in the pool).

Example 2: Multiplexing Using Padlock Probes

Figure 25:
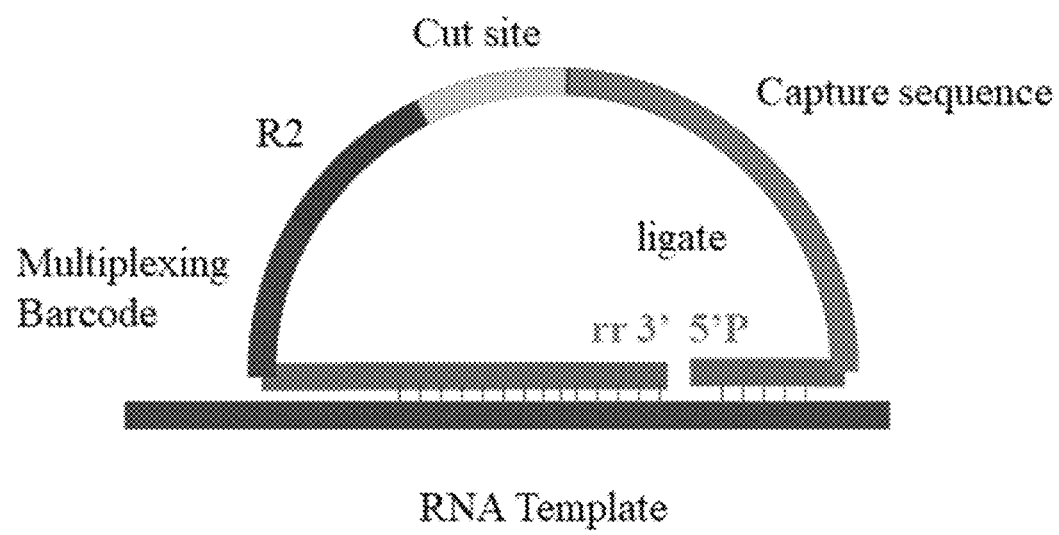
FIG. 25 illustrates an exemplary method for multiplexed barcoding.

Cells can be processed by barcoded probes as described generally in FIGS. 22A-C and the accompanying text. However, instead of utilizing a two-probe approach (e.g., 2201 and 2202), a padlock probe (such as those described in FIG. 13A-B) can be utilized. As shown in FIG. 25, a padlock probe is annealed to template (RNA or DNA) and properly annealed probes (can be a DNA or RNA ligase depending on probe design) are ligated. Optionally, a rolling circle amplification can be utilized to boost the signal (in which an optional UMI can be included in the padlock). The probe is then cut and the cut site (cut site could be a specific sequence, a cleavable moiety like an abasic site or uracil, a chemical linker that is cleavable, etc.). The cut molecule is then partitioned and barcoded (e.g., hybridization of the capture sequence to a sequence on a nucleic acid barcode molecule (e.g., 2271)) as described elsewhere. Alternately the cutting can be done concurrently with barcoding.

In another alternative example, the padlock probe does not comprise a barcode and is annealed to the template molecule and cut at the cut site. The free ends of the probe can be barcoded by attachment nucleic acid barcode molecules using sticky end ligation, blunt end ligation, single stranded ligation, or extension (as described in Example 1 and FIG. 24). In some instances, a splint molecule is utilized to hybridize the barcodes to the probes for, e.g., ligation or extension. The cell can now be partitioned and barcoded (e.g., hybridization of the capture sequence to a sequence on a nucleic acid barcode molecule (e.g., 2271)) as described elsewhere.

Example 3: Multiplexing in Context of Gap-Fill Reactions (Using Padlocks or Two-Probe Designs)

Figure 26:
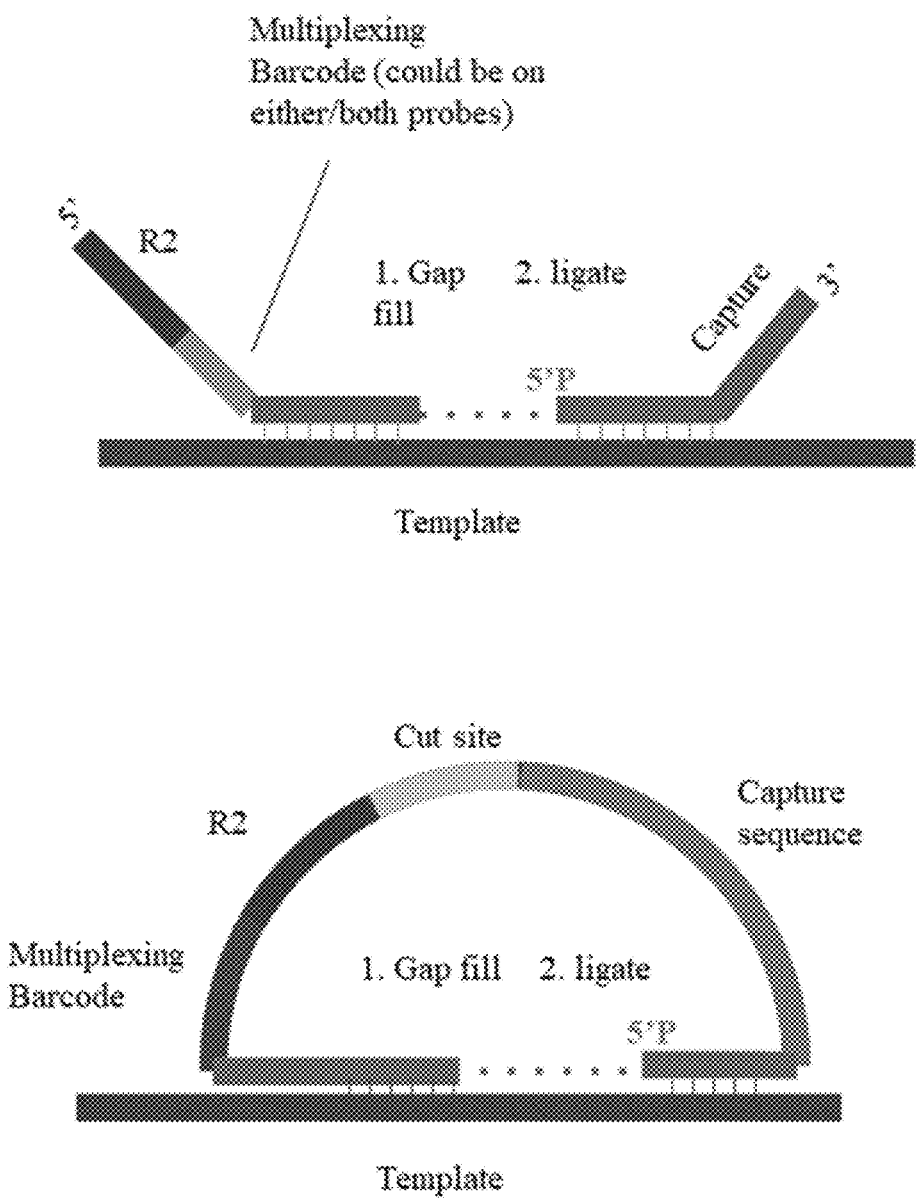
FIG. 26 illustrates an exemplary method for multiplexed barcoding.

Cells can be processed by barcoded probes as described generally in FIGS. 22A-C and the accompanying text. However, a gap-fill reaction can be utilized prior to probe ligation and processing. As shown in FIG. 26, the probes (e.g., padlock or two-probe approach described elsewhere herein) are annealed to a template (RNA or DNA) nucleic acid. A polymerase (DNA polymerase, reverse transcriptase or RNA polymerase) is untitled to fill in the space between the probes. Optionally, the 3' or 5' ends of the probe can be protected from exonuclease activity by a phosphorothioate modification. The gap-fill functionality allows the capture of sequence-specific information like splicing, fusions, or sequence variants. The multiplexed cell can now be partitioned and barcoded (e.g., hybridization of the capture sequence to a sequence on a nucleic acid barcode molecule (e.g., 2271)) as described elsewhere.

Example 4: Direct Ligation of Fragmented RNA or DNA to Barcoded Handles

Figure 27:
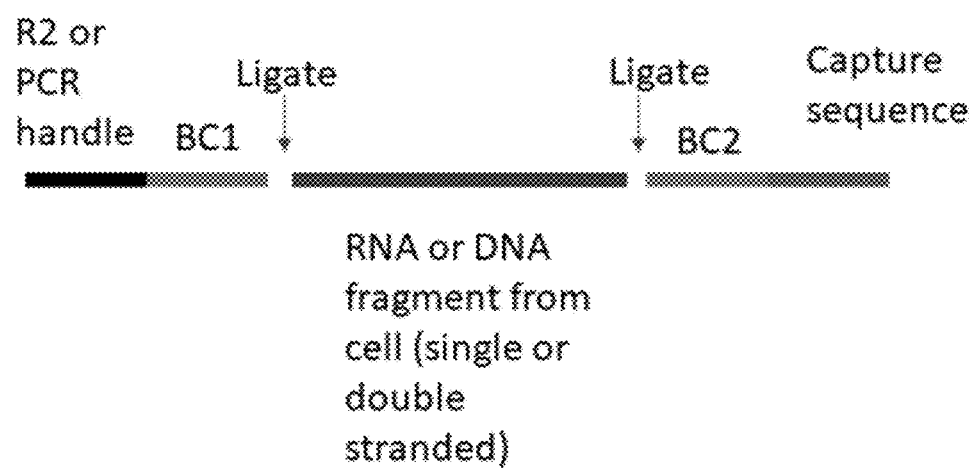
FIG. 27 illustrates an exemplary method for multiplexed barcoding.

Cells can be processed by barcoded probes as described generally in FIGS. 22A-C and the accompanying text. However, as shown in FIG. 27, RNA can be detected by directly ligating barcoded (BC1 and BC2) PCR handles/capture sequences to RNA fragments. This may be done in fresh cells, fixed cells, or cell beads. It may include a step of fragmenting the nucleic acids of interest. After flanking sequences are attached, downstream partitioning and barcoding in partitions is done, followed by amplification (PCR or RT-PCR) and sequencing to identify the captured sequence and the cell of origin.

EMBODIMENTS

In some cases, the present disclosure provides a method according to the following embodiments:
1. A method of analyzing a sample comprising a nucleic acid molecule, comprising:
   (a) providing:
      (i) a sample comprising said nucleic acid molecule, wherein said nucleic acid molecule comprises a first target region and a second target region, wherein said first target region and said second target region are disposed on a same strand of said nucleic acid molecule;
      (ii) a first probe comprising a first probe sequence and a second probe sequence, wherein said first probe sequence of said first probe is complementary to said first target region of said nucleic acid molecule; and
      (iii) a second probe comprising a third probe sequence, wherein said third probe sequence of said second probe is complementary to said second target region of said nucleic acid molecule;
   (b) subjecting said sample to conditions sufficient to (i) hybridize said first probe sequence of said first probe to said first target region of said nucleic acid molecule, and (ii) hybridize said third probe sequence of said second probe to said second target region of said nucleic acid molecule to yield a probe-associated nucleic acid molecule;
   (c) subjecting said probe-associated nucleic acid molecule to conditions sufficient to yield a probe-linked nucleic acid molecule comprising said first probe linked to said second probe; and
   (d) within a partition, attaching a barcode sequence to said first probe.
2. The method of embodiment 1, wherein said partition is a well among a plurality of wells.
3. The method of embodiment 1, wherein said partition is a droplet among a plurality of droplets.
4. The method of any one of embodiments 1-3, wherein (d) comprises (i) providing, in said partition, a nucleic acid barcode molecule comprising a binding sequence and a barcode sequence, wherein said binding sequence is complementary to said second probe sequence of said first probe, and (ii) subjecting said partition to conditions sufficient to hybridize said binding sequence to said second probe sequence.
5. The method of embodiment 4, further comprising subjecting said partition to conditions sufficient to extend said second probe sequence hybridized to said binding sequence of said nucleic acid barcode molecule to generate an extended first probe, wherein the extended first probe comprises a sequence complementary to said barcode sequence.
6. The method of embodiment 5, further comprising subjecting said extended first probe hybridized to said nucleic acid barcode molecule to conditions sufficient to separate said nucleic acid barcode molecule from said extended first probe.
7. The method of embodiment 5 or 6, further comprising subjecting said extended first probe hybridized to said nucleic acid barcode molecule to conditions sufficient to conduct an amplification reaction to generate an amplification product, which amplification product comprises said barcode sequence or a complement thereof
8. The method of embodiment 7, wherein said amplification reaction is a polymerase chain reaction.
9. The method of embodiment 7 or 8, wherein said amplification reaction is performed within said partition.
10. The method of embodiment 9, further comprising recovering said amplification product from said partition.
11. The method of embodiment 7 or 8, wherein said amplification reaction is performed outside of said partition.
12. The method of embodiment 10 or 11, further comprising sequencing said amplification product.
13. The method of any one of embodiments 1-3, further comprising (i) providing a splint oligonucleotide comprising a first sequence that is complementary to said second probe sequence and a second sequence, and (ii) subjecting said partition to conditions sufficient to hybridize said first sequence of said splint oligonucleotide to said second probe sequence of said first probe.
14. The method of embodiment 13, wherein said first sequence of said splint oligonucleotide hybridizes to said second probe sequence of said first probe prior to (c).
15. The method of embodiment 13, wherein said first sequence of said splint oligonucleotide hybridizes to said second probe sequence of said first probe after (c).
16. The method of embodiment 13, wherein said first sequence of said splint oligonucleotide hybridizes to said second probe sequence of said first probe prior to (d).
17. The method of any one of embodiments 13-16, wherein (d) comprises (i) providing, in said partition, a nucleic acid barcode molecule comprising a binding sequence and a barcode sequence, wherein said binding sequence is complementary to said second sequence of said splint oligonucleotide, and (ii) subjecting said partition to conditions sufficient to hybridize said binding sequence to said second sequence of said splint oligonucleotide.
18. The method of embodiment 17, wherein said binding sequence of said nucleic acid barcode molecule comprises ribobases.
19. The method of embodiment 17 or 18, further comprising subjecting said splint oligonucleotide hybridized to said first probe and said nucleic acid barcode molecule to conditions sufficient to ligate said second probe sequence hybridized to said splint oligonucleotide to said binding sequence of said nucleic acid barcode molecule.
20. The method of any one of embodiments 17-19, further comprising subjecting said splint oligonucleotide hybridized to said first probe and said nucleic acid barcode molecule to conditions sufficient to extend said second sequence of said splint oligonucleotide to an end of said nucleic acid barcode molecule to generate an extended splint oligonucleotide, wherein the extended splint oligonucleotide comprises a sequence complementary to said barcode sequence.
21. The method of embodiment 20, further comprising subjecting said extended splint oligonucleotide hybridized to said first probe and said nucleic acid barcode molecule to conditions sufficient to separate said extended splint oligonucleotide from said first probe and said nucleic acid barcode molecule.
22. The method of any one of embodiments 17-19, further comprising subjecting said splint oligonucleotide hybridized to said first probe and said nucleic acid barcode molecule to conditions sufficient to extend said first sequence of said splint oligonucleotide to generate an extended nucleic acid barcode product, wherein said extended nucleic acid barcode product comprises a sequence complementary to said first probe sequence of said first probe and a sequence complementary to said third probe sequence of said second probe.

23. The method of any one of embodiments 19-21, further comprising subjecting said first probe and said nucleic acid barcode molecule to conditions sufficient to conduct an amplification reaction to generate an amplification product, which amplification product comprises said barcode sequence or a complement thereof and said first probe sequence or a complement thereof 24. The method of embodiment 23, wherein said amplification reaction is a polymerase chain reaction.

25. The method of embodiment 23 or 24, wherein said amplification reaction is performed within said partition.

26. The method of embodiment 25, further comprising recovering said amplification product from said partition.

27. The method of embodiment 23 or 24, wherein said amplification reaction is performed outside of said partition.

28. The method of embodiment 26 or 27, further comprising sequencing said amplification product.

29. The method of any one of embodiments 4-28, wherein said nucleic acid barcode molecule further comprises a unique molecular identifier sequence.

30. The method of any one of embodiments 4-29, wherein said nucleic acid barcode molecule further comprises a sequencing primer.

31. The method of any one of embodiments 4-30, wherein, subsequent to (c), said probe-associated nucleic acid molecule is co-partitioned with said nucleic acid barcode molecule.

32. The method of any one of embodiments 4-30, wherein, subsequent to (a), said nucleic acid molecule is co-partitioned with said first probe, said second probe, and said nucleic acid barcode molecule.

33. The method of embodiment 32, wherein (c) is performed within said partition.

34. The method of embodiment 33, wherein (b) and (c) are performed within said partition.

35. The method of any one of embodiments 4-34, wherein said second probe comprises a fourth probe sequence, and wherein said method further comprises providing a nucleic acid binding molecule in said partition, wherein said nucleic acid binding molecule comprises a second binding sequence that is complementary to said fourth probe sequence of said second probe.

36. The method of embodiment 35, wherein said nucleic acid binding molecule further comprises a third binding sequence.

37. The method of embodiment 35 or 36, wherein said nucleic acid binding molecule further comprises a second barcode sequence.

38. The method of any one of embodiments 35-37, further comprising hybridizing said second binding sequence to said fourth probe sequence of said second probe within said partition.

39. The method of any one of embodiments 4-38, wherein said nucleic acid barcode molecule is coupled to a bead.

40. The method of embodiment 39, wherein said bead is a gel bead.

41. The method of embodiment 39 or 40, wherein said nucleic acid barcode molecule is coupled to said bead via a labile moiety.

42. The method of any one of embodiments 39-41, wherein said bead comprises a plurality of nucleic acid barcode molecules coupled thereto, wherein said plurality of nucleic acid barcode molecules comprise said nucleic acid barcode molecule.

43. The method of embodiment 42, wherein said bead comprises at least 10,000 nucleic acid barcode molecules coupled thereto.

44. The method of embodiment 43, wherein said bead comprises at least 100,000 nucleic acid barcode molecules coupled thereto.

45. The method of embodiment 44, wherein said bead comprises at least 1,000,000 nucleic acid barcode molecules coupled thereto.

46. The method of embodiment 45, wherein said bead comprises at least 10,000,000 nucleic acid barcode molecules coupled thereto.

47. The method of any one of embodiments 42-46, wherein said plurality of nucleic acid barcode molecules are releasably coupled to said bead.

48. The method of embodiment 47, wherein said plurality of nucleic acid barcode molecules are releasable from said bead upon application of a stimulus.

49. The method of embodiment 48, wherein said stimulus is selected from the group consisting of a thermal stimulus, a photo stimulus, and a chemical stimulus.

50. The method of embodiment 49, wherein said stimulus is a reducing agent.

51. The method of embodiment 50, wherein said stimulus is dithiothreitol.

52. The method of any one of embodiments 48-51, wherein the application of said stimulus results in one or more of (i) cleavage of a linkage between nucleic acid barcode molecules of said plurality of nucleic acid barcode molecules and said bead, and (ii) degradation of said bead to release nucleic acid barcode molecules of said plurality of nucleic acid barcode molecules from said bead.

53. The method of any one of embodiments 47-52, wherein said bead is provided in said partition, and wherein said nucleic acid barcode molecule is released from said bead within said partition.

54. The method of any one of embodiments 1-53, wherein (c) is performed before (d).

55. The method of any one of embodiments 1-53, wherein (d) is performed before (c).

56. The method of any one of embodiments 1-55, wherein said first probe further comprises a barcode sequence or unique molecular identifier.

57. The method of any one of embodiments 1-56, wherein said second probe further comprises a barcode sequence or a unique molecular identifier.

58. The method of any one of embodiments 1-57, wherein said second probe comprises a fourth probe sequence, which fourth probe sequence hybridizes to a third target region of said nucleic acid molecule.

59. The method of embodiment 58, wherein said second target region is not adjacent to said third target region, and wherein said third probe sequence and said fourth probe sequence of said second probe are separated by a linker sequence.

60. The method of any one of embodiments 1-59, wherein said first probe sequence of said first probe comprises a first reactive moiety and said third probe sequence of said second probe comprises a second reactive moiety, wherein, subsequent to (b), said first reactive moiety is adjacent to said second reactive moiety.

61. The method of embodiment 60, wherein (c) comprises subjecting said first reactive moiety and said second reactive moiety to conditions sufficient to link said first probe sequence to said third probe sequence.

62. The method of embodiment 60 or 61, wherein said first reactive moiety of said first probe comprises an azide moiety.
63. The method of any one of embodiments 60-62, wherein said second reactive moiety of said second probe comprises an alkyne moiety.
64. The method of any one of embodiments 60-63, wherein said first probe is linked to said second probe in said probe-linked nucleic acid molecule via a linker, wherein said linker comprises a triazole moiety.
65. The method of embodiment 60 or 61, wherein said first reactive moiety of said first probe comprises a phosphorothioate moiety.
66. The method of any one of embodiments 60, 61, or 65, wherein said second reactive moiety of said second probe comprises an iodide moiety.
67. The method of any one of embodiments 60, 61, 65, or 66, wherein said first probe is linked to said second probe in said probe-linked nucleic acid molecule via a linker, wherein said linker comprises a phosphorothioate bond.
68. The method of embodiment 60 or 61, wherein said first reactive moiety of said first probe comprises an amine moiety.
69. The method of any one of embodiments 60, 61, or 68, wherein said second reactive moiety of said second probe comprises a phosphate moiety.
70. The method of any one of embodiments 60, 61, 68, or 69, wherein said first probe is linked to said second probe in said probe-linked nucleic acid molecule via a linker, wherein said linker comprises a phosphoroamidatephosphoramidate bond.
71. The method of any one of embodiments 1-59, wherein (c) comprises performing a nucleic acid reaction.
72. The method of any one of embodiments 1-59 or 71, wherein (c) comprises performing an enzymatic ligation reaction or an extension reaction.
73. The method of embodiment 72, wherein (c) comprises performing both an enzymatic ligation reaction and an extension reaction.
74. The method of embodiment 72 or 73, wherein said enzymatic ligation reaction and/or said extension reaction comprises use of an enzyme selected from the group consisting of T4 RNL2, SplintR, T4 DNA ligase, KOD ligase, PBCV1, DNA polymerase, and Mu polymerase, or a derivative thereof
75. The method of any one of embodiments 1-74, wherein, prior to (a), said first probe is linked to said second probe via one or more linking sequences.
76. The method of embodiment 75, wherein said one or more linking sequences comprise a spacer sequence.
77. The method of embodiment 75 or 76, wherein said one or more linking sequences comprise a sequencing primer or complement thereof
78. The method of any one of embodiments 75-77, wherein said one or more linking sequences comprise a unique molecular identifier sequence.
79. The method of any one of embodiments 75-78, wherein said one or more linking sequences comprise a restriction site.
80. The method of any one of embodiments 75-79, wherein said one or more linking sequences comprise a capture sequence.
81. The method of any one of embodiments 75-80, wherein said one or more linking sequences comprise a thermolabile, photocleavable, or enzymatically cleavable site.
82. The method of any one of embodiments 75-81, wherein said one or more linking sequences comprise a transposition site.
83. The method of any one of embodiments 1-82, wherein said first target region is adjacent to said second target region.
84. The method of any one of embodiments 1-82, wherein said first target region and said second target region are separated by a gap region disposed between said first target region and said second target region.
85. The method of embodiment 84, wherein said gap region is at least one nucleotide long.
86. The method of embodiment 84 or 85, wherein said gap region is between 1-10 nucleotides long.
87. The method of embodiment 84 or 85, wherein said gap region is at least 10 nucleotides long.
88. The method of embodiment 87, wherein said gap region is at least 50 nucleotides long.
89. The method of embodiment 88, wherein said gap region is at least 100 nucleotides long.
90. The method of embodiment 89, wherein said gap region is at least 200 nucleotides long.
91. The method of embodiment 90, wherein said gap region is at least 500 nucleotides long.
92. The method of embodiment 87, wherein said gap region is between 50 and 200 nucleotides long.
93. The method of any one of embodiments 1-92, further comprising digesting one or more nucleic acid molecules or portions thereof using an exonuclease.
94. The method of any one of embodiments 1-93, wherein said first probe or said second probe comprises a known sequence.
95. The method of any one of embodiments 1-94, wherein said first probe or said second probe comprises a degenerate sequence.
96. The method of any one of embodiments 1-95, wherein said first probe or said second probe comprises a Phi-29 based rolling circle amplification sequence.
97. The method of any one of embodiments 1-96, wherein said first probe or said second probe comprises a cleavable site, wherein said cleavable site is cleavable using a thermal, photo-, chemical, or biological stimulus.
98. The method of any one of embodiments 1-97, wherein said first probe or said second probe comprises a transposition site.
99. The method of any one of embodiments 1-98, wherein said sample comprises a cell, and wherein said nucleic acid molecule is contained within said cell.
100. The method of embodiment 99, further comprising, subsequent to (a), permeabilizing said cell, thereby providing access to said nucleic acid molecule.
101. The method of embodiment 99, further comprising, subsequent to (a), lysing said cell, thereby releasing said nucleic acid molecule from said cell.
102. The method of any one of embodiments 99-101, wherein said cell is a prokaryotic cell.
103. The method of any one of embodiments 99-101, wherein said cell is a eukaryotic cell.
104. The method of any one of embodiments 99-101, wherein said cell is a lymphocyte.
105. The method of any one of embodiments 99-101, wherein said cell is a B cell.
106. The method of any one of embodiments 99-101, wherein said cell is a T cell.
107. The method of any one of embodiments 99-101, wherein said cell is a human cell.

108. The method of any one of embodiments 99-107, wherein said cell is a fixed suspension cell or a formalin-fixed paraffin-embedded cell.
109. The method of any one of embodiments 99-108, wherein said cell is provided within said partition.
110. The method of any one of embodiments 1-109, wherein said nucleic acid molecule is a single-stranded nucleic acid molecule.
111. The method of any one of embodiments 1-110, wherein said nucleic acid molecule is a ribonucleic acid (RNA) molecule.
112. The method of embodiment 111, wherein said nucleic acid molecule is a messenger RNA (mRNA) molecule.
113. The method of embodiment 111 or 112, wherein said nucleic acid molecule comprises a polyA sequence at a terminus of said nucleic acid molecule.
114. The method of embodiment 111, wherein said RNA molecule does not comprise a polyA sequence.
115. The method of any one of embodiments 111-114, wherein said nucleic acid molecule comprises an untranslated region (UTR).
116. The method of any one of embodiments 111-115, wherein said nucleic acid molecule comprises a 5' cap structure.
117. The method of any one of embodiments 1-110, wherein said nucleic acid molecule is a deoxyribonucleic acid (DNA) molecule.
118. The method of any one of embodiments 1-117, wherein said partition further comprises one or more reagents selected from the group consisting of fluorophores, oligonucleotides, primers, nucleic acid barcode molecules, barcodes, buffers, deoxynucleotide triphosphates, DNA splints, detergents, reducing agents, chelating agents, oxidizing agents, nanoparticles, antibodies, and enzymes.
119. The method of any one of embodiments 1-118, wherein said partition further comprises one or more reagents selected from the group consisting of temperature-sensitive enzymes, pH-sensitive enzymes, light-sensitive enzymes, proteases, ligase, polymerases, reverse transcriptases, restriction enzymes, nucleases, protease inhibitors, and nuclease inhibitors.
120. The method of embodiment 119, wherein said polymerase is a polymerase selected from the group of DNA polymerase, RNA polymerase, Hot Start polymerase, and Warm start polymerase.
121. The method of any one of embodiments 1-120, wherein said sample comprises a cell bead, and wherein said nucleic acid molecule is contained within said cell bead.
122. The method of any one of embodiments 1-121, wherein (a)-(c) are performed without reverse transcription.
123. A method of analyzing a sample comprising a nucleic acid molecule, comprising:
   (a) providing:
      (i) a sample comprising said nucleic acid molecule, wherein said nucleic acid molecule comprises a target region;
      (ii) a probe comprising a probe sequence and a binding sequence, wherein said probe sequence is complementary to said target region; and
      (iii) an adapter comprising a first sequence and a second sequence, wherein said first sequence of said adapter is complementary to said binding sequence of said probe;
   (b) subjecting said sample to conditions sufficient to hybridize (i) said probe sequence of said probe to said target region, and (ii) said binding sequence of said probe to said first sequence of said adapter, to yield an adapter-bound probe; and
   (c) within a partition, barcoding said adapter-bound probe to provide a barcoded nucleic acid molecule.
124. The method of embodiment 123, wherein said partition is a well among a plurality of wells.
125. The method of embodiment 123, wherein said partition is a droplet among a plurality of droplets.
126. The method of any one of embodiments 123-125, wherein said first sequence of said adapter hybridizes to said binding sequence of said probe within said partition.
127. The method of any one of embodiments 123-125, wherein said first sequence of said adapter hybridizes to said binding sequence of said probe outside of said partition.
128. The method of any one of embodiments 123-127, wherein (c) comprises (i) providing, in said partition, a nucleic acid barcode molecule comprising an overhang sequence and a barcode sequence, wherein said overhang sequence is complementary to said second sequence of said adapter, and (ii) subjecting said partition to conditions sufficient to hybridize said overhang sequence to said second sequence of said adapter to yield said barcoded nucleic acid molecule.
129. The method of embodiment 128, wherein said overhang sequence of said nucleic acid barcode molecule comprises ribobases.
130. The method of embodiment 128 or 129, further comprising subjecting said barcoded nucleic acid molecule to conditions sufficient to ligate said binding sequence hybridized to said adapter to said overhang sequence of said nucleic acid barcode molecule.
131. The method of embodiment 130, wherein said ligating occurs outside of said partition.
132. The method of any one of embodiments 128-131, further comprising subjecting said barcoded nucleic acid molecule to conditions sufficient to extend said second sequence of said adapter to an end of said nucleic acid barcode molecule to generate an extended adapter, wherein the extended adapter comprises a sequence complementary to said barcode sequence.
133. The method of embodiment 132, further comprising subjecting said extended adapter hybridized to said probe and said nucleic acid barcode molecule to conditions sufficient to separate said extended adapter from said probe and said nucleic acid barcode molecule.
134. The method of any one of embodiments 128-134, wherein said nucleic acid barcode molecule further comprises a unique molecular identifier sequence.
135. The method of any one of embodiments 128-135, wherein said nucleic acid barcode molecule further comprises a sequencing primer.
136. The method of any one of embodiments 128-135, wherein said nucleic acid barcode molecule is coupled to a bead.
137. The method of embodiment 136, wherein said bead is a gel bead.
138. The method of embodiment 136 or 137, wherein said nucleic acid barcode molecule is coupled to said bead via a labile moiety.
139. The method of any one of embodiments 136-138, wherein said bead comprises a plurality of nucleic acid barcode molecules coupled thereto, wherein said plurality of nucleic acid barcode molecules comprise said nucleic acid barcode molecule.

140. The method of embodiment 139, wherein said bead comprises at least 10,000 nucleic acid barcode molecules coupled thereto.

141. The method of embodiment 140, wherein said bead comprises at least 100,000 nucleic acid barcode molecules coupled thereto.

142. The method of embodiment 141, wherein said bead comprises at least 1,000,000 nucleic acid barcode molecules coupled thereto.

143. The method of embodiment 142, wherein said bead comprises at least 10,000,000 nucleic acid barcode molecules coupled thereto.

144. The method of any one of embodiments 136-143, wherein said plurality of nucleic acid barcode molecules are releasably coupled to said bead.

145. The method of embodiment 144, wherein said plurality of nucleic acid barcode molecules are releasable from said bead upon application of a stimulus.

146. The method of embodiment 145, wherein said stimulus is selected from the group consisting of a thermal stimulus, a photo stimulus, and a chemical stimulus.

147. The method of embodiment 146, wherein said stimulus is a reducing agent.

148. The method of embodiment 147, wherein said stimulus is dithiothreitol.

149. The method of any one of embodiments 145-148, wherein the application of said stimulus results in one or more of (i) cleavage of a linkage between nucleic acid barcode molecules of said plurality of nucleic acid barcode molecules and said bead, and (ii) degradation of said bead to release nucleic acid barcode molecules of said plurality of nucleic acid barcode molecules from said bead.

150. The method of any one of embodiments 144-149, wherein said bead is provided in said partition, and wherein said nucleic acid barcode molecule is released from said bead within said partition.

151. The method of any one of embodiments 123-150, further comprising recovering said barcoded nucleic acid molecule from said partition.

152. The method of embodiment 151, wherein said partition is a droplet, and wherein recovering said barcoded nucleic acid molecule from said partition comprises breaking or bursting said droplet.

153. The method of any one of embodiments 123-153, further comprising digesting one or more nucleic acid molecules using an exonuclease.

154. The method of embodiment 153, wherein said digesting is performed after (c) in a bulk solution.

155. The method of embodiment 154, wherein said one or more nucleic acid molecules are probe and adapter molecules that are not coupled to said nucleic acid molecule.

156. The method of any one of embodiments 123-155, further comprising providing an additional probe comprising an additional probe sequence, which additional probe sequence is complementary to an additional target region of said nucleic acid molecule.

157. The method of embodiment 156, wherein said additional target region is adjacent to said target region of said nucleic acid molecule.

158. The method of embodiment 156, wherein said target region and said additional target region are disposed on a same strand of said nucleic acid molecule but are separated by a gap region.

159. The method of embodiment 158, wherein said gap region is at least one nucleotide long.

160. The method of embodiment 158 or 159, wherein said gap region is between 1-10 nucleotides long.

161. The method of embodiment 158 or 159, wherein said gap region is at least 10 nucleotides long.

162. The method of embodiment 161, wherein said gap region is at least 50 nucleotides long.

163. The method of embodiment 162, wherein said gap region is at least 100 nucleotides long.

164. The method of embodiment 163, wherein said gap region is at least 200 nucleotides long.

165. The method of embodiment 164, wherein said gap region is at least 500 nucleotides long.

166. The method of embodiment 162, wherein said gap region is between 50 and 200 nucleotides long.

167. The method of any one of embodiments 156-166, wherein said additional probe further comprises a sequencing primer.

168. The method of any one of embodiments 156-167, further comprising (d) subjecting said barcoded nucleic acid molecule hybridized to said target region of said nucleic acid molecule to conditions sufficient to hybridize said additional probe sequence of said additional probe to said additional target region.

169. The method of embodiment 168, wherein said probe sequence of said probe comprises a first reactive moiety and said additional probe sequence of said additional probe comprises a second reactive moiety, wherein, subsequent to (d), said first reactive moiety is adjacent to said second reactive moiety.

170. The method of embodiment 169, further comprising subjecting said first reactive moiety and said second reactive moiety to conditions sufficient to link said probe sequence to said additional probe sequence.

171. The method of embodiment 169 or 170, wherein said first reactive moiety of said first probe comprises an azide moiety.

172. The method of any one of embodiments 169-171, wherein said second reactive moiety of said second probe comprises an alkyne moiety.

173. The method of any one of embodiments 169-172, wherein said first probe is linked to said second probe in said probe-linked nucleic acid molecule via a linker, wherein said linker comprises a triazole moiety.

174. The method of embodiment 169 or 170, wherein said first reactive moiety of said first probe comprises a phosphorothioate moiety.

175. The method of any one of embodiments 169, 170, or 174, wherein said second reactive moiety of said second probe comprises an iodide moiety.

176. The method of any one of embodiments 169, 170, 174, or 175, wherein said first probe is linked to said second probe in said probe-linked nucleic acid molecule via a linker, wherein said linker comprises a phosphorothioate bond.

177. The method of embodiment 169 or 170, wherein said first reactive moiety of said first probe comprises an amine moiety.

178. The method of any one of embodiments 169, 170, or 177, wherein said second reactive moiety of said second probe comprises a phosphate moiety.

179. The method of any one of embodiments 169, 170, 177, or 178, wherein said first probe is linked to said second probe in said probe-linked nucleic acid molecule via a linker, wherein said linker comprises a phosphoroamidatephosphoramidate bond.

180. The method of embodiment 168, wherein said probe hybridized to said target region is linked to said additional probe hybridized to said additional target region via a nucleic acid reaction.
181. The method of embodiment 168, wherein said probe hybridized to said target region is linked to said additional probe hybridized to said additional target region via an enzymatic ligation reaction or an extension reaction.
182. The method of embodiment 181, wherein said probe hybridized to said target region is linked to said additional probe hybridized to said additional target region via both an enzymatic ligation reaction and an extension reaction.
183. The method of embodiment 181 or 182, wherein said enzymatic ligation reaction and/or said extension reaction comprises use of an enzyme selected from the group consisting of T4 RNL2, SplintR, T4 DNA ligase, KOD ligase, PBCV1, DNA polymerase, and Mu polymerase, or a derivative thereof
184. The method of any one of embodiments 156-183, wherein said additional probe is provided within said partition.
185. The method of any one of embodiments 156-183, wherein said additional probe is provided within another partition.
186. The method of any one of embodiments 168-185, further comprising subjecting said barcoded nucleic acid molecule hybridized to said nucleic acid molecule to conditions sufficient to conduct an amplification reaction to generate an amplification product, which amplification product comprises said barcode sequence or a complement thereof and said probe sequence or a complement thereof
187. The method of embodiment 186, wherein said amplification reaction is a polymerase chain reaction.
188. The method of embodiment 186 or 187, wherein said amplification reaction is performed within said partition.
189. The method of embodiment 188, further comprising recovering said amplification product from said partition.
190. The method of embodiment 186 or 187, wherein said amplification reaction is performed outside of said partition.
191. The method of embodiment 189 or 190, further comprising sequencing said amplification product.
192. The method of any one of embodiments 123-191, wherein said probe further comprises a barcode sequence or unique molecular identifier.
193. The method of any one of embodiments 156-192, wherein said probe or said additional probe comprises a known sequence.
194. The method of any one of embodiments 156-193, wherein said probe or said additional probe comprises a degenerate sequence.
195. The method of any one of embodiments 156-194, wherein said probe or said additional probe comprises a cleavable site, wherein said cleavable site is cleavable using a thermal, photo-, chemical, or biological stimulus.
196. The method of any one of embodiments 156-195, wherein said first probe or said second probe comprises a transposition site.
197. The method of any one of embodiments 123-196, wherein said sample comprises a cell, and wherein said nucleic acid molecule is contained within said cell.
198. The method of embodiment 197, further comprising, subsequent to (a), permeabilizing said cell, thereby providing access to said nucleic acid molecule.
199. The method of embodiment 197, further comprising, subsequent to (a), lysing said cell, thereby releasing said nucleic acid molecule from said cell.
200. The method of any one of embodiments 197-199, wherein said cell is a prokaryotic cell.
201. The method of any one of embodiments 197-199, wherein said cell is a eukaryotic cell.
202. The method of any one of embodiments 197-199, wherein said cell is a lymphocyte.
203. The method of any one of embodiments 197-199, wherein said cell is a B cell.
204. The method of any one of embodiments 197-199, wherein said cell is a T cell.
205. The method of any one of embodiments 197-199, wherein said cell is a human cell.
206. The method of any one of embodiments 197-205, wherein said cell is a fixed suspension cell or a formalin-fixed paraffin-embedded cell.
207. The method of any one of embodiments 197-206, wherein said cell is provided within said partition.
208. The method of any one of embodiments 123-207, wherein said nucleic acid molecule is a single-stranded nucleic acid molecule.
209. The method of any one of embodiments 123-208, wherein said nucleic acid molecule is a ribonucleic acid (RNA) molecule.
210. The method of embodiment 209, wherein said nucleic acid molecule is a messenger RNA (mRNA) molecule.
211. The method of embodiment 209 or 210, wherein said nucleic acid molecule comprises a polyA sequence at a terminus of said nucleic acid molecule.
212. The method of embodiment 209, wherein said RNA molecule does not comprise a polyA sequence.
213. The method of any one of embodiments 209-212, wherein said nucleic acid molecule comprises an untranslated region (UTR).
214. The method of any one of embodiments 209-213, wherein said nucleic acid molecule comprises a 5' cap structure.
215. The method of any one of embodiments 123-208, wherein said nucleic acid molecule is a deoxyribonucleic acid (DNA) molecule.
216. The method of any one of embodiments 123-215, wherein said partition further comprises one or more reagents selected from the group consisting of fluorophores, oligonucleotides, primers, nucleic acid barcode molecules, barcodes, buffers, deoxynucleotide triphosphates, DNA splints, detergents, reducing agents, chelating agents, oxidizing agents, nanoparticles, antibodies, and enzymes.
217. The method of any one of embodiments 123-216, wherein said partition further comprises one or more reagents selected from the group consisting of temperature-sensitive enzymes, pH-sensitive enzymes, light-sensitive enzymes, proteases, ligase, polymerases, reverse transcriptases, restriction enzymes, nucleases, protease inhibitors, and nuclease inhibitors.
218. The method of embodiment 217, wherein said polymerase is a polymerase selected from the group of DNA polymerase, RNA polymerase, Hot Start polymerase, and Warm start polymerase
219. The method of any one of embodiments 123-218, wherein said sample comprises a cell bead, and wherein said nucleic acid molecule is contained within said cell bead.

220. The method of any one of embodiments 123-219, wherein (a)-(c) are performed without reverse transcription.
221. A method of analyzing a sample comprising a nucleic acid molecule, comprising:
   (a) providing:
      (i) a sample comprising said nucleic acid molecule, wherein said nucleic acid molecule comprises a target region;
      (ii) a probe comprising a probe sequence and a first reactive moiety, wherein said probe sequence is complementary to said target region; and
      (iii) a nucleic acid barcode molecule comprising a second reactive moiety and a barcode sequence;
   (b) subjecting said sample to conditions sufficient to hybridize said probe sequence of said probe to said target region to provide a probe-associated nucleic acid molecule; and
   (c) within a partition, subjecting said first reactive moiety of said probe-associated nucleic acid molecule and said second reactive moiety of said nucleic acid barcode molecule to conditions sufficient to link said probe-associated nucleic acid molecule and said nucleic acid barcode molecule to provide a barcoded nucleic acid product.
222. The method of embodiment 221, wherein said partition is a well among a plurality of wells.
223. The method of embodiment 221, wherein said partition is a droplet among a plurality of droplets.
224. The method of any one of embodiments 221-223, wherein said probe further comprises a sequencing primer.
225. The method of any one of embodiments 221-224, wherein said probe further comprises a spacer sequence disposed between said probe sequence and said first reactive moiety.
226. The method of any one of embodiments 221-225, wherein (b) is performed within said partition.
227. The method of any one of embodiments 221-225, wherein (b) is performed outside of said partition.
228. The method of any one of embodiments 221-227, wherein said nucleic acid barcode molecule comprises a unique molecular identifier sequence.
229. The method of any one of embodiments 221-228, wherein said nucleic acid barcode molecule comprises a sequencing primer.
230. The method of any one of embodiments 221-229, wherein said nucleic acid barcode molecule comprises a spacer sequence disposed between said second reactive moiety and another sequence of said nucleic acid barcode molecule.
231. The method of any one of embodiments 221-230, wherein said nucleic acid barcode molecule is coupled to a bead.
232. The method of embodiment 231, wherein said bead is a gel bead.
233. The method of embodiment 231 or 232, wherein said nucleic acid barcode molecule is coupled to said bead via a labile moiety.
234. The method of any one of embodiments 231-233, wherein said bead comprises a plurality of nucleic acid barcode molecules coupled thereto, wherein said plurality of nucleic acid barcode molecules comprise said nucleic acid barcode molecule.
235. The method of embodiment 234, wherein said bead comprises at least 10,000 nucleic acid barcode molecules coupled thereto.
236. The method of embodiment 235, wherein said bead comprises at least 100,000 nucleic acid barcode molecules coupled thereto.
237. The method of embodiment 236, wherein said bead comprises at least 1,000,000 nucleic acid barcode molecules coupled thereto.
238. The method of embodiment 237, wherein said bead comprises at least 10,000,000 nucleic acid barcode molecules coupled thereto.
239. The method of any one of embodiments 234-238, wherein said plurality of nucleic acid barcode molecules are releasably coupled to said bead.
240. The method of embodiment 239, wherein said plurality of nucleic acid barcode molecules are releasable from said bead upon application of a stimulus.
241. The method of embodiment 240, wherein said stimulus is selected from the group consisting of a thermal stimulus, a photo stimulus, and a chemical stimulus.
242. The method of embodiment 241, wherein said stimulus is a reducing agent.
243. The method of embodiment 242, wherein said stimulus is dithiothreitol.
244. The method of any one of embodiments 240-243, wherein the application of said stimulus results in one or more of (i) cleavage of a linkage between nucleic acid barcode molecules of said plurality of nucleic acid barcode molecules and said bead, and (ii) degradation of said bead to release nucleic acid barcode molecules of said plurality of nucleic acid barcode molecules from said bead.
245. The method of any one of embodiments 231-245, wherein said bead is provided in said partition, and wherein said nucleic acid barcode molecule is released from said bead within said partition.
246. The method of any one of embodiments 221-245, further comprising recovering said barcoded nucleic acid molecule from said partition.
247. The method of embodiment 246, wherein said partition is a droplet, and wherein recovering said barcoded nucleic acid molecule from said partition comprises breaking or bursting said droplet.
248. The method of any one of embodiments 221-247, wherein said first reactive moiety of said first probe comprises an azide moiety.
249. The method of any one of embodiments 221-248, wherein said second reactive moiety of said second probe comprises an alkyne moiety.
250. The method of any one of embodiments 221-249, wherein said first probe is linked to said second probe in said probe-linked nucleic acid molecule via a linker, wherein said linker comprises a triazole moiety.
251. The method of any one of embodiments 221-247, wherein said first reactive moiety of said first probe comprises a phosphorothioate moiety.
252. The method of any one of embodiments 221-247 or 251, wherein said second reactive moiety of said second probe comprises an iodide moiety.
253. The method of any one of embodiments 221-247, 251, or 252, wherein said first probe is linked to said second probe in said probe-linked nucleic acid molecule via a linker, wherein said linker comprises a phosphorothioate bond.
254. The method of any one of embodiments 221-247, wherein said first reactive moiety of said first probe comprises an amine moiety.

255. The method of any one of embodiments 221-247 or 254, wherein said second reactive moiety of said second probe comprises a phosphate moiety.
256. The method of any one of embodiments 221-247, 254, or 255, wherein said first probe is linked to said second probe in said probe-linked nucleic acid molecule via a linker, wherein said linker comprises a phosphoroamidatephosphoramidate bond.
257. The method of any one of embodiments 221-256 further comprising subjecting said barcoded nucleic acid product hybridized to said nucleic acid molecule to conditions sufficient to conduct an amplification reaction to generate an amplification product, which amplification product comprises said barcode sequence or a complement thereof and said probe sequence or a complement thereof
258. The method of embodiment 257, wherein said amplification reaction is a polymerase chain reaction.
259. The method of embodiment 257 or 258, wherein said amplification reaction is performed within said partition.
260. The method of embodiment 259, further comprising recovering said amplification product from said partition.
261. The method of embodiment 257 or 258, wherein said amplification reaction is performed outside of said partition.
262. The method of embodiment 260 or 261, further comprising sequencing said amplification product.
263. The method of any one of embodiments 221-262, wherein said probe further comprises a barcode sequence or unique molecular identifier.
264. The method of any one of embodiments 221-263, wherein said probe comprises a known sequence.
265. The method of any one of embodiments 221-264, wherein said probe comprises a degenerate sequence.
266. The method of any one of embodiments 221-265, wherein said probe comprises a cleavable site, wherein said cleavable site is cleavable using a thermal, photo-, chemical, or biological stimulus.
267. The method of any one of embodiments 221-266, wherein said probe comprises a transposition site.
268. The method of any one of embodiments 221-267, wherein said sample comprises a cell, and wherein said nucleic acid molecule is contained within said cell.
269. The method of embodiment 268, further comprising, subsequent to (a), permeabilizing said cell, thereby providing access to said nucleic acid molecule.
270. The method of embodiment 268, further comprising, subsequent to (a), lysing said cell, thereby releasing said nucleic acid molecule from said cell.
271. The method of any one of embodiments 268-270, wherein said cell is a prokaryotic cell.
272. The method of any one of embodiments 268-270, wherein said cell is a eukaryotic cell.
273. The method of any one of embodiments 268-270, wherein said cell is a lymphocyte.
274. The method of any one of embodiments 268-270, wherein said cell is a B cell.
275. The method of any one of embodiments 268-270, wherein said cell is a T cell.
276. The method of any one of embodiments 268-270, wherein said cell is a human cell.
277. The method of any one of embodiments 268-276, wherein said cell is a fixed suspension cell or a formalin-fixed paraffin-embedded cell.
278. The method of any one of embodiments 268-277, wherein said cell is provided within said partition.
279. The method of any one of embodiments 221-278, wherein said nucleic acid molecule is a single-stranded nucleic acid molecule.
280. The method of any one of embodiments 221-279, wherein said nucleic acid molecule is a ribonucleic acid (RNA) molecule.
281. The method of embodiment 280, wherein said nucleic acid molecule is a messenger RNA (mRNA) molecule.
282. The method of embodiment 280 or 281, wherein said nucleic acid molecule comprises a polyA sequence at a terminus of said nucleic acid molecule.
283. The method of embodiment 280 or 281, wherein said RNA molecule does not comprise a polyA sequence.
284. The method of any one of embodiments 280-283, wherein said nucleic acid molecule comprises an untranslated region (UTR).
285. The method of any one of embodiments 280-284, wherein said nucleic acid molecule comprises a 5' cap structure.
286. The method of any one of embodiments 221-279, wherein said nucleic acid molecule is a deoxyribonucleic acid (DNA) molecule.
287. The method of any one of embodiments 221-286, wherein said partition further comprises one or more reagents selected from the group consisting of fluorophores, oligonucleotides, primers, nucleic acid barcode molecules, barcodes, buffers, deoxynucleotide triphosphates, DNA splints, detergents, reducing agents, chelating agents, oxidizing agents, nanoparticles, antibodies, and enzymes.
288. The method of any one of embodiments 221-287, wherein said partition further comprises one or more reagents selected from the group consisting of temperature-sensitive enzymes, pH-sensitive enzymes, light-sensitive enzymes, proteases, ligase, polymerases, reverse transcriptases, restriction enzymes, nucleases, protease inhibitors, and nuclease inhibitors.
289. The method of embodiment 288, wherein said polymerase is a polymerase selected from the group of DNA polymerase, RNA polymerase, Hot Start polymerase, and Warm start polymerase
290. The method of any one of embodiments 221-289, wherein said sample comprises a cell bead, and wherein said nucleic acid molecule is contained within said cell bead.
291. The method of any one of embodiments 221-290, wherein (a)-(c) are performed without reverse transcription.
292. The method of any one of embodiments 1-33, wherein (a)-(d) are repeated for a plurality of nucleic acid molecules, a plurality of first probes, a plurality of second probes, a plurality of barcode sequences, and a plurality of partitions, wherein in (d), a plurality of probe-associated nucleic acid molecule are partitioned among a plurality of partitions, where each partition of said plurality of partitions comprises a different barcode sequence of said plurality of barcode sequences.
293. The method of embodiments 292, wherein (c) comprises generating a plurality of probe-associated nucleic acid molecules, and wherein (c) is performed in an additional plurality of partitions, which additional plurality of partitions are different than said plurality of partitions.
294. The method of embodiment 293, wherein said plurality of partitions is a plurality of droplets and wherein said plurality of additional partitions is a plurality of wells.

295. The method of embodiment 293 or 294, wherein said plurality of first probes or said plurality of second probes comprises a plurality of partition barcode sequences.
296. The method of embodiment 295, wherein each probe-associated nucleic acid molecule of said plurality of probe-associated nucleic acid molecules generated in said additional plurality of partitions in (c) comprises a partition barcode sequence of said plurality of partition barcode sequences.
297. The method of embodiment 296, wherein each additional partition of said additional plurality of partitions comprises a different partition barcode sequence of said plurality of partition barcode sequences.
298. The method of embodiment 297, further comprising, prior to (d), recovering said plurality of probe-associated nucleic acid molecules from said additional plurality of partitions.
299. The method of embodiment 298, wherein (d) comprises using a plurality of nucleic acid barcode molecules comprising said plurality of barcode sequences to attach said plurality of barcode sequences to first probes of said plurality of probe-associated nucleic acid molecules.
300. The method of embodiment 299, wherein each partition of said plurality of partitions comprises a different barcode sequence of said plurality of barcode sequences.

ADDITIONAL EMBODIMENTS

In some cases, the present disclosure provides a method according to the following additional embodiments:
1. A method of analyzing a sample comprising a nucleic acid molecule, comprising:
  a. providing:
    (i) a sample comprising said nucleic acid molecule, wherein said nucleic acid molecule comprises a first target region and a second target region, wherein said first target region and said second target region are disposed on a same strand of said nucleic acid molecule;
    (ii) a first probe comprising a first probe sequence and a second probe sequence, wherein said first probe sequence of said first probe is complementary to said first target region of said nucleic acid molecule; and
    (iii) a second probe comprising a third probe sequence, wherein said third probe sequence of said second probe is complementary to said second target region of said nucleic acid molecule;
  b. subjecting said sample to conditions sufficient to (i) hybridize said first probe sequence of said first probe to said first target region of said nucleic acid molecule, and (ii) hybridize said third probe sequence of said second probe to said second target region of said nucleic acid molecule to yield a probe-associated nucleic acid molecule;
  c. subjecting said probe-associated nucleic acid molecule to conditions sufficient to yield a probe-linked nucleic acid molecule comprising said first probe linked to said second probe; and
  d. within a partition, attaching a barcode sequence to said probe-linked nucleic acid molecule.
2. The method of embodiment 1, wherein said partition is a well among a plurality of wells.
3. The method of embodiment 1, wherein said partition is a droplet among a plurality of droplets.
4. The method of any one of embodiments 1-3, wherein (d) comprises (i) providing, in said partition, a nucleic acid barcode molecule comprising a binding sequence and a barcode sequence, wherein said binding sequence is complementary to said second probe sequence of said first probe, and (ii) subjecting said partition to conditions sufficient to hybridize said binding sequence to said second probe sequence.
5. The method of embodiment 4, further comprising subjecting said partition to conditions sufficient to conduct a nucleic acid extension reaction to generate a barcoded nucleic acid molecule comprising a sequence corresponding to said first probe, a sequence corresponding to said second probe, and a sequence corresponding to said barcode sequence.
6. The method of embodiment 4, further comprising subjecting said partition to conditions sufficient to ligate said probe-linked nucleic acid molecule to said nucleic acid barcode molecule to generate a barcoded nucleic acid molecule comprising a sequence corresponding to said first probe, a sequence corresponding to said second probe, and a sequence corresponding to said barcode sequence.
7. The method of embodiment 5 or 6, further comprising subjecting said barcoded nucleic acid molecule to conditions sufficient to conduct an amplification reaction to generate an amplification product, which amplification product comprises nucleic acid molecules comprising said sequence corresponding to said first probe, said sequence corresponding to said second probe, and said sequence corresponding to said barcode sequence.
8. The method of embodiment 7, wherein said amplification reaction comprises use of a primer comprising one or more functional sequences and wherein said amplification product comprises nucleic acid molecules further comprising said one or more functional sequences.
9. The method of any one of embodiments 7 or 8, wherein said amplification is isothermal amplification.
10. The method of any one of embodiments 7-9, wherein said amplification reaction is performed within said partition.
11. The method of embodiment 10, further comprising recovering said amplification product from said partition.
12. The method of any one of embodiments 7-9, wherein said amplification reaction is performed outside of said partition.
13. The method of any one of embodiments 7-12, further comprising sequencing said amplification product or a derivative thereof
14. The method of any one of embodiments 1-3, further comprising (i) providing a splint oligonucleotide comprising a first sequence complementary to said second probe sequence and a second sequence, and (ii) subjecting said partition to conditions sufficient to hybridize said first sequence of said splint oligonucleotide to said second probe sequence.
15. The method of embodiment 13, wherein said first sequence of said splint oligonucleotide hybridizes to said second probe sequence prior to (c).
16. The method of embodiment 13, wherein said first sequence of said splint oligonucleotide hybridizes to said second probe sequence after (c).
17. The method of any one of embodiments 13-16, wherein (d) comprises (i) providing, in said partition, a nucleic acid barcode molecule comprising a binding sequence and a barcode sequence, wherein said binding sequence is complementary to said second sequence of said splint oligonucleotide, and (ii) subjecting said partition to conditions sufficient to hybridize said binding sequence to said second sequence of said splint oligonucleotide.

18. The method of embodiment 17, wherein said binding sequence of said nucleic acid barcode molecule comprises one or more ribobases.
19. The method of embodiment 17 or 18, further comprising subjecting (i) said splint oligonucleotide hybridized to said second probe sequence and (ii) said nucleic acid barcode molecule to conditions sufficient to ligate said probe-linked nucleic acid molecule to said nucleic acid barcode molecule.
20. The method of any one of embodiments 17-19, further comprising subjecting (i) said splint oligonucleotide hybridized to said second probe sequence and (ii) said nucleic acid barcode molecule to conditions sufficient to conduct a nucleic acid extension reaction to generate a barcoded nucleic acid molecule comprising a sequence corresponding to said first probe, a sequence corresponding to said second probe, and a sequence corresponding to said barcode sequence.
21. The method of any one of embodiments 19 or 20, further comprising subjecting said barcoded nucleic acid molecule to conditions sufficient to conduct an amplification reaction to generate an amplification product, which amplification product comprises nucleic acid molecules comprising said sequence corresponding to said first probe, said sequence corresponding to said second probe, and said sequence corresponding to said barcode sequence.
22. The method of embodiment 21, wherein said amplification reaction is a polymerase chain reaction.
23. The method of embodiment 21 or 22, wherein said amplification reaction is performed within said partition.
24. The method of embodiment 23, further comprising recovering said amplification product from said partition.
25. The method of embodiment 21 or 22, wherein said amplification reaction is performed outside of said partition.
26. The method of any one of embodiments 21-25, wherein said amplification reaction is isothermal amplification.
27. The method of any one of embodiments 21-26, further comprising sequencing said amplification product or derivative thereof
28. The method of any one of embodiments 4-27, wherein said nucleic acid barcode molecule further comprises a unique molecular identifier sequence, a sequencing primer sequence, and/or a partial sequencing primer sequence.
29. The method of any one of embodiments 4-28, wherein, subsequent to (c), said probe-associated nucleic acid molecule is co-partitioned with said nucleic acid barcode molecule.
30. The method of any one of embodiments 4-28, wherein, subsequent to (a), said nucleic acid molecule is co-partitioned with said first probe, said second probe, and said nucleic acid barcode molecule.
31. The method of embodiment 30, wherein (c) is performed within said partition.
32. The method of embodiment 31, wherein (b) and (c) are performed within said partition.
33. The method of any one of embodiments 4-32, wherein said second probe comprises a fourth probe sequence, and wherein said method further comprises providing a nucleic acid binding molecule in said partition, wherein said nucleic acid binding molecule comprises a second binding sequence that is complementary to said fourth probe sequence of said second probe.
34. The method of embodiment 33, further comprising hybridizing said second binding sequence to said fourth probe sequence of said second probe within said partition.
35. The method of any one of embodiments 4-34, wherein said nucleic acid barcode molecule is coupled to a bead.
36. The method of embodiment 35, wherein said bead is a gel bead.
37. The method of embodiment 35 or 36, wherein said nucleic acid barcode molecule is coupled to said bead via a labile moiety.
38. The method of any one of embodiments 35-37, wherein said bead comprises a plurality of nucleic acid barcode molecules coupled thereto, wherein said plurality of nucleic acid barcode molecules comprise said nucleic acid barcode molecule.
39. The method of embodiment 38, wherein said bead comprises at least 100,000 nucleic acid barcode molecules coupled thereto.
40. The method of embodiment 38 or 39, wherein said plurality of nucleic acid barcode molecules are releasably coupled to said bead.
41. The method of embodiment 40, wherein said plurality of nucleic acid barcode molecules are releasable from said bead upon application of a stimulus.
42. The method of embodiment 41, wherein said stimulus is selected from the group consisting of a thermal stimulus, a photo stimulus, a biological stimulus, and a chemical stimulus.
43. The method of embodiment 42, wherein said stimulus is a reducing agent.
44. The method of any one of embodiments 41-43, wherein the application of said stimulus results in one or more of (i) cleavage of a linkage between nucleic acid barcode molecules of said plurality of nucleic acid barcode molecules and said bead, and (ii) degradation of said bead to release nucleic acid barcode molecules of said plurality of nucleic acid barcode molecules from said bead.
45. The method of any one of embodiments 35-44, wherein said bead is provided in said partition, and wherein said nucleic acid barcode molecule is released from said bead within said partition.
46. The method of any one of embodiments 1-45, wherein (c) is performed before (d).
47. The method of any one of embodiments 1-45, wherein (d) is performed before (c).
48. The method of any one of embodiments 1-47, wherein said first probe or said second probe further comprises a barcode sequence or unique molecular identifier.
49. The method of any one of embodiments 1-48, wherein said second probe comprises a fourth probe sequence, which fourth probe sequence hybridizes to a third target region of said nucleic acid molecule.
50. The method of embodiment 49, wherein said second target region is not adjacent to said third target region, and wherein said third probe sequence and said fourth probe sequence of said second probe are separated by a linker sequence.
51. The method of any one of embodiments 1-50, wherein said first probe sequence of said first probe comprises a first reactive moiety and said third probe sequence of said second probe comprises a second reactive moiety, wherein, subsequent to (b), said first reactive moiety is adjacent to said second reactive moiety.
52. The method of embodiment 51, wherein (c) comprises subjecting said first reactive moiety and said second reactive moiety to conditions sufficient to link said first probe sequence to said third probe sequence.

53. The method of embodiment 51 or 52, wherein said first reactive moiety of said first probe or said second reactive moiety of said second probe comprises an azide moiety, an alkyne moiety, a phosphorothioate moiety, an iodide moiety, an amine moiety, or a phosphate moiety.
54. The method of any one of embodiments 51-53, wherein said first probe is linked to said second probe in said probe-linked nucleic acid molecule via a linker, wherein said linker comprises a triazole moiety, a phosphorothioate bond, or a phosphoroamidatephosphoramidate bond.
55. The method of any one of embodiments 1-50, wherein (c) comprises performing an enzymatic ligation reaction and/or an extension reaction.
56. The method of embodiment 55, wherein said enzymatic ligation reaction and/or said extension reaction comprises use of an enzyme selected from the group consisting of T4 RNL2, SplintR, T4 DNA ligase, KOD ligase, PBCV1, DNA polymerase, and Mu polymerase, or a derivative thereof
57. The method of any one of embodiments 1-56, wherein, prior to (a), said first probe is linked to said second probe via one or more linking sequences.
58. The method of embodiment 57, wherein said one or more linking sequences comprise one or more of a spacer sequence, a sequencing primer or complement thereof, a capture sequence, a restriction site, a transposition site, and a unique molecular identifier sequence.
59. The method of embodiment 57 or 58, wherein said one or more linking sequences comprise a thermolabile, photocleavable, or enzymatically cleavable site.
60. The method of any one of embodiments 1-59, wherein said first target region is adjacent to said second target region.
61. The method of any one of embodiments 1-59, wherein said first target region and said second target region are separated by a gap region disposed between said first target region and said second target region.
62. The method of embodiment 61, wherein said gap region is at least one nucleotide long.
63. The method of embodiment 62, wherein said gap region is at least 10 nucleotides long.
64. The method of embodiment 63, wherein said gap region is at least 100 nucleotides long.
65. The method of any one of embodiments 1-64, further comprising digesting one or more nucleic acid molecules or portions thereof using an exonuclease.
66. The method of any one of embodiments 1-65, wherein said first probe or said second probe comprises a known sequence or a degenerate sequence.
67. The method of any one of embodiments 1-66, wherein said first probe or said second probe comprises a Phi-29 based rolling circle amplification sequence.
68. The method of any one of embodiments 1-67, wherein said first probe or said second probe comprises a cleavable site, wherein said cleavable site is cleavable using a thermal, photo-, chemical, or biological stimulus.
69. The method of any one of embodiments 1-68, further comprising contacting said first probe or said second probe with a transposase.
70. The method of any one of embodiments 1-69, wherein said sample comprises a cell, and wherein said nucleic acid molecule is contained within said cell.
71. The method of embodiment 70, further comprising, subsequent to (a), lysing or permeabilizing said cell, thereby providing access to said nucleic acid molecule.
72. The method of embodiment 70 or 71, wherein said cell is a prokaryotic cell.
73. The method of embodiment 70 or 71, wherein said cell is a eukaryotic cell.
74. The method of embodiment 70 or 71, wherein said cell is a human cell.
75. The method of any one of embodiments 70-74, wherein said cell is a fixed suspension cell or a formalin-fixed paraffin-embedded cell.
76. The method of any one of embodiments 70-75, wherein said cell is provided within said partition.
77. The method of embodiment 76, wherein said cell is a single cell.
78. The method of any one of embodiments 1-77, wherein said nucleic acid molecule is a ribonucleic acid (RNA) molecule.
79. The method of embodiment 78, wherein said nucleic acid molecule is a messenger RNA (mRNA) molecule.
80. The method of embodiment 78 or 79, wherein said nucleic acid molecule comprises a poly-A sequence at a terminus of said nucleic acid molecule.
81. The method of any one of embodiments 1-77, wherein said nucleic acid molecule is a deoxyribonucleic acid (DNA) molecule.
82. The method of any one of embodiments 1-81, wherein said partition further comprises one or more reagents selected from the group consisting of fluorophores, oligonucleotides, primers, nucleic acid barcode molecules, barcodes, buffers, deoxynucleotide triphosphates, DNA splints, detergents, reducing agents, chelating agents, oxidizing agents, nanoparticles, antibodies, temperature-sensitive enzymes, pH-sensitive enzymes, light-sensitive enzymes, proteases, ligases, polymerases, reverse transcriptases, restriction enzymes, nucleases, protease inhibitors, and nuclease inhibitors.
83. The method of embodiment 82, wherein said polymerase is a polymerase selected from the group of DNA polymerase, RNA polymerase, Hot Start polymerase, and Warm start polymerase
84. The method of any one of embodiments 1-83, wherein said sample comprises a cell bead, and wherein said nucleic acid molecule is contained within said cell bead.
85. The method of any one of embodiments 1-84, wherein (a)-(c) are performed without reverse transcription.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of analyzing a sample comprising a single cell or an isolated nucleus comprising a nucleic acid molecule, comprising:
   (a) providing:
      (i) the sample comprising the single cell or the isolated nucleus comprising the nucleic acid molecule, wherein the nucleic acid molecule comprises a first target region and a second target region, and wherein the first target region and the second target region are both disposed on a strand of the nucleic acid molecule;
      (ii) a first probe comprising a first probe sequence and a first barcode sequence that identifies the sample, wherein the first probe sequence of the first probe is complementary to the first target region of the nucleic acid molecule; and
      (iii) a second probe comprising a second probe sequence, wherein the second probe sequence of the second probe is complementary to the second target region of the nucleic acid molecule;
   (b) subjecting the sample to conditions sufficient to (i) hybridize the first probe sequence of the first probe to the first target region of the nucleic acid molecule, and (ii) hybridize the second probe sequence of the second probe to the second target region of the nucleic acid molecule to yield a probe-associated nucleic acid molecule comprising the nucleic acid molecule hybridized to the first probe and the second probe;
   (c) subjecting the probe-associated nucleic acid molecule to conditions sufficient to link the first probe to the second probe, thereby generating an additional nucleic acid molecule comprising the first probe linked to the second probe; and
   (d) using the additional nucleic acid molecule and a polynucleotide that comprises a second barcode sequence to generate a barcoded nucleic acid molecule comprising (i) a sequence corresponding to the first target region and the second target regions, (ii) the first barcode sequence or reverse complement thereof, and (iii) the second barcode sequence or reverse complement thereof, wherein the second barcode sequence or reverse complement thereof identifies the single cell or isolated nucleus.

2. The method of claim 1, wherein (d) is performed in a partition.

3. The method of claim 2, wherein the partition is selected from a well among a plurality of wells and a droplet among a plurality of droplets.

4. The method of claim 2, wherein (d) comprises (i) providing, in the partition, the polynucleotide comprising the second barcode sequence and a binding sequence, wherein the binding sequence is complementary to a first sequence of the first probe or a second sequence of the second probe, and (ii) subjecting the partition to conditions sufficient to hybridize the binding sequence to the first sequence or the second sequence.

5. The method of claim 4, further comprising subjecting the partition to conditions sufficient to conduct a nucleic acid extension reaction to generate the barcoded nucleic acid molecule.

6. The method of claim 1, wherein the polynucleotide is coupled to a support.

7. The method of claim 5, further comprising subjecting the barcoded nucleic acid molecule to conditions sufficient to conduct an amplification reaction to generate an amplification product, which amplification product comprises nucleic acid molecules corresponding to the barcoded nucleic acid molecule.

8. The method of claim 7, wherein the amplification reaction comprises use of a primer comprising one or more functional sequences, and wherein the nucleic acid molecules further comprise the one or more functional sequences.

9. The method of claim 7, wherein the amplification reaction is an isothermal amplification reaction.

10. The method of claim 7, wherein the amplification reaction is performed within the partition.

11. The method of claim 10, further comprising recovering the amplification product from the partition.

12. The method of claim 7, wherein the amplification reaction is performed outside of the partition.

13. The method of claim 1, further comprising sequencing the barcoded nucleic acid molecule or derivative thereof.

14. The method of claim 1, wherein the polynucleotide further comprises a unique molecular identifier sequence, a sequencing primer sequence, or a partial sequencing primer sequence.

15. The method of claim 1, wherein, after (b), a gap region comprising one or more nucleotides occurs between the first probe and the second probe hybridized to the nucleic acid molecule.

16. The method of claim 15, wherein the gap region comprises at least about 10 nucleotides.

17. The method of claim 15, wherein the gap region comprises at least about 100 nucleotides.

18. The method of claim 15, wherein the gap region is filled with nucleotides prior to or during (c).

19. The method of claim 6, wherein the support is a bead.

20. The method of claim 19, wherein the bead is a gel bead.

21. The method of claim 6, wherein the polynucleotide is releasably coupled to the support.

22. The method of claim 1, wherein the first barcode sequence and the second barcode sequence are different from one another.

23. The method of claim 1, wherein the single cell or the isolated nucleus is fixed with a fixative.

24. The method of claim 23, wherein the fixative is selected from the group consisting of formaldehyde, paraformaldehyde, and formalin.

25. The method of claim 23, wherein the single cell or the isolated nucleus is further permeabilized.

26. The method of claim 1, further comprising, in (c), linking the first probe to the second probe using ligation.

27. The method of claim 4, wherein the second barcode sequence identifies the barcoded nucleic acid molecule as having been generated in the partition.

28. The method of claim 19, wherein the polynucleotide is coupled to the bead via a labile moiety.

29. The method of claim 28, wherein the labile moiety is selected from a thermolabile moiety, a photocleavable moiety, and an enzymatically cleavable moiety.

* * * * *